US009759570B2

(12) United States Patent
Joao et al.

(10) Patent No.: US 9,759,570 B2
(45) Date of Patent: Sep. 12, 2017

(54) PERSONAL MONITORING APPARATUS AND METHOD

(71) Applicants: Raymond Anthony Joao, Yonkers, NY (US); Mary Antonette Spano, Yonkers, NY (US)

(72) Inventors: Raymond Anthony Joao, Yonkers, NY (US); Mary Antonette Spano, Yonkers, NY (US)

( * ) Notice: Subject to any disclaimer, the term of this patent is extended or adjusted under 35 U.S.C. 154(b) by 0 days.

(21) Appl. No.: 14/953,253

(22) Filed: Nov. 27, 2015

(65) Prior Publication Data

US 2016/0155310 A1    Jun. 2, 2016

Related U.S. Application Data

(60) Provisional application No. 62/085,587, filed on Nov. 30, 2014.

(51) Int. Cl.
| | |
|---|---|
| *G08B 23/00* | (2006.01) |
| *G01C 21/34* | (2006.01) |
| *G01S 19/13* | (2010.01) |
| *G06F 17/30* | (2006.01) |
| *G06F 19/00* | (2011.01) |
| *H04W 4/02* | (2009.01) |
| *H04W 4/22* | (2009.01) |

(Continued)

(52) U.S. Cl.
CPC ............. *G01C 21/34* (2013.01); *G01S 19/13* (2013.01); *G06F 17/30241* (2013.01); *G06F 19/322* (2013.01); *G06F 19/3406* (2013.01); *G08B 21/0202* (2013.01); *G08B 21/0208* (2013.01); *G08B 21/0269* (2013.01); *G08B 21/0277* (2013.01); *G08B 21/0291* (2013.01); *G08B 25/014* (2013.01); *G08B 25/08* (2013.01); *H04M 11/04* (2013.01); *H04W 4/021* (2013.01); *H04W 4/027* (2013.01); *H04W 4/22* (2013.01); *G01C 21/00* (2013.01)

(58) Field of Classification Search
CPC ... G08B 21/02; G08B 5/228; G06F 17/30241; G06F 19/322; G06F 19/3406; G01S 19/13; H04W 4/027; H04W 4/22; G01C 21/34

See application file for complete search history.

(56) References Cited

U.S. PATENT DOCUMENTS

| | | |
|---|---|---|
| 5,917,405 A | 6/1999 | Joao |
| 6,542,076 B1 | 4/2003 | Joao |

(Continued)

*Primary Examiner* — Erin File
(74) *Attorney, Agent, or Firm* — Raymond A. Joao, Esq.

(57) ABSTRACT

An apparatus, including a housing, display; keyboard; at least one microphone; at least one speaker; at least two cameras; memory or database which stores travel schedule or itinerary information for an individual global positioning device; communication equipment, controller; and transmitter. If the controller detects a deviation of the apparatus from a travel schedule or itinerary or detects an absence of or leaving of the apparatus from an expected location, the controller generates a message and the transmitter transmits the message to a communication device associated with a third party. The controller activates the communication equipment to initiate a telephone call to the communication device or a second communication device, de-activates an on/off switching functionality of the apparatus, and deactivates a telephone calling on/off switching functionality.

30 Claims, 12 Drawing Sheets

(51) Int. Cl.
  *G08B 21/02* (2006.01)
  *G08B 25/01* (2006.01)
  *G08B 25/08* (2006.01)
  *H04M 11/04* (2006.01)
  *G01C 21/00* (2006.01)

(56) References Cited

U.S. PATENT DOCUMENTS

| | | | |
|---|---|---|---|
| 6,542,077 B2 | 4/2003 | Joao | |
| 6,549,130 B1 | 4/2003 | Joao | |
| 6,587,046 B2 | 7/2003 | Joao | |
| 7,253,731 B2 | 8/2007 | Joao | |
| 7,277,010 B2 | 10/2007 | Joao | |
| 7,397,363 B2 | 7/2008 | Joao | |
| 7,482,920 B2 | 1/2009 | Joao | |
| 8,255,830 B2 | 8/2012 | Ording et al. | |
| 8,868,028 B1* | 10/2014 | Kaltsukis | H04W 4/028 455/404.1 |
| 9,075,136 B1 | 7/2015 | Joao | |
| 2003/0174202 A1* | 9/2003 | Eshkoli | H04M 3/567 348/14.08 |
| 2003/0193404 A1 | 10/2003 | Joao | |
| 2003/0206102 A1 | 11/2003 | Joao | |
| 2004/0087314 A1* | 5/2004 | Duncan | G01C 21/00 455/456.1 |
| 2004/0132461 A1* | 7/2004 | Duncan | G01C 21/00 455/456.1 |
| 2004/0160319 A1 | 8/2004 | Joao | |
| 2005/0248444 A1 | 11/2005 | Joao | |
| 2006/0199612 A1 | 9/2006 | Beyer et al. | |
| 2007/0085993 A1 | 4/2007 | Brown, Jr. | |
| 2007/0152980 A1 | 7/2007 | Kocienda et al. | |
| 2008/0065908 A1* | 3/2008 | Appaji | G06F 12/1425 713/193 |
| 2008/0234878 A1 | 9/2008 | Joao | |
| 2009/0146805 A1 | 6/2009 | Joao | |
| 2009/0186596 A1* | 7/2009 | Kaltsukis | G08B 25/08 455/404.2 |
| 2009/0219403 A1 | 9/2009 | McCaffrey et al. | |
| 2009/0309751 A1 | 12/2009 | Kano et al. | |
| 2010/0102122 A1* | 4/2010 | Skowronek | G06Q 20/32 235/380 |
| 2010/0216509 A1 | 8/2010 | Riemer et al. | |
| 2011/0046920 A1 | 2/2011 | Amis | |
| 2011/0117878 A1* | 5/2011 | Barash | G08B 21/0211 455/404.2 |
| 2011/0248838 A1 | 10/2011 | Krahenbuhl et al. | |
| 2012/0133770 A1 | 5/2012 | Joao | |
| 2013/0029730 A1 | 1/2013 | Harada | |
| 2013/0122968 A1 | 5/2013 | Miura et al. | |
| 2014/0006472 A1* | 1/2014 | Brink | G06F 3/1431 709/201 |
| 2014/0078275 A1 | 3/2014 | Joao et al. | |
| 2014/0085445 A1 | 3/2014 | Joao et al. | |
| 2014/0171048 A1* | 6/2014 | Sanaullah | H04W 4/16 455/416 |
| 2014/0318699 A1* | 10/2014 | Longinotti-Buitoni | A61B 5/0002 156/247 |
| 2014/0354402 A1 | 12/2014 | Joao | |
| 2015/0298654 A1 | 10/2015 | Joao et al. | |

\* cited by examiner

PERSONAL MONITORING APPARATUS AND METHOD

RELATED APPLICATIONS

This application claims the benefit of the priority of U.S. Provisional Patent Application Ser. No. 62/085,587, filed Nov. 30, 2014, and entitled "PERSONAL MONITORING APPARATUS AND METHOD", the subject matter and teachings of which are hereby incorporated by reference herein in their entirety.

FIELD OF THE INVENTION

The present invention pertains to a personal monitoring apparatus and method and, in particular, to a personal monitoring apparatus and method which can be utilized to monitor infants, children, the elderly, or individuals of any and./or all ages and/or to monitor their position or location, their whereabouts, their surroundings, their vital signs, their physiological measurements, states, or condition, and/or any individual and/or individuals with whom they may come into contact.

BACKGROUND OF THE INVENTION

All to often we hear horror stories about children being lost, abducted, left in vehicles, left on school buses, or falling ill, or are found in, or placed in, any type or kind of dangerous or precarious predicament. We also hear of individuals and, in particular, elderly individuals, becoming lost, disoriented, falling ill, or otherwise being in other precarious predicaments. Lastly, we also hear of individuals of any and/or all ages suddenly falling ill or being in need of emergency medical attention or in need of other assistance.

While so-called "amber alerts" provide a public notification system or method which alerts or notifies the public regarding a missing child, and while so-called "silver alerts" are a public notification system or method which alerts or notifies the public regarding a missing person, a missing adult, or a missing elderly person afflicted with a condition such as Alzheimer's, Dementia, or other condition, these public notification systems are flawed in that they rely on members of the public to actually find, look out for, and/or find and/or report, the missing child or missing person. If the missing child or missing person becomes disoriented, falls ill, gets lost in an isolated area, becomes fearful and/or tries to hide from others, the above-described public notification systems can be futile in finding the missing child or missing person.

Providing children and adults of all ages with personal communication devices such as cellular telephones, personal digital assistants, or like communication devices, can also prove useless when the child or adult falls ill, panics, is unable to speak, becomes unconscious, or is otherwise unable to utilize such a personal communication device.

In this regard, it is submitted that the prior art systems which seek to find, locate, and provide assistance to, missing children and adults have many shortcomings and do not provide an effective means by which to find, locate, and assist, these missing children and adults.

SUMMARY

The present invention pertains to a personal monitoring apparatus and method and, in particular, to a personal monitoring apparatus and method which can be utilized to monitor infants, children, the elderly, or individuals of any and./or all ages, and/or to monitor their position or location, their whereabouts, their surroundings, their vital signs, their physiological measurements, states, or condition, and/or any individual and/or individuals with whom they may come into contact, which overcomes the shortfalls of the prior art.

The present invention can provide an apparatus and method which can be utilized to monitor and/or to track the whereabouts and/or travels of an individual at any time, to compare an individual's current whereabouts to their current location or a location where they should be, ought to be, or are expected to be, and/or to provide an alert, or to provide a notification, to the individual, a parent of the individual, a child of the individual, a relative of the individual, a caregiver of the individual, an employer of the individual, a law enforcement agency or law enforcement personnel, emergency services personnel, a third party, or any other person or entity, when the individual is located at a location where they should not be, wherein they ought not be, where they are not expected to be, or when they have deviated from, or are deviating from, a planned, an expected, or a desired, travel route, or a planned, expected, or desired, schedule when they itinerary.

The present invention can be used to monitor the whereabouts, the location, or the travel, of a child of any age, a child having special needs, a child who has become injured or ill, or a child who has become lost, mission, or who has become a victim of foul play. The present invention can be used to monitor the whereabouts, the location, or the travel, of an adult or an elderly individual of any age, an adult or an elderly individual having special needs, an adult or an elderly individual who has become ill or injured, or an adult or an elderly individual who has become lost, mission, or who has become a victim of foul play.

The present invention can also be utilized to provide information or an indication, to the individual or to any persons with whom the individual may come into contact, which can provide information indicative of the individual being where he or she should not be, indicative that the individual is lost, indicative that the individual is or might be injured or ill, or indicative that the individual is in need of help or assistance.

The present invention can also be utilized to provide information or an indication, to a parent of the individual, to a child of the individual, to a relative of the individual, to a caregiver of the individual, to an employer of the individual, to a law enforcement agency or law enforcement personnel, to an emergency services personnel, to any third party, or to any other person or entity, when the individual has been determined to be lost, injured, ill, or otherwise in need of help or assistance.

The present invention can also be utilized to obtain, record, store, and/or provide, healthcare information or physiological data and/or information, or any other information regarding the state or status of an individual, including, but not limited to, the individual's heart rate, blood pressure, body temperature, blood sugar level, or any other physical condition, physiological condition, or healthcare condition, which can be measured or measurable by any wearable device or by any implanted device or implantable device.

The present invention can also be utilized to initiate, establish, and/or maintain, a communication link, or a telephone call, with and between any of the herein-described personal monitoring devices with and any of the herein-described user communication devices, central processing computers, and/or law enforcement communication devices and/or emergency services communication devices. In this regard, for example, a line communication can be established with and/or between the personal monitoring device of a lost, mission, or ill, child's and a user communication device of, associated with, or used by, the child's parent, relative, caregiver, or other authorized person. The present invention can also be utilized to provide an open, and speakerphone-operated, line of communication with the personal monitoring device so that a respective parent, relative, caregiver, or other authorized person can, using a user communication device, speak to, or engage in conversation with, the child or with any individual with whom the child comes into contact so as to facilitate finding the child, helping the child find help of his or her way back to a safe location, and/or making sure that the child is brought to a place of safety and/or is safely returned home or to another safe location, and/or to make sure that the child's needs are provided for until being reunited with his or her parent(s), a caregiver, or law enforcement. The present invention can also be utilized in a same, a similar, or an analogous, manner in providing personal monitoring for adults and elderly individuals of any age.

The present invention can also be utilized in order to establish, and to provide services for, personal monitoring accounts for individuals. In a preferred embodiment, a personal monitoring account can be assigned to an individual in order to provide any number or monitoring services for that individual. For example, a personal monitoring account can be utilized to allow any other authorized individual, person, or entity, to monitor, and/or to track location, position, or movement of, an individual, to communicate with the individual at any time, to communicate with people in the vicinity of the individual, to obtain information regarding the position, location, or whereabouts of the individual, persons with whom the individual may be in contact with, or may have come into contact with, the individual's itinerary, travels, to obtain video and/or audio information regarding the individual, his or her travels, locations, and/or any other information regarding the individual. In a preferred embodiment, one or more personal monitoring accounts can be set up by or for an individual. In this regard, an individual can have one personal monitoring account ("PMA") or a plurality of personal monitoring accounts.

The present invention can be utilized to provide a number of various features and functionality which can be useful in providing personal monitoring services and operations for infants, children, and adults, of any ages. The apparatus and method of the present invention can also be utilized to provide personal monitoring services and operations for and regarding pets and animals of any type or kind.

The apparatus of the present invention includes a personal monitoring device. The personal monitoring device can be any suitable communication device and can be, a cellular telephone, a mobile telephone or wireless telephone, a Smartphone, a personal digital assistant, or any other suitable device. The personal monitoring device can be equipped with the communication equipment typically found in cellular telephones, mobile telephones or wireless telephones, Smartphones, personal digital assistants, or any other suitable devices, for facilitating a two-way communication with other individuals or entities and/or with communications devices, computers, equipment, or any other communication equipment used by any individuals or entities. The personal monitoring device can also be equipped with global positioning system (GPS) device or equipment. The personal monitoring device can also be equipped with navigation equipment such as are typically found in commercially available GPS navigation devices and equipment which are used to assist motorists and individuals traveling in motor vehicles in navigating from a location to a destination.

The personal monitoring device can also be equipped with global positioning system (GPS) equipment and navigation equipment which can allow the personal monitoring device to act in a stand-alone manner, without having to obtain any navigation information from any external device or computer. The personal monitoring device can be equipped to receive, and provide to a user, navigation data and/or information, including, but not limited to, navigation instructions, which is obtained from an external computer or communication device or a service provider computer or communication device.

The personal monitoring device can be any communication device, computer, personal computer, laptop computer, notebook computer, Smartphone or smartphone, smart telephone, cellular telephone, personal digital assistant, tablet, tablet computer, watch, smart watch, or wearable device or computer, an implantable device or computer, an item of jewelry, eyeglasses, or any accessory, or any combination of same, or any equivalent of same, which can be utilized by any person, individual, or entity, who or which utilizes the present invention. The personal monitoring device can also be a server computer, a mainframe computer, a mini-computer, a microcomputer, or any other computer or device for suiting the needs of the particular user.

Any number of personal monitoring devices can be utilized by or in conjunction with the apparatus of the present invention. The personal monitoring device can communicate, in a bi-directional manner and/or otherwise, with and/or can operate in conjunction with any the herein-described computers, communication devices, and/or computer systems described herein as being utilized in connection with the apparatus and method of the present invention.

The apparatus of the present invention also includes a central processing computer or central processing computer system, which can be any computer or computer system or can be a any computer utilized in a network with other computers or a server computer. The central processing computer can provide control over the apparatus of the present invention and can perform any of the various processing services and/or functions described herein as being performed by same. The central processing computer can be a single computer or a system of computers and/or may include a plurality of computers or computer systems which are utilized in conjunction with one another. The central processing computer can also provide personal monitoring services for or regarding any number of individuals and/or entities and/or can provide personal monitoring services for or regarding any number of individuals and/or entities who or which need, want, or desire, to monitor, to monitor the whereabouts of, and/or who or which desire to be notified regarding the whereabouts, location, healthcare status, or any occurrence of or regarding any event which may give rise to a need to find, locate, and/or monitor a location of, any child, adult, elderly person, or any individual of any age.

Any number of central processing computers can be utilized by or in conjunction with the apparatus of the present invention. The central processing computer(s) can communicate, in a bi-directional manner and/or otherwise, with, and/or can operate in conjunction with, the personal monitoring device and/or any of the other communication devices, computers, and/or computer systems, associated with or used by any of the individuals and/or entities who or which utilize the apparatus and method of the present invention.

The apparatus of the present invention also includes a user communication device or computer which is associated with, or which can be used by, any one or more of any of the herein-described users, individuals, or entities, who or which utilize the apparatus and method of the present invention. Any number of user communication devices can be utilized by or in conjunction with any user or any individual or entity who or which utilizes the apparatus and method of the present invention, and any number of user communication devices can be utilized in conjunction with the apparatus and method of the present invention.

The user communication device(s) can communicate, in a bi-directional manner and/or otherwise, with, and/or can operate in conjunction with the personal monitoring device and/or the central processing computer and/or any of the other herein-described communication devices, computers, and/or computer systems, associated with or used by any of the individuals and/or entities who or which utilize the apparatus and method of the present invention.

The apparatus can also include a law enforcement communication device or computer which is associated with, or which can be used by, any law enforcement agency or department which utilize the apparatus and method of the present invention. Any number of law enforcement communication devices can be utilized by or in conjunction with any law enforcement agency or department which utilizes the apparatus and method of the present invention, and any number of law enforcement communication devices can be utilized in conjunction with the apparatus and method of the present invention.

The law enforcement communication device(s) can communicate, in a bi-directional manner and/or otherwise, with, and/or can operate in conjunction with the personal monitoring device, the central processing computer, the user communication device, and/or any of the other herein-described communication devices, computers, and/or computer systems, associated with or used by any of the individuals and/or entities who or which utilize the apparatus and method of the present invention.

The apparatus can also include an emergency services provider communication device or computer which is associated with, or which can be used by, any emergency services provider, agency, or department, which utilizes the apparatus and method of the present invention. Any number of emergency services provider communication devices can be utilized by or in conjunction with any emergency services provider, agency, or department, which utilizes the apparatus and method of the present invention, and any number of emergency services provider communication devices can be utilized in conjunction with the apparatus and method of the present invention.

The emergency services provider communication device(s) can communicate, in a bi-directional manner and/or otherwise, with, and/or can operate in conjunction with the personal monitoring device, the central processing computer, the user communication device, the law enforcement communication device, and/or any of the other herein-described communication devices, computers, and/or computer systems, associated with or used by any of the individuals and/or entities who or which utilize the apparatus and method of the present invention.

The apparatus can also include a healthcare records computer or communication device which can store an electronic healthcare record or electronic healthcare records for any of the herein-described individuals who or which can be monitored using the apparatus and method of the present invention. The healthcare records computer can also store healthcare records of any individual, children, adults, elderly persons, or any individual of any age, who is to be monitored by and using the apparatus and method of the present invention as well as any healthcare records of, for, or regarding, any relatives of any of these individuals.

The healthcare records computer or computers can serve to store and house an electronic healthcare record or any number of electronic healthcare records. The healthcare records computer can also be utilized to facilitate cloud storage of any electronic healthcare record(s).

The healthcare records computer(s) can communicate, in a bi-directional manner and/or otherwise, with, and/or can operate in conjunction with, the personal monitoring device, the central processing computer, the user communication device, the law enforcement communication device, the emergency services provider communication device, and/or any of the other communication devices, computers, and/or computer systems, associated with or used by any of the individuals and/or entities who or which utilize and/or operate in conjunction with the apparatus of the present invention.

Any of the personal monitoring device(s), the central processing computer(s), the user communication device(s), the law enforcement communication device(s), the emergency services provider communication device(s), and/or the healthcare records computer(s), can be any computer or communication device, including, but not limited to, a personal computer, a home computer, a server computer, or any computer capable of being utilized in a network or capable of being utilized with other computers in a network, a hand-held computer, a palmtop computer, a laptop computer, a personal communication device, a cellular telephone, a wireless telephone, a mobile telephone, a digital television, an interactive television, a digital television, a personal digital assistant, a telephone, a digital telephone, a television, an interactive television, a beeper, a pager, and/or a watch or a Smart watch, and/or any wearable device, computer or communication device.

Each of the personal monitoring device(s), the central processing computer(s), the user communication device(s), the law enforcement communication device(s), the emergency services provider communication device(s), and/or the healthcare records computer(s), can transmit information to, as well as receive information from, any of the computers or communication devices described herein. In this regard, each of the computers or communication devices described herein can communicate with, process information from, and/or share data and/or information with, each other and/or any other computer(s) or communication device(s) described herein and/or utilized in conjunction with the apparatus of the present invention. In this manner, any of the respective computer(s) or communication device(s) described herein can communicate with any other computer(s) or communication device(s) in a bi-directional manner.

The present invention can be utilized on, over, and/or via, the Internet and/or the World Wide Web and/or on any wireless communication network and/or any cellular communication network. The present invention, in the preferred embodiment, can also utilize wireless Internet and/or World Wide Web services, equipment and/or devices. The central processing computer(s) can have a web site or web sites associated therewith. Each of the other computers or communication devices described herein can also have a web site or web sites associated with same.

Although the Internet and/or the World Wide Web is a preferred communication system and/or medium utilized, the present invention, in any and/or all of the embodiments described herein, can also be utilized with any appropriate communication network or system including, but not limited to, a telecommunication network or system, a telephone communication network or system, a cellular communication network or system, a wireless communication network or system, a line or wired communication network or system, a wireless Internet network or system, a wireless World Wide Web network or system, a digital communication network or system, a personal communication network or system, a personal communication services (PCS) network or system, a satellite communication network or system, a broad band communication network or system, a low earth orbiting (LEO) satellite network or system, a public switched telephone network or system, a telephone communication network or system, a radio communication network or system, a cable television network or system, and/or any other communication network or system, and/or any combination of the above communication networks or systems.

Any of the personal monitoring device(s), the central processing computer(s), the user communication device(s), the law enforcement communication device(s), the emergency services provider communication device(s), and/or the healthcare records computer(s), can communicate with one another, and/or be linked to one another, over or via any communication network, telecommunication network, telephone network, a line-connected network, and/or a wireless communication network, and/or the Internet and/or the World Wide Web. Each of the computers or communication devices can be linked with any other computer or computers directly or indirectly with one another so as to facilitate a direct or indirect bi-directional communication between said respective computers or communication devices. Communications between each of the computers or communication devices can also involve an e-mail server or e-mail servers in those instances when e-mails are described as being used to transmit or to send any of the information, signals, messages, reports, notification messages, or any other communications, described herein, by or between any of the computers or communication devices or when any of the information, signals, messages, reports, notification messages, or any other computers or communications, described herein, are transmitted by and/or between any of the parties described herein and/or by or between any of the computers or communication devices or any other computers or communication devices, computer systems, communication network equipment, server computers, etc., or any other devices used or needed, in order to facilitate communications or the transmission of any of the herein-described information, signals, messages, reports, notification messages, or any other communications.

Each of the personal monitoring device(s), the central processing computer(s), the user communication device(s), the law enforcement communication device(s), the emergency services provider communication device(s), and/or the healthcare records computer(s), can communicate in a bi-directional manner with, and/or can send and/or receive signals, data, information, messages, reports, notification messages, alerts, or any other communications or electronic communication transmissions, to, from and/or between, any other, or any number of, other personal monitoring device(s), the central processing computer(s), the user communication device(s), the law enforcement communication device(s), the emergency services provider communication device(s), and/or the healthcare records computer(s).

Each of the personal monitoring device(s), the central processing computer(s), the user communication device(s), the law enforcement communication device(s), the emergency services provider communication device(s), and/or the healthcare records computer(s), can be linked to or with any other personal monitoring device(s), the central processing computer(s), the user communication device(s), the law enforcement communication device(s), the emergency services provider communication device(s), and/or the healthcare records computer(s), via a wired link or line or a wireless link. Each of the personal monitoring device(s), the user communication device(s), the law enforcement communication device(s), the emergency services provider communication device(s), and/or the healthcare records computer(s), can be connected with, or linked to or with, the central processing computer(s).

Any and/or all of the signals, data, information, messages, reports, notification messages, or any other communications, described herein as being transmitted from one device, computer, or communication device, to another device, computer, or communication device, can be, or can be included in, or can be attached to, an e-mail message, an instant messaging message, an electronic transmission, or an electronic data transmission or electronic data interchange, or can be transmitted via any other data or information transmission, and/or can be transmitted via or using any appropriate or necessary computer(s) or device(s).

Each of the personal monitoring device(s), the central processing computer(s), the user communication device(s), the law enforcement communication device(s), the emergency services provider communication device(s), and/or the healthcare records computer(s), can transmit data and/or information using TCP/IP, as well as any other Internet and/or World Wide Web, and/or communication, protocols.

The present invention can utilize electronic commerce technologies and security methods, techniques and technologies, including any encryption or security technologies and/or techniques, in any and/or all of the instances of data and/or information processing, and/or data and/or information transmission described herein.

Any and/or all of the signals, data, information, messages, reports, notification messages, or any other communications, described herein as being transmitted from one device, computer, or communication device, to another device, computer, or communication device, can be, or can be included in, or can be attached to, an e-mail message, an instant messaging message, an electronic transmission, or an electronic data transmission or electronic data interchange, or can be transmitted via any other data or information transmission, and/or can be transmitted via or using any appropriate or necessary computer(s) or device(s).

Each of the personal monitoring device(s), the central processing computer(s), the user communication device(s), the law enforcement communication device(s), the emergency services provider communication device(s), and/or the healthcare records computer(s), can transmit data and/or information using TCP/IP, as well as any other Internet and/or World Wide Web, and/or communication, protocols.

The present invention can utilize electronic commerce technologies and security methods, techniques and technologies, including any encryption or security technologies and/or techniques, in any and/or all of the instances of data and/or information processing, and/or data and/or information transmission described herein.

The personal monitoring device can be a cellular telephone, a wireless telephone, a mobile telephone, a Smartphone, a smartphone, or a personal digital assistant, or the personal monitoring device can be or can be a component of a personal computer, a home computer, a laptop computer, a notebook computer, a tablet computer, a tablet, a hand-held computer, a palmtop computer, a personal communication device, a cellular telephone, a wireless telephone, a mobile telephone, a Smartphone, a smartphone, a personal digital assistant, a digital television, an interactive television, a digital television, a telephone, a digital telephone, a television, an interactive television, a beeper, a pager, and/or a watch or a Smart watch, and/or any wearable device, computer or communication device. The personal monitoring device can also be a server computer, or any computer capable of being utilized in a network or capable of being utilized with other computers in a network The personal monitoring device can also be any communication device, computer, personal computer, laptop computer, notebook computer, Smartphone or smartphone, smart telephone, cellular telephone, personal digital assistant, tablet, tablet computer, watch, smart watch, or wearable device or computer, an implantable device or computer, an item of jewelry, eyeglasses, or any accessory, or any combination of same, or any equivalent of same.

The personal monitoring device includes a central processing unit or CPU which can be a microprocessor. The CPU can also be a microcomputer, a minicomputer, a macro-computer, and/or a mainframe computer, depending upon the application.

The personal monitoring device also includes a random access memory device(s) (RAM), a read only memory device(s) (ROM), each of which is connected to, or linked with, the CPU, and a user input device for inputting and/or entering data and/or information and/or instructions and/or commands into the personal monitoring device. The input device(s) can also be connected to, or linked with, the CPU.

The personal monitoring device can also include a display device for displaying data and/or information to a user or operator. The display device can also be connected to, or linked with, the CPU. The personal monitoring device can also include a transmitter(s) for transmitting signals and/or data and/or information to any one or more of the central processing computer(s), the user communication device(s), the law enforcement communication device(s), the emergency services provider communication device(s), and/or the healthcare records computer(s), and/or any other personal monitoring device(s) which may be utilized in conjunction with the present invention. The transmitter(s) can also be connected to, or linked with, the CPU. The personal monitoring device also includes a receiver(s) for receiving signals and/or data and/or information from any one or more of the central processing computer(s), the user communication device(s), the law enforcement communication device(s), the emergency services provider communication device(s), and/or the healthcare records computer(s), and/or any other personal monitoring device(s) which may be utilized in conjunction with the present invention. The receiver(s) can also be connected to, or linked with, the CPU.

The personal monitoring device also includes a database(s) which can also be connected to, or linked with, the CPU. The personal monitoring device can also include an output device(s) for outputting any of the data, information, and/or reports, described herein as being generated by or via the personal monitoring device. The output device(s) can also be connected to, or linked with, the CPU.

The personal monitoring device can also include a video and/or audio recording device(s) which can include a camera and/or a video recording device for recording pictures or video and/or video clips and/or a microphone or an audio recording device for recording audio or audio clips which can be recorded by, and/or transmitted live, by or from the personal monitoring device, or which can be recorded by, and stored at or in, the personal monitoring device for transmission by or from the personal monitoring device at a later time. The video and/or audio recording device(s) 10J can also be connected to, or linked with, the CPU.

The personal monitoring device can also include a global positioning system (GPS) device which can be utilized to determine or ascertain the location or position of the personal monitoring device at any time and/or to track movement of the personal monitoring device. The global positioning system (GPS) device can also be connected to, or linked with, the CPU.

The personal monitoring device can also include device functional equipment systems or devices which can include any necessary communications systems or devices which are typically found in cellular telephones or wireless telephones and/or which can allow the personal monitoring device to function as a cellular telephone or a wireless telephone. The functional equipment systems or devices can also include a global positioning system (GPS) device which can be utilized to determine or ascertain the location or position of the personal monitoring device at any time and which can be also be used to track movement of the personal monitoring device.

The functional equipment systems or devices can also include navigation equipment or devices which are typically found in navigation devices or equipment and which an be utilized to allow the personal monitoring device to function and/or to operate as a GPS equipped navigation device. The personal monitoring device can function as a stand alone navigation device, meaning that it can perform any and/or all needed and desired navigation tasks and functions without any interaction with an external computer or device, and/or without having to access a computer over any communication network in order to obtain navigation data, information, and/or instructions, for providing navigation data, information, and/or instructions, to a user of the personal monitoring device.

The functional equipment systems or devices can also include a "kill" switch or associated hardware and/or software for disabling and/or deactivating the personal monitoring device in instances when same might be lost or stolen, so as to prevent its use by another person and/or to prevent any access to any data and/or information stored therein, thereby rendering the personal monitoring device useless to another person after being reported, or discovered as being, lost or stolen.

The personal monitoring device can also operate in conjunction with an external computer or device in order to obtain navigation data, information, and/or instructions, so as to provide same to a user of the personal monitoring device. The personal monitoring device can also process navigation data, information, and/or instructions, on its own as well as receive at least some navigation data, information, and/or instructions, from an external computer or device, in order to provide navigation data, information, and/or instructions, to a user of the personal monitoring device. The functional equipment systems or devices can also be connected to, or linked with, the CPU.

The functional equipment systems or devices can also include any combination of hardware and/or software for disabling the on/off switch of the personal monitoring device, so that the personal monitoring device cannot be shut-off, or so that no operation or function of the personal monitoring device can be terminated, and/or so that a telephone call, a telephone communication link, or a communication line or link, cannot be turned off or terminated, by or at the personal communication device. In this regard, in the case of an emergency, no telephone call and/or communication line or link between the personal monitoring device and any user communication device(s), the or any central processing computer(s), the or any law enforcement communication device(s), the or any emergency services provider communication device(s), and/or the or any healthcare records computer(s), can be terminated at or by the personal monitoring device, so that a communication line, link, or channel can always be maintained with the personal monitoring device.

The functional equipment systems or devices can also include any combination of hardware and/or software for allowing the personal monitoring device and any components or devices therein or associated therewith to be remotely accessed, controlled, and/or monitored, by or using any authorized user communication device used by an authorized user or individual, the or any central processing computer(s), the or any law enforcement communication device(s), the or any emergency services provider communication device(s), and/or the or any healthcare records computer(s).

The personal monitoring device can be, or can be implemented in or with, a cellular telephone, a Smartphone, a smartphone, or a personal digital assistant, which can be equipped with all of the necessary hardware and software needed to perform all of the functions and functionality described herein as being performed by the personal monitoring device of the present invention. The personal monitoring device can also be designed to be of any size or shape, and/or the personal monitoring device can be implemented using a watch, a wristwatch, an necklace, a bracelet, a ring, or any other article of jewelry, of the personal monitoring device can be secured to a belt, a necklace, a bracelet, eyeglasses, a watch, a wristwatch, and/or can be attached to, secured to, or placed inside or within, any article of clothing, a jacket, a coat, a shirt, a blouse, a dress, a skirt, a pair of pants, shoes, sneakers, boots, a hat, gloves, socks, stockings, a tie, a scarf, or any other wearable item or accessory. In this regard, and depending of the use, application, or deployment, of the personal monitoring device in any given setting or situation, the personal monitoring device can be designed and/or configures to be of any size, shape, type, or kind, of device.

The personal monitoring device can include a housing, a display screen which can be any type or display screen and/or a touch screen and/or can be utilized to view and to input data, information, messages, or instructions. The display screen can also include a display section and a keyboard section. The keyboard section can be called upon when needed and can also be dispensed with when not being used so as to facilitate the use of the entirety of the display screen when desired.

The personal monitoring device can also be equipped with a flashlight, a flashlight bulb, or with any suitable software application which can turn the display screen, or any portion of the display screen, into a flashlight. In this regard, the personal monitoring device can be equipped with a flashlight or a flashlight functionality.

The personal monitoring device can also be equipped with a strobe light or with any suitable software application which can turn the display screen, or any portion of the display screen, into a strobe light. In this regard, the personal monitoring device can be equipped with a strobe light or a strobe light functionality.

The personal monitoring device can also include one or more microphones which can be located on one or more, or on any or all surfaces of the personal monitoring device in order to allow for any user or other individual to utilize the personal monitoring device to communicate with others, to allow others to monitor audio and/or sounds at or in the vicinity of the personal monitoring device, and/or to allow one to use, control an operation of, to enter voice commands into, and/or to record audio information or an audio clip with and/or using, the personal monitoring device, and/or to allow one to simply utilize the personal monitoring device to communicate with another individual or entity in a hand-free mode of operation. Any number of microphones can be utilized in connection with the personal monitoring device.

The personal monitoring device can also include one or more speakers which can be located on one or more, or on any or all, surfaces of the personal monitoring device in order to provide audible data, information, instructions, or communications, to any user, or individual who may be using, or who may be in the vicinity of, the personal monitoring device.

The personal monitoring device can also include one or more cameras which can be located on one or more, or on any or all, surfaces of the personal monitoring device in order to take or record a picture, a photograph, or an image, and/or to record video information or a video clip, with the personal monitoring device, to record a picture, a photograph, or an image, and/or to record video information or a video clip, of a user of the personal monitoring device or any individual using the personal monitoring device or in the vicinity of the personal monitoring device, to record a picture, a photograph, or an image, and/or to record video information or a video clip, of a vicinity in which the personal monitoring device is located or of a surrounding of same, and/or to allow a user or any individual to engage in a video conference or video chat with another individual or other individuals using the personal monitoring device.

Any one or more cameras can be a wide angle lens camera or a camera having a wide angle lens for obtaining maximum viewing area. Any one or more cameras can also be a night vision camera, an infrared camera, or a camera equipped with, or utilized in connection with, night vision capability.

The personal monitoring device can include a plurality of indicator lights, one of which can be used to provide an indication that the user of the personal monitoring device is located with a "safe" zone of travel and the other which can be used to provide an indication that the user of the personal monitoring device is located outside of a "safe" zone of travel, is lost, is ill, is possibly the victim of foul play, or is otherwise in need of help or assistance. An indicator light which is used to indicate the that user in within his or her "safe" zone can be an green light when illuminated, and an indicator light which is used to indicate the that the user outside his or her "safe" zone of travel, is lost, is ill, is possibly the victim of foul play, or is otherwise in need of help or assistance, can be a red light when illuminated. Indicator lights can also be provided via the display screen or in or via a portion or section of the display screen.

The personal monitoring device can include any suitable attachment device or element (not shown) which is attached or connected to, or linked with, the housing and/or the personal monitoring device and which can be used to secure, to mount, or to otherwise attach, the personal monitoring device to, on, or in, a belt, an article of clothing, a watch, a wristwatch, a necklace, a bracelet, eyeglasses, an accessory of any type or kind, a jacket, a coat, a shirt, a blouse, a dress, a skirt, a pair of pants, shoes, sneakers, boots, a hat, gloves, socks, stockings, a tie, a scarf, or any other wearable item or accessory.

The personal monitoring device, its housing, and its various component parts described herein, can be constructed or rugged materials in order to protect the personal monitoring device against impacts. In a preferred embodiment, the personal monitoring device, its housing, and its various component parts described herein, can also be sealed, in any appropriate manner, so as to provide for a personal monitoring device which can be waterproof. The personal monitoring device can also be designed and manufactured to as to include any suitable or buoyant material(s) which can allow the personal monitoring device to float on water. The housing, or any portion or component of same, can also include made with or from, or can contain a phosphorescent material so that the housing, or any portion of the housing, of the personal monitoring device can glow-in-the dark or otherwise exhibit glow-in-the-dark or luminescent properties.

The central processing computer can be any computer capable of performing the functionality of the central processing computer as described herein, a server computer, a computer system, a group of computers, a computer which can function in a network of and with other computers, or any other computer or communication device which can provide the functionality of, and which can be utilized as, a central processing computer. The central processing computer can also be any suitable server computer or server computer system, a cloud computer or cloud computer system, or a computer or computer system which can operate in a network of and with other computers or computer systems. The central processing computer can also be an Internet server computer and/or a web site server computer.

The central processing computer includes a central processing unit or CPU which can be a microprocessor. The CPU can also be a microcomputer, a minicomputer, a macro-computer, and/or a mainframe computer, depending upon the application.

The central processing computer also includes a random access memory device(s) RAM), a read only memory device(s) (ROM), each of which is connected to, or linked with, the CPU, and a user input device for inputting and/or entering data and/or information and/or instructions and/or commands into the central processing computer. The input device(s) can also be connected to, or linked with, the CPU. The central processing computer can also include a display device for displaying data and/or information to a user or operator. The display device can also be connected to, or linked with, the CPU.

The central processing computer can also include a transmitter(s) for transmitting signals and/or data and/or information to any one or more of the personal monitoring device(s), the user communication device(s), the law enforcement communication device(s), the emergency services provider communication device(s), and/or the healthcare records computer(s), and/or any other central processing computer(s), which may be utilized in conjunction with the present invention. The transmitter(s) can also be connected to, or linked with, the CPU. The central processing computer can also include a receiver(s) for receiving signals and/or data and/or information from any one or more of the personal monitoring device(s), the user communication device(s), the law enforcement communication device(s), the emergency services provider communication device(s), and/or the healthcare records computer(s), and/or any other central processing computer(s), which may be utilized in conjunction with the present invention. The receiver(s) can also be connected to, or linked with, the CPU.

The central processing computer also includes a database(s) which can contain and/or include any and/or all of the data and/or information needed or desired for or by the central processing computer to perform all of the operations, actions, functions, and/or functionality, described herein as being provided by, and/or as being performed by, the central processing computer and/or the apparatus of the present invention. The database(s) can also be connected to, or linked with, the CPU.

The central processing computer can also include an output device(s) for outputting any of the data, information, messages and/or reports, described herein as being generated by or via the central processing computer. The output device(s) can also be connected to, or linked with, the CPU.

The central processing computer can also include a video and/or audio recording device(s) which can include a camera and/or a video recording device for recording pictures or video and/or video clips and/or a microphone or an audio recording device for recording audio or audio clips which can be recorded by, and/or transmitted live, by or from the central processing computer, or which can be recorded by, and stored at or in, the central processing computer for transmission by or from the central processing computer at a later time. The video and/or audio recording device(s) can also be connected to, or linked with, the CPU.

The user communication device can be a personal computer, a home computer, a laptop computer, a notebook computer, a tablet computer, a tablet, a hand-held computer, a palmtop computer, a personal communication device, a cellular telephone, a wireless telephone, a mobile telephone, a Smartphone, a smartphone, a personal digital assistant, a digital television, an interactive television, a digital television, a telephone, a digital telephone, a television, an interactive television, a beeper, a pager, and/or a watch or a Smart watch, and/or any wearable device, computer or communication device. The user communication device 30 can also be a server computer, or any computer capable of being utilized in a network or capable of being utilized with other computers in a network.

The user communication device includes a central processing unit or CPU which can be a microprocessor. The CPU can also be a microcomputer, a minicomputer, a macro-computer, and/or a mainframe computer, depending upon the application. The user communication device also includes a random access memory device(s) (RAM), a read only memory device(s) (ROM), each of which can be connected to, or linked with, the CPU, and a user input device for inputting and/or entering data and/or information and/or instructions and/or commands into the user communication device. The input device(s) can also be connected to, or linked with, the CPU.

The user communication device can also include a display device for displaying data and/or information to a user or operator. The display device can be connected to, or linked with, the CPU. The user communication device can also include a transmitter(s) for transmitting signals and/or data and/or information to any one or more of the personal monitoring device(s), the central processing computer(s), the law enforcement communication device(s), the emergency services provider communication device(s), and/or the healthcare records computer(s), and/or any other user communication device(s), which may be utilized in conjunction with the present invention. The transmitter(s) can also be connected to, or linked with, the CPU.

The user communication device can also include a receiver(s) for receiving signals and/or data and/or information from any one or more of the personal monitoring device(s), the central processing computer(s), the law enforcement communication device(s), the emergency services provider communication device(s), and/or the healthcare records computer(s), and/or any other user communication device(s), which may be utilized in conjunction with the present invention. The receiver(s) can also be connected to, or linked with, the CPU.

The user communication device can also include a database(s) which can also be connected to, or linked with, the CPU. The user communication device can also include an output device(s) for outputting any of the data, information, and/or reports, described herein as being generated by or via the user communication device. The output device(s) can also be connected to, or linked with, the CPU.

The user communication device can also includes a video and/or audio recording device(s) which can include a camera and/or a video recording device for recording pictures or video and/or video clips and/or a microphone or an audio recording device for recording audio or audio clips which can be recorded by, and/or transmitted live, by or from the user communication device, or which can be recorded by, and stored at or in, the user communication device for transmission by or from the user communication device at a later time. The video and/or audio recording device(s) can also be connected to, or linked with, the CPU.

The user communication device can also include a "kill" switch or associated hardware and/or software for disabling and/or deactivating the user communication device in instances when same might be lost or stolen, so as to prevent its use by another person and/or to prevent any access to any data and/or information stored therein, thereby rendering the user communication device 30 useless to another person after being reported, or being discovered, as being lost or stolen.

The law enforcement communication device can be a personal computer, a home computer, a laptop computer, a notebook computer, a tablet computer, a tablet, a hand-held computer, a palmtop computer, a personal communication device, a cellular telephone, a wireless telephone, a mobile telephone, a Smartphone, a smartphone, a personal digital assistant, a digital television, an interactive television, a digital television, a telephone, a digital telephone, a television, an interactive television, a beeper, a pager, and/or a watch or a Smart watch, and/or any wearable device, computer or communication device. The law enforcement communication device 40 can also be a server computer, or any computer capable of being utilized in a network or capable of being utilized with other computers in a network.

The law enforcement communication device includes a central processing unit or CPU which can be a microprocessor. The CPU can also be a microcomputer, a minicomputer, a macro-computer, and/or a mainframe computer, depending upon the application.

The law enforcement communication device also includes a random access memory device(s) (RAM), a read only memory device(s) (ROM), each of which is also connected to, or linked with, the CPU, and a user input device for inputting and/or entering data and/or information and/or instructions and/or commands into the law enforcement communication device. The input device(s) can also be connected to, or linked with, the CPU.

The law enforcement communication device can also include a display device for displaying data and/or information to a user or operator and which can also be connected to, or linked with, CPU. The law enforcement communication device can also include a transmitter(s) for transmitting signals and/or data and/or information to any one or more of the personal monitoring device(s), the central processing computer(s), the user communication device(s), the emergency services provider communication device(s), and/or the healthcare records computer(s), and/or any other the law enforcement communication device(s) which may be utilized in conjunction with the present invention. The transmitter(s) can also be connected to, or linked with, the CPU.

The law enforcement communication device can also include a receiver(s) for receiving signals and/or data and/or information from any one or more of the personal monitoring device(s), the central processing computer(s), the user communication device(s), the emergency services provider communication device(s), and/or the healthcare records computer(s), and/or any other law enforcement communication device(s) which may be utilized in conjunction with the present invention. The receiver(s) can also be connected to, or linked with, the CPU 40A.

The law enforcement communication device can also include a database(s) which also can be connected to, or linked with, the CPU. The law enforcement communication device can also include an output device(s) for outputting any of the data, information, and/or reports, described herein as being generated by or via the law enforcement communication device(s).

The law enforcement communication device can also includes a video and/or audio recording device(s) which can include a camera and/or a video recording device for recording pictures or video and/or video clips and/or a microphone or an audio recording device for recording audio or audio clips which can be recorded by, and/or transmitted live, by or from the law enforcement communication device, or which can be recorded by, and stored at or in, the law enforcement communication device for transmission by or from the law enforcement communication device at a later time.

The emergency services provider communication device can be a personal computer, a home computer, a laptop computer, a notebook computer, a tablet computer, a tablet, a hand-held computer, a palmtop computer, a personal communication device, a cellular telephone, a wireless telephone, a mobile telephone, a Smartphone, a smartphone, a personal digital assistant, a digital television, an interactive television, a digital television, a telephone, a digital telephone, a television, an interactive television, a beeper, a pager, and/or a watch or a Smart watch, and/or any wearable device, computer or communication device. The emergency services provider communication device can also be a server computer or any other computer capable of being utilized in a network.

The emergency services provider communication device includes a central processing unit or CPU which can be a microprocessor. The CPU can also be a microcomputer, a minicomputer, a macro-computer, and/or a mainframe computer, depending upon the application. The emergency services provider communication device also includes a random access memory device(s) (RAM), a read only memory device(s) (ROM), each of can be connected to, or linked with, the CPU, and a user input device for inputting and/or entering data and/or information and/or instructions and/or commands into the emergency services provider communication device.

The emergency services provider communication device can also include a display device for displaying data and/or information to a user or operator. The display device can also be connected to, or linked with, the CPU. The emergency services provider communication device can also include a transmitter(s) for transmitting signals and/or data and/or information to any one or more of the personal monitoring device(s), the central processing computer(s), the user communication device(s), the law enforcement communication device(s), and/or the healthcare records computer(s), and/or any other emergency services provider communication device(s), which may be utilized in conjunction with the present invention. The transmitter(s) can also be connected to, or linked with, the CPU. The emergency services provider communication device(s) can also include a receiver(s), for receiving signals and/or data and/or information from any one or more of the personal monitoring device(s), the central processing computer(s), the user communication device(s), law enforcement communication device(s), and/or the healthcare records computer(s), and/or any other the emergency services provider communication device(s), which may be utilized in conjunction with the present invention. The receiver(s) can also be connected to, or linked with, the CPU.

The emergency services provider communication device can also include a database(s) which can also be connected to, or linked with, the CPU. The emergency services provider communication device can also include an output device(s) for outputting any of the data, information, and/or reports, described herein as being generated by or via the emergency services provider communication device. The output device(s) can also be connected to, or linked with, the CPU.

The emergency services provider communication device 50 can also include a video and/or audio recording device(s) which can include a camera and/or a video recording device for recording pictures or video and/or video clips and/or a microphone or an audio recording device for recording audio or audio clips which can be recorded by, and/or transmitted live, by or from the emergency services provider communication device, or which can be recorded by, and stored at or in, the emergency services provider communication device for transmission by or from the emergency services provider communication device at a later time. The video and/or audio recording device(s) can also be connected to, or linked with, the CPU.

The healthcare records computer can also be any computer or computer system, or any group of computers. The healthcare records computer can also be a personal computer, a home computer, a laptop computer, a notebook computer, a tablet computer, a tablet, a hand-held computer, a palmtop computer, a personal communication device, a cellular telephone, a wireless telephone, a mobile telephone, a Smartphone, a smartphone, a personal digital assistant, a digital television, an interactive television, a digital television, a telephone, a digital telephone, a television, an interactive television, a beeper, a pager, and/or a watch or a Smart watch, and/or any wearable device, computer or communication device. The healthcare records computer can also be server computer or any computer capable of being utilized in a network.

The healthcare records computer includes a central processing unit or CPU which can be a microprocessor. The CPU can also be a microcomputer, a minicomputer, a macro-computer, and/or a mainframe computer, depending upon the application.

The healthcare records computer can also include a random access memory device(s) (RAM), a read only memory device(s) (ROM), each of which can be connected to, or linked with, the CPU, and a user input device for inputting and/or entering data and/or information and/or instructions and/or commands into the healthcare records computer and which can also be connected to, or linked with, the CPU.

The healthcare records computer can also include a display device for displaying data and/or information to a user or operator and which an also be connected to, or linked with, the CPU. The healthcare records computer can also include a transmitter(s) for transmitting signals and/or data and/or information to any one or more of the personal monitoring device(s), the central processing computer(s), the user communication device(s), the law enforcement communication device(s), the emergency services provider communication device(s), and/or any other healthcare records computer(s), which may be utilized in conjunction with the present invention. In the preferred embodiment, the transmitter(s) can also be connected to, or linked with, the CPU. The healthcare records computer can also include a receiver(s) for receiving signals and/or data and/or information from any one or more of the personal monitoring device(s), the central processing computer(s), the user communication device(s), the law enforcement communication device(s), the emergency services provider communication device(s), and/or any other healthcare records computer(s), which may be utilized in conjunction with the present invention. In the preferred embodiment, the receiver(s) can also be connected to, or linked with, the CPU. The healthcare records computer can also include a database(s) which can also be CPU.

The healthcare records computer can also include an output device(s) for outputting any of the data, information, and/or reports, described herein as being generated by or via the healthcare records computer which can also be connected to, or linked with, the CPU.

The healthcare records computer can also include a video and/or audio recording device(s) which can include a camera and/or a video recording device for recording pictures or video and/or video clips and/or a microphone or an audio recording device for recording audio or audio clips which can be recorded by, and/or transmitted live, by or from the healthcare records computer, or which can be recorded by, and stored at or in, the healthcare records computer for transmission by or from the healthcare records computer at a later time. The video and/or audio recording device(s) can also be connected to, or linked with, the CPU.

The apparatus and method of the present invention can be utilized to monitor an individual or individuals of any age and, therefore, can be utilized to monitor any child, infant, teenager or young adult, adult of any age, and/or elderly individual. The apparatus and method of the present invention can also be utilized to monitor any child, infant, teenager or young adult, adult of any age, and/or elderly individual, who may or may not be inflicted with a condition, illness, or disease, or who may or may not be inflicted with autism, Alzheimer's disease, memory loss, or be ill with any temporary or permanent illness, sickness, disease, or condition. The apparatus and method of the present invention can also be utilized to monitor any child, infant, teenager or young adult, adult of any age, and/or elderly individual, as a safety precaution.

Any user or individual who utilizes a personal monitoring device, or who has a personal monitoring device assigned to him or her, or who has a personal monitoring device associated with him or her, can be referred to herein, or can be defined herein as being, a "monitored individual". Any user or individual who utilizes a user communication device to monitor a monitored individual can be referred to herein, or can be defined herein as being, a "monitoring individual".

It is envisioned that any personal monitoring device can be programmed with, or can have stored therein or therewith, information regarding the monitored individual's home address, residence address, school residence address or place, workplace address, or other address, place, or location, which is considered to be that monitored individual's place of safety or "home base" or "safe location". It is also envisioned that any personal monitoring device can be programmed with, or have stored therein or therewith, information regarding any address(es), place(s), or location(s), to which the monitored individual typically travels on a daily basis. For example, the personal monitoring device 10 can be programmed with, or have stored therein or therewith, information regarding the monitored individual's school address, place, or location, workplace address, place, or location, employment address, place, or location, activity or event address, place, or location, or any other address, place, or location, to which the monitored individual is known to travel on a weekday basis, on a weekend daily basis, or on any daily basis.

The personal monitoring device can also be programmed with the monitored individual's travel itineraries and/or travel schedules for traveling to and between one address, place, or location to another address, place, or location. The personal monitoring device can also be programmed with travel routes or directions for traveling to and between one address, place, or location to another address, place, or location. The personal monitoring device can also be programmed with software programs, navigation programs, or any algorithms or software applications, for identifying, determining, ascertaining, or calculating, any travel routes or directions for traveling to and between one address, place, or location to another address, place, or location.

The personal monitoring device an be utilized in connection with, or in conjunction with, the apparatus, the central processing computer, a user communication device associated with, or used by, any user or individual authorized to, or assigned to, monitor the monitored individual, any law enforcement communication device, and/or any emergency services provider communication device. The personal monitoring device can also be utilized as a stand-alone device by the monitored individual to allow the monitored individual to monitor his or her travels, whereabouts, or environment.

The personal monitoring device can be activated to operate so as to determine, ascertain, and/or monitor, a monitored individual's location or whereabouts. Depending upon the time of the particular day and the schedule of the monitored individual, the personal monitoring device can determine the monitored individual's position or location and can determine such to be at an address, place, or location, where the monitored individual should be at that particular time.

The personal monitoring device can also detect the movements of a monitored individual and can identify a travel route for the monitored individual. The personal monitoring device can also detect when a monitored individual has deviated from a travel route, or has gone off course from a travel route. Upon detecting that the monitored individual has deviated from the travel route, or has gone off course from the travel route, the personal monitoring device can perform any one or more of a number of functions in response to the detection of the monitored individual deviating from the travel route.

The personal monitoring device can generate a travel route deviation message which can contain and/or include the time and/or place, position, or location, when and/or where the monitored individual deviated from or left the travel route and the monitored individual's current place, position, or location. The travel route deviation message can also include information regarding the portion of the monitored individual's itinerary associated with the travel route from which the monitored individual has deviated The personal monitoring device can also obtain, determine, read, or record, any physiological or healthcare information regarding the monitored individual such as, for example, but not limited to, the monitored individual's heart rate, pulse rate, blood pressure, body temperature, blood sugar level, or any other healthcare information or healthcare-related data and/or information, or any other physical condition, physiological condition, or healthcare condition, which can be measured or measurable by any wearable device or by any implanted device or implantable device which can be obtained by or using any of the respective and herein-described devices, equipment, monitors, or measurement devices, which can be wearable or non-wearable and/or which can be connected to or with, or wirelessly linked to or with the personal monitoring device. Any data and/or information obtained regarding any of the herein-described data and/or information can also be included in the travel route deviation message.

The travel route deviation message can also contain and/or include the temperature of the environment in which the monitored individual is located, which can be exterior temperature if the monitored individual and the personal monitoring device is located outdoors, or an interior temperature if the monitored individual and the personal monitoring device are located indoors.

The personal monitoring device can also automatically transmit the travel route deviation message to the user communication device which is used by, associated with, or assigned to, the monitoring individual for the monitored individual. The personal monitoring device can also generate and transmit updated travel route deviation messages at any pre-determined or pre-selected time intervals.

Travel route deviation messages can also be transmitted from the personal monitoring device to the central processing computer, so as to report the monitored individual's travel route deviation to the central processing computer and to any company or entity which operates same. The personal monitoring device can also automatically transmit the travel route deviation message to the law enforcement communication devices of or associated with each law enforcement agency or department associated with the city, town, municipality, or political subdivision, in which the monitored individual was detected as having deviated from the travel route, as well as to each law enforcement communication device(s) of or associated with any neighboring cities, towns, municipalities, or political subdivisions. The personal monitoring device can also automatically transmit the travel route deviation message to the emergency services provider communication device of or associated with the emergency services provider agency or department of or for the city, town, municipality, or political subdivision, in which the monitored individual was detected as having deviated from the travel route, as well as to each emergency services provider communication device of or associated with any neighboring cities, towns, municipalities, or political subdivisions.

The personal monitoring device can also initiate a cellular or wireless telephone call to the user communication of the monitoring individual. If more than one monitoring individuals are associated with the monitored individual, then the personal monitoring device can initiate a cellular or wireless telephone call, and/or a telephone conference call, to and/or so as to include the monitored individual and all monitoring individuals for the monitored individual. The personal monitoring device can also initiate a cellular or wireless telephone call, and/or a telephone conference call, to and/or so as to include at least one monitoring individual and a law enforcement officer or individual, via and/or by including a respective law enforcement communication device, and/or an emergency services provider individual or person via and/or by including an emergency services provider communication device.

The cellular or wireless telephone call can be made so as to put the monitored individual into live contact with, and/or into live communication with, the monitoring individual or monitoring individuals, and/or so as to put the monitored individual and the monitoring individual or monitoring individuals into live contact with, and/or into live communication with, law enforcement personnel and/or emergency services personnel.

Once the cellular or wireless telephone call and/or any conference line involving the monitoring individual or monitoring individuals, and/or any law enforcement law enforcement personnel and/or emergency services personnel, has been made and, with the call line and/or conference line being live and/or on-going, the personal monitoring device can de-activate the personal monitoring device's telephone call on/off switch, or on/off switch functionality, on or in the personal monitoring device so that the personal monitoring device cannot be disconnected from the telephone call and/or the conference line. Any herein-described de-activation of the telephone call on/off switch, or on/off switch functionality, of the personal monitoring device can be effectuated by using, and/or by programming the personal monitoring device, with or using any appropriate and/or suitable software program, algorithm, or software application. The personal monitoring device can also be programmed and/or equipped so as to detect being disconnected from, or dropped from, the telephone call and/or conference call, and can automatically re-connect to the telephone call and/or to the conference call. Any of the herein-described personal monitoring device(s), user communication device(s), law enforcement communication device(s), and/or an emergency services provider communication device(s), can be equipped with long lasting batteries or power sources, external batteries or power sources, and/or any other supplemental batteries or power sources, so as to ensure that sufficient electrical power is available and can be supplied to any of the herein-described personal monitoring device(s), user communication device(s), law enforcement communication device(s), and/or an emergency services provider communication device(s).

The herein-described functionality of establishing a cellular or wireless telephone call, and/or conference call, can allow the monitored individual to be brought into, and to be maintained in, live contact with and/or live communication with, his or her monitoring individual or one or more monitoring individuals, and/or with any number of law enforcement personal and/or emergency services personnel. In this manner, the monitoring individual or monitoring individuals, and/or any law enforcement personnel and/or emergency services personnel, can speak with the monitored individual, can comfort or reassure the monitored individual that all will be okay, and/or can ascertain the monitored individual's whereabouts, while the monitored individual my be lost or off track. The personal monitoring device can also activate a speakerphone, and/or any speakers and/or microphone, of same for and/or during the cellular or wireless telephone call and/or conference call.

The personal monitoring device can also activate any camera, any video recording device or equipment, any microphone, or any audio recording device, of same, and/or any device or equipment of the video and/or audio recording device(s) of same, for and/or during the cellular or wireless telephone call and/or conference call.

The personal monitoring device can activate one or more indicator lights on the personal monitoring device which can be used to indicate that the monitored individual is outside of his or her "safe" zone of travel as well as indicate when the monitored individual is inside or within his or her "safe" zone.

The personal monitoring device can also activate any camera, any video recording device or equipment, any microphone, or any audio recording device, of same, and/or any device or equipment of the video and/or audio recording device(s) of same, for obtaining pictures, video information, video clips, audio information, or audio clips, of the monitored individual, or any individual's or person who or may come into contact with the monitored individual, and/or of any of the monitored individual's surroundings, environment, or location. Any pictures, video information, video clips, audio information, or audio clips, recorded by and at the personal monitoring device can be transmitted to, and stored by or in, each of the user communication device of the monitoring individual, each user communication device of each monitoring individual, the central processing computer, or any law enforcement communication device(s), and/or an emergency services provider communication device(s).

The personal monitoring device can also track the monitored individual's movements and can generate tracking update messages at any pre-selected time interval(s), containing information regarding the monitored individual's location(s), movement(s), and speed of travel or movement. The personal monitoring device, as well as the central processing computer(s), the user communication(s), the law enforcement communication device(s), and/or the emergency services provider communication device(s), can be equipped with software to calculate or otherwise determine the monitored individual's speed of movement. In this manner, depending on the speed of movement of the monitored individual, it can be determined if the monitored individual is traveling in or on a vehicle or is traveling on foot. The tracking update messages can be automatically transmitted, at periodic time intervals, from the personal monitoring device to the user communication(s) of the monitoring individual(s), and/or, or as well as, to the central processing computer(s), the user communication(s), the law enforcement communication device(s), and/or the emergency services provider communication device(s).

Information regarding the monitored individual's movement can be displayed and/or tracked on or via a digital or satellite map which can be displayed on the display device of the respective user communication(s), the central processing computer(s), the law enforcement communication device(s), and/or the emergency services provider communication device(s). Information regarding the monitored individual's movement can also be displayed and/or tracked on or via a digital or satellite map which can be displayed on the display screen of the personal monitoring device.

The personal monitoring device can also activate a homing beacon or beacon of the personal monitoring device. The homing beacon or beacon of the personal monitoring device can transmit or provide a signal, a distress signal, or any other indication, which can be utilized in connection with a corresponding receiver to track and/or to "home" in on or locate the monitored individual.

The personal monitoring device can also play any prerecorded messages or video clips or audio clips, which messages, video clips, or audio clips, to the monitored individual via the display screen and speakers. The personal monitoring device can also provide information, and/or a link to information, regarding or contained in the healthcare records of the monitored individual. The personal monitoring device can also provide information regarding any instructions or directions for guiding the monitored individual back onto his or her travel route.

At any time, the user communication device, or any user or operator of any other computer or communication device described herein, can generate and/or can transmit a control signal to the personal monitoring device in order to enable, disable, activate, de-activate, control an operation of, or monitor an operation of, the personal monitoring device and/or any component, system, device, or equipment, of same.

A personal monitoring account can be created or established for any monitored individual with whom the apparatus and method of the present invention can be utilized.

The operation of the apparatus of the present invention and/or the personal monitoring device can also be triggered by, or can be activated by or in response to the actions of, a monitoring individual. A monitoring individual can utilize a software application or a software "app" in order to determine the position or location of the monitored individual. The software application or software "app" can be capable of determining the position or location of the monitored individual at any time and/or on demand by the monitoring individual. The monitoring individual can also perform a "pinging" operation in order to utilize a communications services provider or any other suitably equipped entity in order to "ping" or determine the position or location of the monitored individual. If the monitored individual is determined to be at an unexpected or unapproved place or location, or has deviated from an appropriate travel route at that point or instant in time, the monitoring individual can activate the apparatus and can utilize same to find or locate, or otherwise provide assistance to, the monitored individual.

The apparatus of the present invention and/or the personal monitoring device can also be utilized to record information regarding any incidents of bullying, harassment, criminal acts, or any other activities or events, perpetrated on, inflicted upon, or occurring involving the monitored individual and/or occurring in the vicinity of the monitored individual. The personal monitoring device can be activated to record audio information and/or video information regarding the event or the occurrence, the position or location of same, date and time of same, and/or any other pertinent information regarding same which can be obtained by, with, or using, the personal monitoring device. A monitored individual can manually activate the personal monitoring device and/or the personal monitoring device can be equipped with voice activation equipment and/or hardware and/or software and can be activated to record any information regarding an event or occurrence by, or in response to, a voice activation command. Any data and/or information recorded can be stored in the database of the personal monitoring device and/or can be transmitted to the user communication device(s) of or associated with the monitoring individual, the central processing computer, and/or to any one of more law enforcement communication devices and/or emergency services provider communication devices, for reporting and for storing as evidence.

The apparatus and method of the present invention can be utilized in order to provide and support comprehensive personal monitoring services of a global nature for individuals of any age. The apparatus and method of the present invention can also be utilized in order to provide and support comprehensive personal monitoring services of a global nature for individuals of any age and regardless of whether or not they have any conditions, illnesses, sicknesses, disabilities, or health conditions. The present invention can also be utilized to provide and service personal monitoring accounts for any number of individuals, with such personal monitoring accounts facilitating the providing of personal monitoring services by and/or involving any number of various monitoring services providers, security services provider, healthcare providers, healthcare insurers, healthcare records service providers, and/or healthcare payers, and/or law enforcement agencies and/or departments, and/or emergency services providers agencies and/or departments.

DESCRIPTION OF THE PREFERRED EMBODIMENTS

Figure 1:
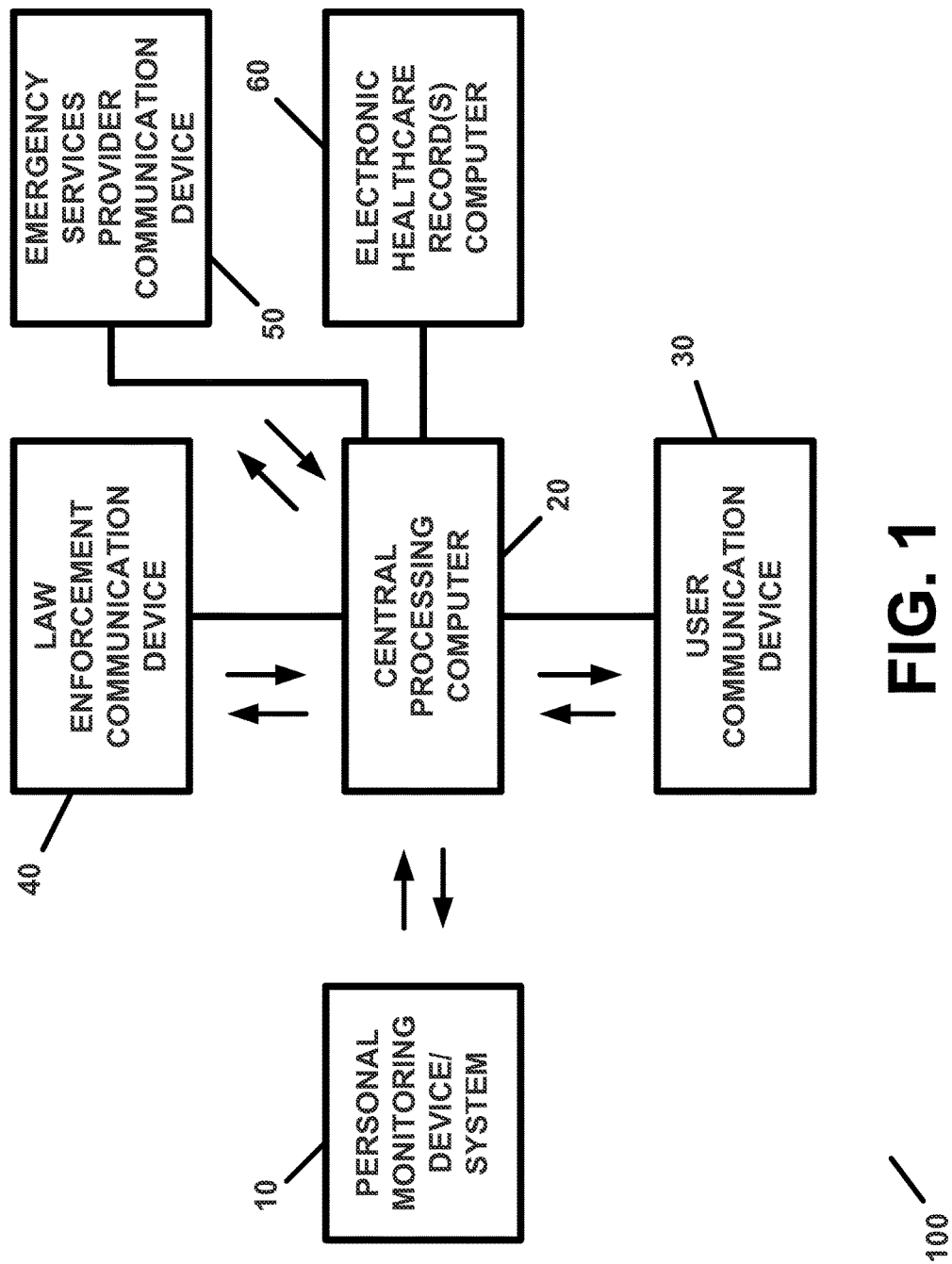
FIG. 1 illustrates the apparatus of the present invention, in block diagram form.

The present invention pertains to a personal monitoring apparatus and method and, in particular, to a personal monitoring apparatus and method which can be utilized to monitor infants, children, the elderly, or individuals of any and./or all ages, and/or to monitor their position or location, their whereabouts, their surroundings, their vital signs, their physiological measurements, states, or condition, and/or any individual and/or individuals with whom they may come into contact.

The present invention can provide an apparatus and method which can be utilized to monitor and/or to track the whereabouts and/or travels of an individual at any time, to compare an individual's current whereabouts to their current location or a location where they should be, ought to be, or are expected to be, and/or to provide an alert, or to provide a notification, to the individual, a parent of the individual, a child of the individual, a relative of the individual, a caregiver of the individual, an employer of the individual, a law enforcement agency or law enforcement personnel, emergency services personnel, a third party, or any other person or entity, when the individual is located at a location where they should not be, wherein they ought not be, where they are not expected to be, or when they have deviated from, or are deviating from, a planned, an expected, or a desired, travel route, or a planned, expected, or desired, schedule when they itinerary.

For example, the apparatus and method or the present invention can be used to monitor the whereabouts, the location, or the travel, of a child of any age, a child having special needs, a child who has become injured or ill, or a child who has become lost, mission, or who has become a victim of foul play. As and for another example, the apparatus and method or the present invention can be used to monitor the whereabouts, the location, or the travel, of an adult or an elderly individual of any age, an adult or an elderly individual having special needs, an adult or an elderly individual who has become ill or injured, or an adult or an elderly individual who has become lost, mission, or who has become a victim of foul play.

The apparatus and method of the present invention can also be utilized to provide information or an indication, to the individual or to any persons with whom the individual may come into contact, which can provide information indicative of the individual being where he or she should not be, indicative that the individual is lost, indicative that the individual is or might be injured or ill, or indicative that the individual is in need of help or assistance.

The apparatus and method of the present invention can also be utilized to provide information or an indication, to a parent of the individual, to a child of the individual, to a relative of the individual, to a caregiver of the individual, to an employer of the individual, to a law enforcement agency or law enforcement personnel, to an emergency services personnel, to any third party, or to any other person or entity, when the individual has been determined to be lost, injured, ill, or otherwise in need of help or assistance.

The apparatus and method of the present invention can also be utilized to obtain, record, store, and/or provide, healthcare information or physiological data and/or information, or any other information regarding the state or status of an individual, including, but not limited to, the individual's heart rate, blood pressure, body temperature, blood sugar level, or any other physical condition, physiological condition, or healthcare condition, which can be measured or measurable by any wearable device or by any implanted device or implantable device.

The apparatus and method of the present invention can also be utilized to initiate, establish, and/or maintain, a communication link, or a telephone call, with and between any of the herein-described personal monitoring devices with and any of the herein-described user communication devices, central processing computers, and/or law enforcement communication devices and/or emergency services communication devices. In this regard, for example, a line communication can be established with and/or between the personal monitoring device of a lost, mission, or ill, child's and a user communication device of, associated with, or used by, the child's parent, relative, caregiver, or other authorized person. The apparatus and method of the present invention can also be utilized to provide an open, and speakerphone-operated, line of communication with the personal monitoring device so that a respective parent, relative, caregiver, or other authorized person can, using a user communication device, speak to, or engage in conversation with, the child or with any individual with whom the child comes into contact so as to facilitate finding the child, helping the child find help of his or her way back to a safe location, and/or making sure that the child is brought to a place of safety and/or is safely returned home or to another safe location, and/or to make sure that the child's needs are provided for until being reunited with his or her parent(s), a caregiver, or law enforcement. The apparatus and method of the present invention can also be utilized in a same, a similar, or an analogous, manner in providing personal monitoring for adults and elderly individuals of any age.

The apparatus and method of the present invention can also be utilized in order to establish, and to provide services for, personal monitoring accounts for individuals. In a preferred embodiment, a personal monitoring account can be assigned to an individual in order to provide any number or monitoring services for that individual. For example, a personal monitoring account can be utilized to allow any other authorized individual, person, or entity, to monitor, and/or to track location, position, or movement of, an individual, to communicate with the individual at any time, to communicate with people in the vicinity of the individual, to obtain information regarding the position, location, or whereabouts of the individual, persons with whom the individual may be in contact with, or may have come into contact with, the individual's itinerary, travels, to obtain video and/or audio information regarding the individual, his or her travels, locations, and/or any other information regarding the individual. In a preferred embodiment, one or more personal monitoring accounts can be set up by or for an individual. In this regard, an individual can have one personal monitoring account ("PMA") or a plurality of personal monitoring accounts.

As will be described herein, the apparatus and method of the present invention can be utilized to provide a number of various features and functionality which can be useful in providing personal monitoring services and operations for infants, children, and adults, of any ages. The apparatus and method of the present invention can also be utilized to provide personal monitoring services and operations for and regarding pets and animals of any type or kind.

Applicant hereby incorporates by reference herein the subject matter and teachings of U.S. Provisional Patent Application Ser. No. 62/085,587, filed Nov. 30, 2014, and entitled "PERSONAL MONITORING APPARATUS AND METHOD", the subject matter and teachings of which are hereby incorporated by reference herein in their entirety.

FIG. 1 illustrates the apparatus of the present invention, in block diagram form. The apparatus of the present invention is denoted generally by the reference numeral 100. In the preferred embodiment, the apparatus 100 of the present invention includes a personal monitoring device 10. In the preferred embodiment, the personal monitoring device is, or can be, a cellular telephone, a mobile telephone or wireless telephone, a Smartphone, a personal digital assistant, or any other suitable device.

In a preferred embodiment, the personal monitoring device 10 can be equipped with the communication equipment typically found in cellular telephones, mobile telephones or wireless telephones, Smartphones, personal digital assistants, or any other suitable devices, for facilitating a two-way communication with other individuals or entities and/or with communications devices, computers, equipment, or any other communication equipment used by any individuals or entities. In a preferred embodiment, the personal monitoring device 10 can also be equipped with global positioning system (GPS) device or equipment. In another preferred embodiment, the personal monitoring device 10 can also be equipped with navigation equipment such as are typically found in commercially available GPS navigation devices and equipment which are used to assist motorists and individuals traveling in motor vehicles in navigating from a location to a destination.

In a preferred embodiment, the personal monitoring device 10 can also be equipped with global positioning system (GPS) equipment and navigation equipment which can allow the personal monitoring device 10 to act in a stand-alone manner, without having to obtain any navigation information from any external device or computer. In another preferred embodiment, the personal monitoring device 10 can be equipped to receive, and provide to a user, navigation data and/or information, including, but not limited to, navigation instructions, which is obtained from an external computer or communication device or a service provider computer or communication device.

The personal monitoring device 10 can also be any communication device, computer, personal computer, laptop computer, notebook computer, Smartphone or smartphone, smart telephone, cellular telephone, personal digital assistant, tablet, tablet computer, watch, smart watch, or wearable device or computer, an implantable device or computer, an item of jewelry, eyeglasses, or any accessory, or any combination of same, or any equivalent of same, which can be utilized by any person, individual, or entity, who or which utilizes the apparatus 100 and method of the present invention. The personal monitoring device 10 can also be a server computer, a mainframe computer, a mini-computer, a microcomputer, or any other computer or device for suiting the needs of the particular user.

Any number of personal monitoring devices 10 can be utilized by or in conjunction with the apparatus 100 of the present invention. The personal monitoring device 10 can communicate, in a bi-directional manner and/or otherwise, with and/or can operate in conjunction with any the herein-described computers, communication devices, and/or computer systems described herein as being utilized in connection with the apparatus 100 and method of the present invention.

In the preferred embodiment, the apparatus 100 of the present invention includes a central processing computer or central processing computer system 20 (hereinafter referred to as the "central processing computer 20"). In the preferred embodiment the central processing computer 20 can be any computer or computer system or can be a computer with operated in a network with other computers or a server computer.

In the preferred embodiment, the central processing computer 20 can provide control over the apparatus 100 and can perform any of the various processing services and/or functions described herein as being performed by same. The central processing computer 20 can be a single computer or a system of computers and/or can include a plurality of computers or computer systems which are utilized in conjunction with one another. The central processing computer 20, in the preferred embodiment, can provide personal monitoring services for or regarding any number of individuals and/or entities and/or can provide personal monitoring services for or regarding any number of individuals and/or entities who or which need, want, or desire, to monitor, to monitor the whereabouts of, and/or who or which desire to be notified regarding the whereabouts, location, healthcare status, or any occurrence of or regarding any event which may give rise to a need to find, locate, and/or monitor a location of, any child, adult, elderly person, or any individual of any age.

Any number of central processing computers 20 can be utilized by or in conjunction with the apparatus 100 of the present invention. The central processing computer(s) 20 can communicate, in a bi-directional manner and/or otherwise, with, and/or can operate in conjunction with, the personal monitoring device 10 and/or any of the other communication devices, computers, and/or computer systems, associated with or used by any of the individuals and/or entities who or which utilize the apparatus 100 and method of the present invention.

The apparatus 100 also includes a user communication device or computer 30 (hereinafter referred to as "user communication device 30" or "user computer 30") which is associated with, or which can be used by, any one or more of any of the herein-described users, individuals, or entities, who or which utilize the apparatus 100 and method of the present invention.

Any number of user communication devices 30 can be utilized by or in conjunction with any user or any individual or entity who or which utilizes the apparatus 100 and method of the present invention, and any number of user communication devices 30 can be utilized in conjunction with the apparatus 100 and method of the present invention.

The user communication device(s) 30 can communicate, in a bi-directional manner and/or otherwise, with, and/or can operate in conjunction with the personal monitoring device 10 and/or the central processing computer 20 and/or any of the other herein-described communication devices, computers, and/or computer systems, associated with or used by any of the individuals and/or entities who or which utilize the apparatus 100 and method of the present invention.

The apparatus 100 also includes a law enforcement communication device or computer 40 (hereinafter referred to as "law enforcement communication device 40" or "law enforcement computer 40") which is associated with, or which can be used by, any law enforcement agency or department which utilize the apparatus 100 and method of the present invention.

Any number of law enforcement communication devices 40 can be utilized by or in conjunction with any law enforcement agency or department which utilizes the apparatus 100 and method of the present invention, and any number of law enforcement communication devices 40 can be utilized in conjunction with the apparatus 100 and method of the present invention.

The law enforcement communication device(s) 40 can communicate, in a bi-directional manner and/or otherwise, with, and/or can operate in conjunction with the personal monitoring device 10, the central processing computer 20, the user communication device 30, and/or any of the other herein-described communication devices, computers, and/or computer systems, associated with or used by any of the individuals and/or entities who or which utilize the apparatus 100 and method of the present invention.

The apparatus 100 also includes an emergency services provider communication device or computer 50 (hereinafter referred to as an "emergency services provider communication device 50" or "emergency services provider computer 50") which is associated with, or which can be used by, any emergency services provider, agency, or department, which utilizes the apparatus 100 and method of the present invention.

Any number of emergency services provider communication devices 50 can be utilized by or in conjunction with any emergency services provider, agency, or department, which utilizes the apparatus 100 and method of the present invention, and any number of emergency services provider communication devices 50 can be utilized in conjunction with the apparatus 100 and method of the present invention.

The emergency services provider communication device(s) 50 can communicate, in a bi-directional manner and/or otherwise, with, and/or can operate in conjunction with the personal monitoring device 10, the central processing computer 20, the user communication device 30, the law enforcement communication device 40, and/or any of the other herein-described communication devices, computers, and/or computer systems, associated with or used by any of the individuals and/or entities who or which utilize the apparatus 100 and method of the present invention.

The apparatus 100 can also include a healthcare records computer or communication device 60 (hereinafter referred to as "healthcare records computer 60") which, in a preferred embodiment, stores an electronic healthcare record or electronic healthcare records for any of the herein-described individuals who or which can be monitored using the apparatus 100 and method of the present invention. In a preferred embodiment, the healthcare records computer 60 can also store healthcare records of any individual, children, adults, elderly persons, or any individual of any age, who is to be monitored by and using the apparatus 100 and method of the present invention as well as any healthcare records of, for, or regarding, any relatives of any of these individuals.

In a preferred embodiment, the healthcare records computer 60 or computers can serve to store and house an electronic healthcare record or any number of electronic healthcare records. The healthcare records computer 60 can also be utilized to facilitate cloud storage of any electronic healthcare record(s).

The healthcare records computer(s) 60 can communicate, in a bi-directional manner and/or otherwise, with, and/or can operate in conjunction with, the personal monitoring device 10, the central processing computer 20, the user communication device 30, the law enforcement communication device 40, the emergency services provider communication device 50, and/or any of the other communication devices, computers, and/or computer systems, associated with or used by any of the individuals and/or entities who or which utilize and/or operate in conjunction with the apparatus 100 of the present invention.

In the preferred embodiment, any of the personal monitoring device(s) 10, the central processing computer(s) 20, the user communication device(s) 30, the law enforcement communication device(s) 40, the emergency services provider communication device(s) 50, and/or the healthcare records computer(s) 60, can be any computer or communication device, including, but not limited to, a personal computer, a home computer, a server computer, or any computer capable of being utilized in a network or capable of being utilized with other computers in a network, or a hand-held computer, a palmtop computer, a laptop computer, a personal communication device, a cellular telephone, a wireless telephone, a mobile telephone, a digital television, an interactive television, a digital television, a personal digital assistant, a telephone, a digital telephone, a television, an interactive television, a beeper, a pager, and/or a watch or a Smart watch, and/or any wearable device, computer or communication device.

Each of the personal monitoring device(s) 10, the central processing computer(s) 20, the user communication device(s) 30, the law enforcement communication device(s) 40, the emergency services provider communication device(s) 50, and/or the healthcare records computer(s) 60, can transmit information to, as well as receive information from, any of the computers or communication devices 10, 20, 30, 40, 50, and/or 60 described herein. In this regard, each of the computers or communication devices 10, 20, 30, 40, 50, and/or 60, can communicate with, process information from, and/or share data and/or information with, each other and/or any other computer(s) or communication device(s) 10, 20, 30, 40, 50, and/or 60, described herein and/or utilized in conjunction with the apparatus 100 of the present invention. In this manner, any of the respective computer(s) or communication device(s) 10, 20, 30, 40, 50, and/or 60, can communicate with any other computer(s) or communication device(s) 10, 20, 30, 40, 50, and/or 60, in a bi-directional manner.

In the preferred embodiment, the present invention is utilized on, over, and/or via, the Internet and/or the World Wide Web and/or on any wireless communication network and/or any cellular communication network. The present invention, in the preferred embodiment, can also utilize wireless Internet and/or World Wide Web services, equipment and/or devices. The central processing computer(s) 20, in the preferred embodiment, has a web site or web sites associated therewith. Each of the other computers or communication devices described herein can also have a web site or web sites associated with same.

Although the Internet and/or the World Wide Web is a preferred communication system and/or medium utilized, the present invention, in any and/or all of the embodiments described herein, can also be utilized with any appropriate communication network or system including, but not limited to, a telecommunication network or system, a telephone communication network or system, a cellular communication network or system, a wireless communication network or system, a line or wired communication network or system, a wireless Internet network or system, a wireless World Wide Web network or system, a digital communication network or system, a personal communication network or system, a personal communication services (PCS) network or system, a satellite communication network or system, a broad band communication network or system, a low earth orbiting (LEO) satellite network or system, a public switched telephone network or system, a telephone communication network or system, a radio communication network or system, a cable television network or system, and/or any other communication network or system, and/or any combination of the above communication networks or systems.

Any of the personal monitoring device(s) 10, the central processing computer(s) 20, the user communication device(s) 30, the law enforcement communication device(s) 40, the emergency services provider communication device(s) 50, and/or the healthcare records computer(s) 60, can communicate with one another, and/or be linked to one another, over or via any communication network, telecommunication network, telephone network, a line-connected network, and/or a wireless communication network, and/or the Internet and/or the World Wide Web. Each of the computers or communication devices 10, 20, 30, 40, 50, and 60, can be linked with any other computer or computers directly or indirectly with one another so as to facilitate a direct or indirect bi-directional communication between said respective computers or communication devices. Communications between each of the computers or communication devices 10, 20, 30, 40, 50, and 60, can also involve an e-mail server or e-mail servers in those instances when e-mails are described as being used to transmit or to send any of the information, signals, messages, reports, notification messages, or any other communications, described herein, by or between any of the computers or communication devices 10, 20, 30, 40, 50, and 60, or when any of the information, signals, messages, reports, notification messages, or any other computers or communications, described herein, are transmitted by and/or between any of the parties described herein and/or by or between any of the computers or communication devices 10, 20, 30, 40, 50, and 60, or any other computers or communication devices, computer systems, communication network equipment, server computers, etc., or any other devices used or needed, in order to facilitate communications or the transmission of any of the herein-described information, signals, messages, reports, notification messages, or any other communications.

In a preferred embodiment, each of the personal monitoring device(s) 10, the central processing computer(s) 20, the user communication device(s) 30, the law enforcement communication device(s) 40, the emergency services provider communication device(s) 50, and/or the healthcare records computer(s) 60, can communicate in a bi-directional manner with, and/or can send and/or receive signals, data, information, messages, reports, notification messages, alerts, or any other communications or electronic communication transmissions, to, from and/or between, any other, or any number of, other personal monitoring device(s) 10, the central processing computer(s) 20, the user communication device(s) 30, the law enforcement communication device(s) 40, the emergency services provider communication device(s) 50, and/or the healthcare records computer(s) 60.

In a preferred embodiment, each of the personal monitoring device(s) 10, the central processing computer(s) 20, the user communication device(s) 30, the law enforcement communication device(s) 40, the emergency services provider communication device(s) 50, and/or the healthcare records computer(s) 60, can be linked to or with any other personal monitoring device(s) 10, the central processing computer(s) 20, the user communication device(s) 30, the law enforcement communication device(s) 40, the emergency services provider communication device(s) 50, and/or the healthcare records computer(s) 60, via a wired link or line or a wireless link.

In a preferred embodiment, each of the personal monitoring device(s) 10, the user communication device(s) 30, the law enforcement communication device(s) 40, the emergency services provider communication device(s) 50, and/or the healthcare records computer(s) 60, can be connected with, or linked to or with, the central processing computer(s) 10 as shown in FIG. 1.

In a preferred embodiment, any and/or all of the signals, data, information, messages, reports, notification messages, or any other communications, described herein as being transmitted from one device, computer, or communication device, to another device, computer, or communication device, can be, or can be included in, or can be attached to, an e-mail message, an instant messaging message, an electronic transmission, or an electronic data transmission or electronic data interchange, or can be transmitted via any other data or information transmission, and/or can be transmitted via or using any appropriate or necessary computer(s) or device(s).

In the preferred embodiment, each of the personal monitoring device(s) 10, the central processing computer(s) 20, the user communication device(s) 30, the law enforcement communication device(s) 40, the emergency services provider communication device(s) 50, and/or the healthcare records computer(s) 60, can transmit data and/or information using TCP/IP, as well as any other Internet and/or World Wide Web, and/or communication, protocols.

The apparatus 100 of the present invention can utilize electronic commerce technologies and security methods, techniques and technologies, including any encryption or security technologies and/or techniques, in any and/or all of the instances of data and/or information processing, and/or data and/or information transmission described herein.

Figure 2:
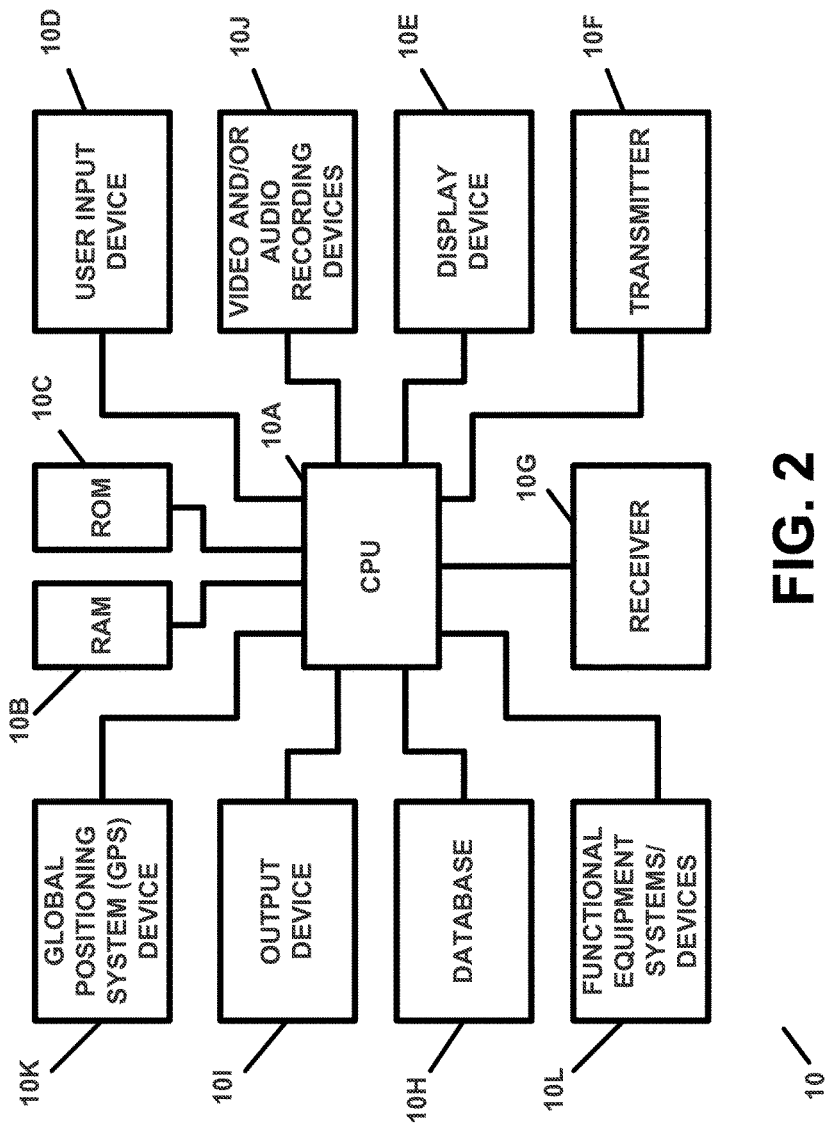
FIG. 2 illustrates the personal monitoring device of FIG. 1, in block diagram form.

FIG. 2 illustrates the personal monitoring device 10 of FIG. 1, in block diagram form. In a preferred embodiment, the personal monitoring device 10 can be a cellular telephone, a wireless telephone, a mobile telephone, a Smartphone, a smartphone, or a personal digital assistant, or the personal monitoring device 10 can be or can be a component of a personal computer, a home computer, a laptop computer, a notebook computer, a tablet computer, a tablet, a hand-held computer, a palmtop computer, a personal communication device, a cellular telephone, a wireless telephone, a mobile telephone, a Smartphone, a smartphone, a personal digital assistant, a digital television, an interactive television, a digital television, a telephone, a digital telephone, a television, an interactive television, a beeper, a pager, and/or a watch or a Smart watch, and/or any wearable device, computer or communication device. The personal monitoring device 10 can also be a server computer, or any computer capable of being utilized in a network or capable of being utilized with other computers in a network.

The personal monitoring device 10 can also be any communication device, computer, personal computer, laptop computer, notebook computer, Smartphone or smartphone, smart telephone, cellular telephone, personal digital assistant, tablet, tablet computer, watch, smart watch, or wearable device or computer, an implantable device or computer, an item of jewelry, eyeglasses, or any accessory, or any combination of same, or any equivalent of same.

With reference to FIG. 2, in the preferred embodiment, the personal monitoring device 10 includes a central processing unit or CPU 10A, which in the preferred embodiment, is a microprocessor. The CPU 10A can also be a microcomputer, a minicomputer, a macro-computer, and/or a mainframe computer, depending upon the application.

The personal monitoring device 10 also includes a random access memory device(s) 10B (RAM), a read only memory device(s) 10C (ROM), each of which is connected to, or linked with, the CPU 10A, and a user input device 10D, for inputting and/or entering data and/or information and/or instructions and/or commands into the personal monitoring device 10, which can include any one or more of a keyboard, a scanner, a user pointing device, such as, for example, a mouse, a stylus, a touch pad, and/or an audio input device, a microphone, an audio recording device, and/or a video input device, a camera or any number of cameras, a video recording device, and/or any device, electronic and/or otherwise, which can be utilized for inputting and/or entering data and/or information and/or instructions and/or commands into the personal monitoring device 10.

The input device(s) 10D is/are also connected to, or linked with, the CPU 10A. In a preferred embodiment, the input device(s) 10D can also be or can include a pulse rate monitor or measurement device or equipment, a heart rate monitor of measurement device or equipment, a blood sugar monitor or measurement device or equipment, a blood pressure monitor or measurement device or equipment, a blood alcohol monitor or measurement device or equipment, a pacemaker, a defibrillator, a thermometer measuring an individual's body temperature, or any other device, monitor, or measurement, device or equipment, and/or any electrical or bio-medical device or equipment, which can measure an individual's physical condition, health condition, health status, healthcare condition, or physiological condition or status, or any other biological or biometric data and/or information. In a preferred embodiment, any of the herein-described pulse rate monitors or measurement devices or equipment, heart rate monitors of measurement devices or equipment, blood sugar monitors or measurement devices or equipment, blood pressure monitors or measurement devices or equipment, blood alcohol monitors or measurement devices or equipment, pacemakers, defibrillators, thermometers, or any other devices, monitors, or measurement devices or equipment, and/or any electrical or bio-medical devices or equipment, can be wirelessly linked with and/or to the CPU 10A and/or to the personal monitoring device 10 and can be wearable, attachable to clothing, or implantable. In a preferred embodiment, the input device(s) 10D can also include a thermometer for measuring the temperature on the exterior of the personal monitoring device 10.

In preferred embodiment, any of the input device(s) described or identified herein can be either connected to, or linked with, or with the CPU 10A directly or indirectly, and/or or can be wirelessly linked to or with the personal monitoring device 10, the CPU 10A, or any other component of the personal monitoring device 10 with or using a Bluetooth device or system and/or any suitable wireless device or wireless linking device or wireless linking system.

The personal monitoring device 10 also includes a display device 10E for displaying data and/or information to a user or operator. In the preferred embodiment, the display device 10E is also connected to, or linked with, the CPU 10A. The personal monitoring device 10 also includes a transmitter(s) 10F, for transmitting signals and/or data and/or information to any one or more of the central processing computer(s) 20, the user communication device(s) 30, the law enforcement communication device(s) 40, the emergency services provider communication device(s) 50, and/or the healthcare records computer(s) 60, and/or any other personal monitoring device(s) 10, which can be utilized in conjunction with the present invention. In the preferred embodiment, the transmitter(s) 10F is/are also connected to, or linked with, the CPU 10A. The personal monitoring device 10 also includes a receiver(s) 10G, for receiving signals and/or data and/or information from any one or more of the central processing computer(s) 20, the user communication device(s) 30, the law enforcement communication device(s) 40, the emergency services provider communication device(s) 50, and/or the healthcare records computer(s) 60, and/or any other personal monitoring device(s) 10, which can be utilized in conjunction with the present invention. In the preferred embodiment, the receiver(s) 10G is/are also connected to, or linked with, the CPU 10A.

The personal monitoring device 10 also includes a database(s) 10H. In the preferred embodiment, the database(s) 10H is/are also connected to, or linked with, the CPU 10A. The database(s) 10H can contain and/or be linked to any of the data and/or information described herein as being stored in the database(s) 20H described herein.

In a preferred embodiment, the database 10H can contain and/or can include any data and/or information, and/or any link or links to any data and/or information, needed or desired for enabling and/or for allowing the personal monitoring device 10 and/or the apparatus 100 and/or any of the computers or communication devices described herein as being utilized in conjunction with the apparatus 100 and method of the present invention to perform any and/or all of the functionality described herein which is capable of being performed by the personal monitoring device 10 and/or the apparatus 100 of the present invention.

In a preferred embodiment, the database 10H can contain and/or can include any software, software programs, algorithms, or software applications ("apps") needed or desired for enabling and/or for allowing the personal monitoring device 10 and/or the apparatus 100 and/or any of the computers or communication devices described herein as being utilized in conjunction with the apparatus 100 and method of the present invention to perform any and/or all of the functionality described herein which is capable of being performed by the personal monitoring device 10 and/or the apparatus 100 of the present invention.

In a preferred embodiment, the database(s) 10H can contain and/or can include any data and/or information regarding the user or the individual, or any users or individuals, who or which utilize the personal monitoring device 10. Any data and/or information regarding the user or individual who is using the personal monitoring device 10 to be monitored, can include, but is not limited to, the user's or the individual's name, address, home telephone number, e-mail address, IP address, test messaging number, text messaging address, cellular telephone number, the telephone number assigned to the personal monitoring device 10, date or birth, gender, height, weight, identification photograph, social security number or any other suitable identification information, and/or any other data and/or information regarding the user of the individual.

The database 10H can also contain and/or can include any data and/or information regarding the user's or the individual's personal monitoring device 10 which can include, but which is not limited to, the type of device, such as for example, a cellular telephone, Smartphone, smartphone, personal digital assistant, or any other device described herein which can be utilized as a personal monitoring device 10, the manufacturing and model number of personal communication device 10, a serial number of the personal monitoring device 10, any other identifying data and/or information assigned to, associated with, or relating to, the personal monitoring device 10, the telephone number associated with, or assigned to, the personal communication device 10, the cellular telephone number associated with, or assigned to, the personal communication device 10, the wireless or mobile telephone number associated with, or assigned to, the personal communication device 10, an IP address associated with, or assigned to, the personal monitoring device 10, an email address associated with, or assigned to the personal monitoring device 10, a text messaging number associated with, or assigned to, the personal monitoring device 10, and/or any other data and/or information associated with the personal monitoring device 10. The database 10H can also contain and/or can include any of the above-described information for any other personal monitoring device 10 or any number of personal monitoring devices 10 which is/are used by the user or individual.

The database 10H can also contain and/or can include any data and/or information regarding a person who is monitoring the user or the individual. In a preferred embodiment, the a person who is monitoring the user or the individual can be, but is not limited to, the user's or individual's parent or parents, spouse, sibling, relative, friend, nanny, au pair, caregiver, teacher, employer, or any other person or entity, who or which is monitoring the user or individual (hereafter also referred to as "monitoring person"). For each monitoring person and, therefore, for each respective parent, spouse, sibling, relative, friend, nanny, au pair, caregiver, teacher, employer, or any other person or entity, who monitors the user of the individual or of or for the user or individual, the database 10H can contain and/or can include any data and/or information regarding the name, address, telephone number, cellular telephone number, user communication device telephone number or cellular telephone number, e-mail address, text messaging number, and/or any other data and/or information, and/or contact information, of, for, or regarding, the monitoring person. The database 10H can also contain and/or can include any other data and/or information, described herein as being stored for or regarding the user or individual, for or regarding the monitoring person.

The database 10H can also contain and/or can include any data and/or information regarding places, locations, or venues, to which the user or individual travels. The database 10H can also contain and/or can include any data and/or information regarding the daily schedule or daily schedules of or for the user or the individual, and/or any data and/or information regarding the daily routine or daily routines of or for the user or individual, any places where the user or individual is or has to be at a given time, and/or any other data and/or information regarding the user's or the individual's daily routines, weekly routines, travel routines, travel routes used, alternate travel routes used, travel times and/or time of travel regarding any travel by the user or individual, and/or any other data and/or information regarding the user's or the individual's routines that can be utilized in performing a personal monitoring service for or regarding the user or the individual.

For example, in the case of a child being monitored, the database 10H can contain and/or can include any data and/or information regarding the daily weekday schedule for the child such as, for example, the child's home address, the time or approximate time when the child leaves home for school, a preferred travel route the child takes to go to school, any alternate travel routes to the school, the time or the approximate time the child arrives at school or the time school starts for the child, the time or the approximate time the child leaves school or the time school ends for the day, a travel route to an after school activity, if applicable, a travel route to the after school activity, an alternate travel route to the after school activity, a time or an approximate time of a travel to an after school activity, a time or an approximate time when the child leaves the venue of the after school activity, a travel route from the venue of the after school activity to the child's home, a travel route to the child's home, an alternate travel route to the child's home, and/or a time or an approximate time when the child is expected to arrive at home.

As and for another example, in the case of an adult of any age being monitored, the database 10H can contain and/or can include any data and/or information regarding the daily weekday schedule for the adult such as, for example, the adult's home address, the time or approximate time when the adult leaves home for work or some other activity or venue, a preferred travel route the adult takes to go to work or some other activity or venue, any alternate travel routes to the work, activity, or venue, the time or the approximate time the adult arrives at work, the activity, or the venue, the time or the approximate time the adult leaves work, the activity, or the venue, a travel route to another activity or venue, if applicable, a travel route to the other activity or venue, an alternate travel route to the other or venue, a time or an approximate time of a travel to the other activity or venue, a time or an approximate time when the adult leaves the other activity or venue, a travel route from the other activity or venue back to the adult's home, a travel route to the adult's home, an alternate travel route to the adult's home, and/or a time or an approximate time when the adult is expected to arrive at home.

The database 10H can also contain and/or can include any data and/or information regarding any school(s), workplace(s), club(s), activity venue(s), recreational venue(s), entertainment venue(s), or any other place(s), location(s), and/or other venue(s), of the user or individual and/or to which the user or individual travels and/or at which the user or individual is known to spend time. The database 10H can also contain and/or can include any data and/or information regarding the location(s) of any school(s), workplace(s), club(s), activity venue(s), recreational venue(s), entertainment venue(s), or any other place(s), location(s), and/or other venue(s), of the user or individual, which data and/or information can include the name, the address, the telephone number, the website address, the IP address, a description of same, schedule information of or for same, and/or any other information regarding same.

The database 10H can also contain and/or can include any data and/or information regarding any weekday or weekend day schedules or itineraries of the user or individual. The database 10H can also contain and/or can include any data and/or information regarding emergency contacts for the user or the individual, including, for each emergency contact individual, his or her name, telephone number, cellular telephone number, text messaging number, e-mail address, or IP address, or any other information.

The database 10H can also contain and/or can include any data and/or information regarding any personal monitoring accounts the user or individual has or is associated with. The database 10H can also contain and/or can include any data and/or information regarding any persons responsible for monitoring the user or the individual including for each person, his or her name, telephone number, cellular telephone number, text messaging number, e-mail address, or IP address, or any other information. The database 10H can also contain and/or can include any data and/or information regarding any and/or all personal monitoring devices 10 assigned to or associated with the user or individual and/or can contain and/or can include data and/or information regarding with any the user's or individual's personal monitoring accounts.

The database 10H can also contains and/or can include any data and/or information regarding any of the central processing computer(s) 20, any pertinent user communication device(s) 30, any law enforcement communication device(s) 40, any emergency services provider communication device(s) 50, and/or the healthcare records computer(s) 60, described herein, and/or can contain and/or can include any link(s) or hyperlink(s) to same.

The database 10H can also contain and/or can include an electronic healthcare record of the user or the individual and/or any data and/or information regarding same or contained in same, any data and/or information which may be contained in the electronic healthcare record of the user or the individual, any personal healthcare record of the user or individual, any data and/or information which may be contained in the personal healthcare record of the user or the individual, any healthcare information regarding the user or the individual, any information regarding any healthcare condition or special needs of the user or the individual, any information regarding any medicines, prescribed medications, drugs, or prescribed drugs, which are needed by the user or the individual, any information regarding any allergies of the user or the individual, or any other information regarding any healthcare conditions, needs, or treatments, of, for, or regarding, the user or the individual. The database 10H can also contain and/or can include a link or hyperlink to the healthcare records computer 60 and/or to the user's or the individual's electronic healthcare record stored therein.

The database 10H can also contain and/or can include any data and/or information regarding the daily schedule for each weekday or each weekend day for the user or the individual, travel routes travelled for each day and trip, and/or time(s) associated with each trip or travel segment of each trip.

The database 10H can also contain and/or can include any data and/or information regarding the name, address, telephone number(s), cellular telephone number(s), mobile or wireless telephone number(s), e-mail address(es), text messaging address(es), IP address(es), or any other contact information for or regarding any herein-described monitoring person of or for the user or the individual or for each or any parent, sibling, family member, relative, caregiver, nanny. au pair, healthcare provider(s), healthcare insurer(s) or healthcare payer(s), or any other person or entity of or for the user or the individual.

It is important to note, as used throughout the application, the term or phrase "text messaging number" includes any and all kinds of messaging numbers, including, but not limited to, a text messaging number, an SMS messaging number, and MMS messaging number, or any other number, address, or identifier, used or needed in order to send a text message or any other message to any user, individual, person, or entity who or which uses the apparatus 100 of the present invention.

The database 10H can also contain and/or include any software, software program(s), algorithm(s), or software applications ("apps"), such as those known by those skilled in the art at the time of the filing of this application, which can allow the personal monitoring device 10 to ascertain, determine, locate, and/or display, a location or position of any user communication device 30 associated with any user or individual, including, but not limited to, any user or individual who is to be monitoring the user or individual who is using or who is associated with the personal monitoring device 10, or any other authorized or designated user or individual who might be able to provide assistance to the user or individual who is using or who is associated with the personal monitoring device 10.

The database 10H can also contain and/or can include navigation software for allowing the personal monitoring device 10 to calculate travel routes from one place or point to another, to detect departures from a travel route and to re-calculate another travel route, and/or for allowing the personal monitoring device 10 to calculate and/or to store travel routes and/or any data and/or information regarding same which are used by the user or individual as well as alternate travel routes for same. The database 10H can also contain and/or can include any data and/or information regarding any allowed travel routes for the user or individual as well as disallowed travel routes for the user of individual. The database 10H can also contain and/or include map data and/or map information including, but not limited to, digitized map data and/or information and/or data and/or information for updating any map data and/or information.

The database 10H can also contain and/or include data and/or information regarding travel records for the user or individual which can contain and/or include data and/or information regarding a date and time of travel and/or travel routes taken or travelled by, and/or any other data and/or information regarding, the user or individual for or during any period of time or during and/or for or relating to any schedule or routine.

The database 10H can also contain and/or include a pre-recorded audio message(s) and/or a pre-recorded audio and video message(s), which can be recorded by any person authorized to monitor the user or individual and which can provided via the personal monitoring device 10 at any time and/or for any reason. For example, an audio and/or an audio and video recording can be played via the personal monitoring device 10 in order to assist, calm, or comfort, a lost child, to help re-orient a child, to give or provide the child or any one with whom the child comes into contact with, instructions, contact information, emergency contact information, directions, or any other information, and/or can be played to clam, comfort, or assist, a lost, disoriented, or ill, adult or child of any age, or to give or provide the child or any one with whom the child comes into contact with, instructions, contact information, emergency contact information, directions, or any other information.

The database 10H can also contain and/or can include any data, information, software, software programs, algorithms, and/or software applications (or "apps") which are needed or desired for allowing the personal monitoring device 10 to perform any and/or all of the functions and/or functionality described herein as being capable of being performed by same and/or by the apparatus 100 and method of the present invention.

The database 10H can also contain and/or can include any of the data and/or information described herein as being stored in any of other databases 20H, 30H, 40H, 50H, and/or 60H, described herein.

The personal monitoring device 10 also includes an output device(s) 10I for outputting any of the data, information, and/or reports, described herein as being generated by or via the personal monitoring device 10. In the preferred embodiment, the output device(s) 10I can be a display screen, a speaker, a printer, a display of any type or kind, an indicator light, a transmitter, a modem, and/or any other device which can be used to output data or information of any kind or type. In the preferred embodiment, the output device(s) 10I can also include a beacon or a homing beacon which can transmit or provide a signal, a distress signal, or any other indication, from the personal monitoring device 10 which can be utilized determine the position, location, and/or movement, of the personal monitoring device 10. In the preferred embodiment, the output device(s) 10I is/are also connected to, or linked with, the CPU 10A.

The personal monitoring device 10 also includes a video and/or audio recording device(s) 10J which can include a camera and/or a video recording device for recording pictures or video and/or video clips and/or a microphone or an audio recording device for recording audio or audio clips which can be recorded by, and/or transmitted live, by or from the personal monitoring device 10, or which can be recorded by, and stored at or in, the personal monitoring device 10 for transmission by or from the personal monitoring device 10 at a later time. The video and/or audio recording device(s) 10J can be utilized to facilitate video conferencing, video chatting, and/or audio conferencing, and/or video and audio conferencing, between users of the personal monitoring device 10 and any user of any other computer or communication device 10, 20, 30, 40, 50, or 60, described herein. In the preferred embodiment, the video and/or audio recording device(s) 10J is/are also connected to, or linked with, the CPU 10A.

With reference to FIG. 2, the personal monitoring device 10 can also include a global positioning system (GPS) device 10K which can be utilized to determine or ascertain the location or position of the personal monitoring device 10 at any time and/or to track movement of the personal monitoring device 10. In a preferred embodiment, the global positioning system (GPS) device 10K can be connected to, or linked with, the CPU 10A.

The personal monitoring device 10 also includes device functional equipment systems or devices 10L, which can include any the necessary communications systems or devices which are typically found in cellular telephones or wireless telephones and/or which can allow the personal monitoring device 10 to function as a cellular telephone or a wireless telephone. In a preferred embodiment, the functional equipment systems or devices 10L can also include a global positioning system (GPS) device which can be utilized to determine or ascertain the location or position of the personal monitoring device 10 at any time and which can be also be used to track movement of the personal monitoring device 10.

In a preferred embodiment, the functional equipment systems or devices 10L can also include navigation equipment or devices which are typically found in navigation devices or equipment and which an be utilized to allow the personal monitoring device 10 to function and/or to operate as a GPS equipped navigation device. In a preferred embodiment, the personal monitoring device 10 can function as a stand alone navigation device, meaning that it can perform any and/or all needed and desired navigation tasks and functions without any interaction with an external computer or device, and/or without having to access a computer over any communication network in order to obtain navigation data, information, and/or instructions, for providing navigation data, information, and/or instructions, to a user of the personal monitoring device 10.

In another preferred embodiment, the functional equipment systems or devices 10L can also include a "kill" switch or associated hardware and/or software for disabling and/or deactivating the personal monitoring device 10 in instances when same might be lost or stolen, so as to prevent its use by another person and/or to prevent any access to any data and/or information stored therein, thereby rendering the personal monitoring device 10 useless to another person after being reported, or discovered as being, lost or stolen.

In another preferred embodiment, the personal monitoring device 10 can also operate in conjunction with an external computer or device in order to obtain navigation data, information, and/or instructions, so as to provide same to a user of the personal monitoring device 10. In another preferred embodiment, the personal monitoring device 10 can process navigation data, information, and/or instructions, on its own as well as receive at least some navigation data, information, and/or instructions, from an external computer or device, in order to provide navigation data, information, and/or instructions, to a user of the personal monitoring device 10. In a preferred embodiment, the functional equipment systems or devices 10L are also connected to, or linked with, the CPU 10A.

In a preferred embodiment, the functional equipment systems or devices 10L can also include any combination of hardware and/or software for disabling the on/off switch of the personal monitoring device 10, so that the personal monitoring device 10 cannot be shut-off, or so that no operation or function of the personal monitoring device 10 can be terminated, and/or so that a telephone call, a telephone communication link, or a communication line or link, cannot be turned off or terminated, by or at the personal communication device 10. In this regard, in the case of an emergency, no telephone call and/or communication line or link between the personal monitoring device 10 and any user communication device(s) 30, the or any central processing computer(s) 20, the or any law enforcement communication device(s) 40, the or any emergency services provider communication device(s) 50, and/or the or any healthcare records computer(s) 60, can be terminated at or by the personal monitoring device 10, so that a communication line, link, or channel can always be maintained with the personal monitoring device 10.

In this regard, for example, if a child is lost, a telephone call and/or communication line, link, or channel, with and between the child and his or her parent can be maintained without the risk of the call being terminated at or by the personal monitoring device 10. In this regard, the parent can continue to speak with and communication with the child, can obtain position or location information from or via the personal monitoring device 10, can track the personal monitoring device 10, and/or can obtain any other information from and/or via the personal monitoring device 10, without losing contact with the child and/or his or her personal monitoring device 10.

In a preferred embodiment, the functional equipment systems or devices 10L can also include any combination of hardware and/or software for allowing the personal monitoring device 10 and any components or devices therein or associated therewith to be remotely accessed, controlled, and/or monitored, by or using any authorized user communication device 30 used by an authorized user or individual, the or any central processing computer(s) 20, the or any law enforcement communication device(s) 40, the or any emergency services provider communication device(s) 50, and/or the or any healthcare records computer(s) 60.

Figure 3:
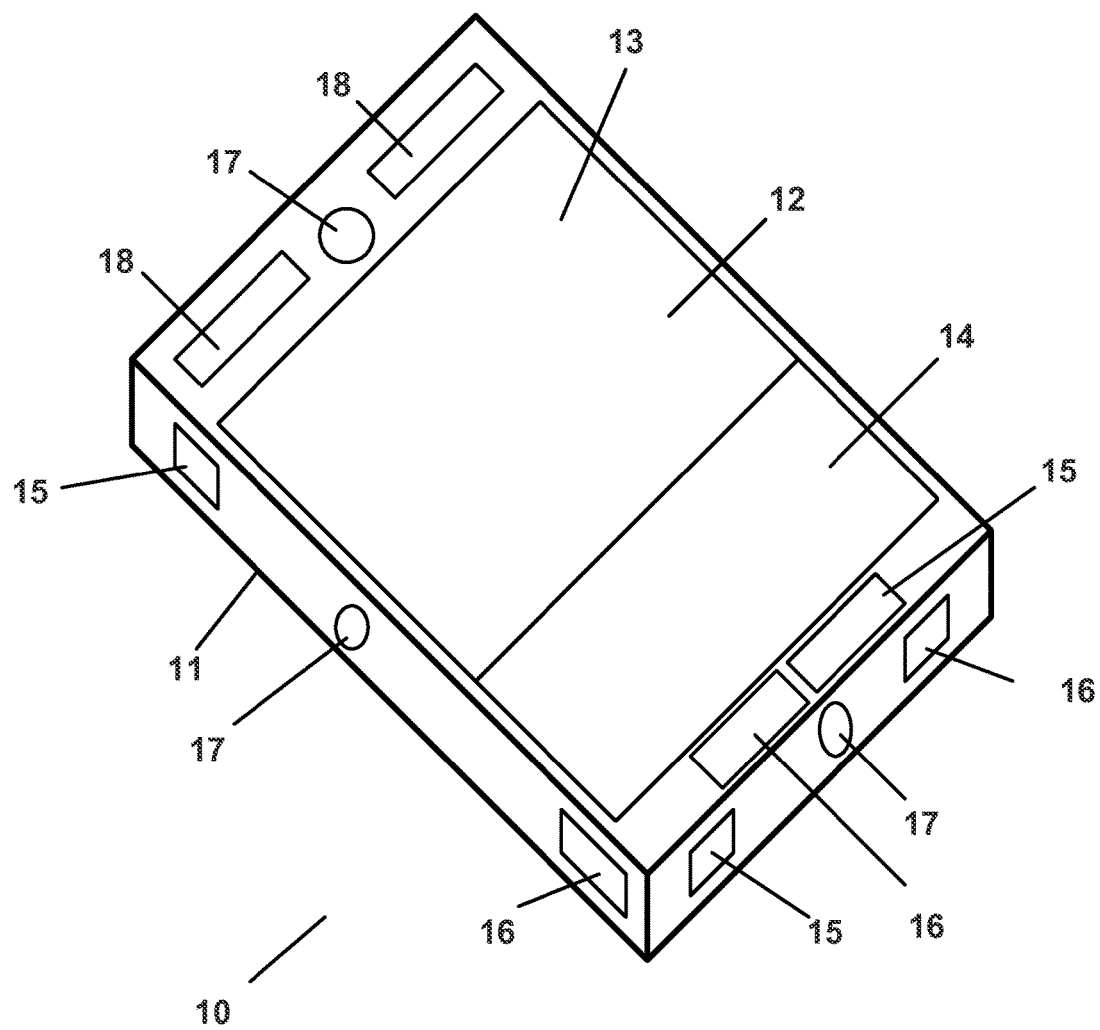
FIG. 3 illustrates the personal monitoring device of FIG. 1 in a three-dimensional perspective view.

FIG. 3 illustrates the personal monitoring device 10 of FIG. 1 in a three-dimensional perspective view. In a preferred embodiment, the personal monitoring device 10 can be, or can be implemented in or with, a cellular telephone, a Smartphone, a smartphone, or a personal digital assistant, which can be equipped with all of the necessary hardware and software needed to perform all of the functions and functionality described herein as being performed by the personal monitoring device 10 of the present invention. In another preferred embodiment, the personal monitoring device 10 can be designed to be of any size or shape, and/or the personal monitoring device 10 can be implemented using a watch, a wristwatch, an necklace, a bracelet, a ring, or any other article of jewelry, of the personal monitoring device 10 can be secured to a belt, a necklace, a bracelet, eyeglasses, a watch, a wristwatch, and/or can be attached to, secured to, or placed inside or within, any article of clothing, a jacket, a coat, a shirt, a blouse, a dress, a skirt, a pair of pants, shoes, sneakers, boots, a hat, gloves, socks, stockings, a tie, a scarf, or any other wearable item or accessory. In this regard, and depending of the use, application, or deployment, of the personal monitoring device 10 in any given setting or situation, the personal monitoring device 10 can be designed and/or configures to be of any size, shape, type, or kind, of device.

With reference to FIG. 3, in a preferred embodiment, the personal monitoring device 10 can include a housing 11, a display screen 12 which can be a component of the display device 10E. In the preferred embodiment, the display screen 12 can of the touch screen type or kind and can be utilized to view and to input data, information, messages, or instructions. In a preferred embodiment, the display screen 12 can include a display section 13 and a keyboard section 14. In a preferred embodiment, the keyboard section 14 can be called upon when needed and can also be dispensed with when not being used so as to facilitate the use of the entirety of the display screen 12 when desired.

In a preferred embodiment, the personal monitoring device 10 can also be equipped with a flashlight, a flashlight bulb, or with any suitable software application which can turn the display screen 12, or any portion of the display screen 12, into a flashlight. In this regard, the personal monitoring device 10 can be equipped with a flashlight or a flashlight functionality.

With reference once again to FIG. 3, the personal monitoring device 10 can also include one or more microphones 15, which can be a component of the video and/or audio recording device(s) 10J and/or the input device 10D and, which can be located on one or more, or on any or all surfaces of the personal monitoring device 10 in order to allow for any user or other individual to utilize the personal monitoring device 10 to communicate with others, to allow others to monitor audio and/or sounds at or in the vicinity of the personal monitoring device 10, and/or to allow one to use, control an operation of, to enter voice commands into, and/or to record audio information or an audio clip with and/or using, the personal monitoring device 10, and/or to allow one to simply utilize the personal monitoring device 10 to communicate with another individual or entity in a hand-free mode of operation. Any number of microphones 15 can be utilized in connection with the personal monitoring device 10.

With reference once again to FIG. 3, the personal monitoring device 10 can also include one or more speakers 16, which can be a component of the output device 10I and, which can be located on one or more, or on any or all, surfaces of the personal monitoring device 10 in order to provide audible data, information, instructions, or communications, to any user, or individual who may be using, or who may be in the vicinity of, the personal monitoring device 10.

With reference once again to FIG. 3, the personal monitoring device 10 can also include one or more cameras 17, which can be a component of the video and/or audio recording device(s) 10J and/or the input device 10I and, which can be located on one or more, or on any or all, surfaces of the personal monitoring device 10 in order to take or record a picture, a photograph, or an image, and/or to record video information or a video clip, with the personal monitoring device 10, to record a picture, a photograph, or an image, and/or to record video information or a video clip, of a user of the personal monitoring device 10 or any individual using the personal monitoring device 10 or in the vicinity of the personal monitoring device 10, to record a picture, a photograph, or an image, and/or to record video information or a video clip, of a vicinity in which the personal monitoring device 10 is located or of a surrounding of same, and/or to allow a user or any individual to engage in a video conference or video chat with another individual or other individuals using the personal monitoring device 10.

In a preferred embodiment, any one or more cameras 17 can be a wide angle lens camera or a camera having a wide angle lens for obtaining maximum viewing area. In a preferred embodiment, any one or more cameras 17 can also be a night vision camera, an infrared camera, or a camera equipped with, or utilized in connection with, night vision capability.

With reference once again to FIG. 3, the personal monitoring device 10 can include a plurality of indicator lights 18, one of which can be used to provide an indication that the user of the personal monitoring device 10 is located with a "safe" zone of travel and the other which can be used to provide an indication that the user of the personal monitoring device 10 is located outside of a "safe" zone of travel, is lost, is ill, is possibly the victim of foul play, or is otherwise in need of help or assistance. In a preferred embodiment, the indicator light which is used to indicate the that user in within his or her "safe" zone can be an green light when illuminated, and the indicator light which is used to indicate the that the user outside his or her "safe" zone of travel, is lost, is ill, is possibly the victim of foul play, or is otherwise in need of help or assistance, can be a red light when illuminated. In another preferred embodiment, the indicator lights 19 can be provided via the display screen or in or via a portion or section of the display screen 12.

In another preferred embodiment, the personal monitoring device 10 can include any suitable attachment device or element (not shown) which is attached or connected to, or linked with, the housing 11 and/or the personal monitoring device 10 and which can be used to secure, to mount, or to otherwise attach, the personal monitoring device 10 to, on, or in, a belt, an article of clothing, a watch, a wristwatch, a necklace, a bracelet, eyeglasses, an accessory of any type or kind, a jacket, a coat, a shirt, a blouse, a dress, a skirt, a pair of pants, shoes, sneakers, boots, a hat, gloves, socks, stockings, a tie, a scarf, or any other wearable item or accessory.

In a preferred embodiment, the personal monitoring device 10, its housing 11, and its various component parts described herein, can be constructed or rugged materials in order to protect the personal monitoring device 10 against impacts. In a preferred embodiment, the personal monitoring device 10, its housing 11, and its various component parts described herein, can also be sealed, in any appropriate manner, so as to provide for a personal monitoring device 10 which can be waterproof. In a preferred embodiment, the personal monitoring device 10 can also be designed and manufactured to as to include any suitable or buoyant material(s) which can allow the personal monitoring device 10 to float on water. In a preferred embodiment, the housing 11, or any portion or component of same, can also include made with or from, or can contain a phosphorescent material so that the housing 11, or any portion of the housing 11, of the personal monitoring device 10 can glow-in-the dark or otherwise exhibit glow-in-the-dark or luminescent properties.

Figure 4:
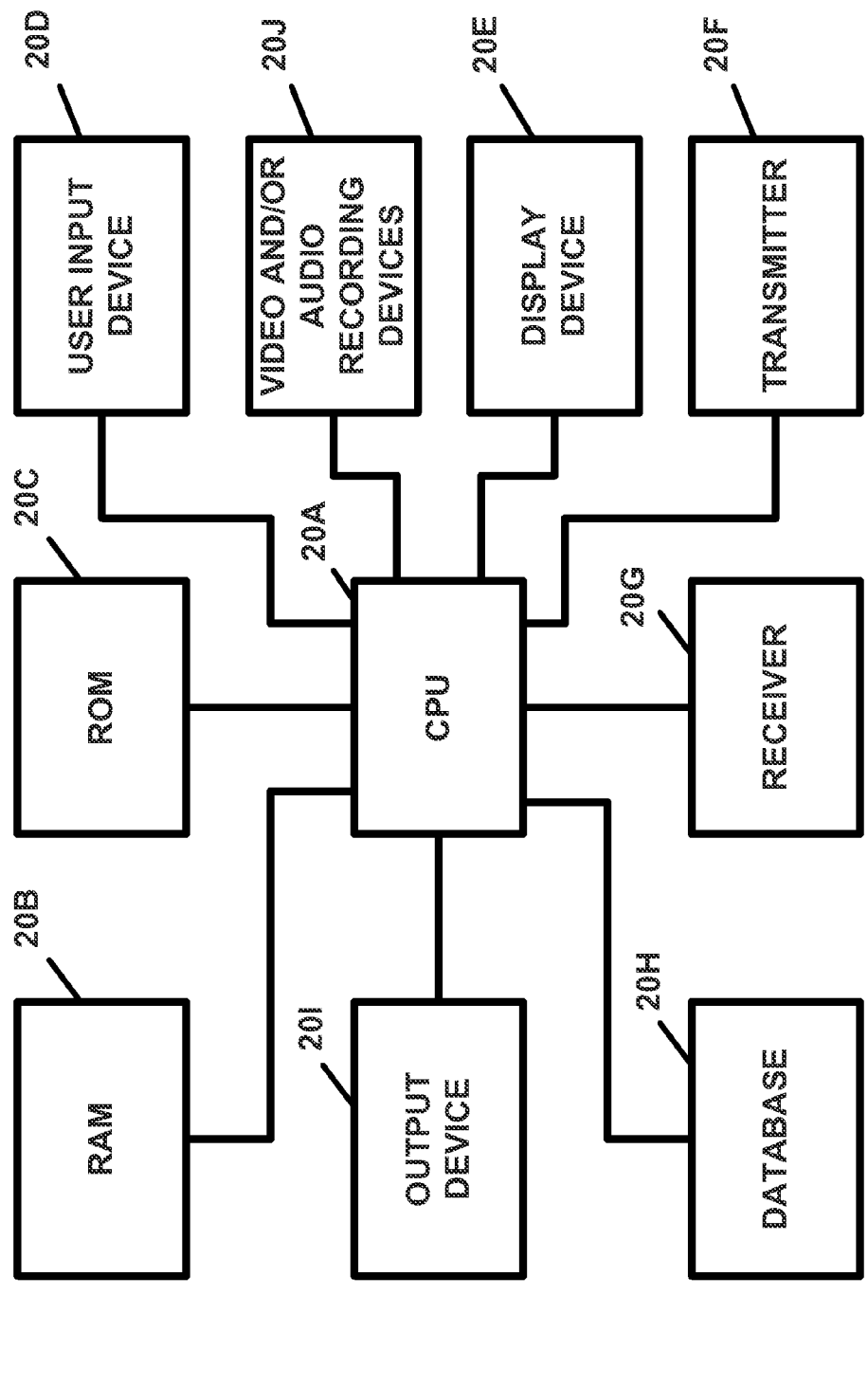
FIG. 4 illustrates the central processing computer of FIG. 1, in block diagram form.

FIG. 4 illustrates the central processing computer 20 of FIG. 1, in block diagram form. In the preferred embodiment, the central processing computer 20 can be any computer capable of performing the functionality of the central processing computer 20 as described herein, a server computer, a computer system, a group of computers, or any computer capable of being utilized in a network or capable of being utilized with other computers in a network, which can provide the functionality of, and which can be utilized as, a central processing computer 20. The central processing computer 20 can also be any suitable server computer or server computer system, a cloud computer or cloud computer system, or any computer or computer system capable of being utilized in a network or capable of being utilized with other computers or computer systems in a network. The central processing computer 20 can also be an Internet server computer and/or a web site server computer. In the preferred embodiment, the central processing computer 20 includes a central processing unit or CPU 20A, which in the preferred embodiment, is a microprocessor. The CPU 20A can also be a microcomputer, a minicomputer, a macro-computer, and/or a mainframe computer, depending upon the application.

The central processing computer 20 also includes a random access memory device(s) 20B (RAM), a read only memory device(s) 20C (ROM), each of which is connected to, or linked with, the CPU 20A, and a user input device 20D, for inputting and/or entering data and/or information and/or instructions and/or commands into the central processing computer 20, which can include any one or more of a keyboard, a scanner, a user pointing device, such as, for example, a mouse, a touch pad, and/or an audio input device and/or a video input device, a microphone or audio recording device, a camera or a video recording device, and/or any device, electronic and/or otherwise which can be utilized for inputting and/or entering data and/or information, as well as instructions and/or commands, into the central processing computer 20. The central processing computer 20 also includes a display device 20E for displaying data and/or information to a user or operator. In the preferred embodiment, the display device 20E is also connected to, or linked with, the CPU 20A.

The central processing computer 20 also includes a transmitter(s) 20F, for transmitting signals and/or data and/or information to any one or more of the personal monitoring device(s) 10, the user communication device(s) 30, the law enforcement communication device(s) 40, the emergency services provider communication device(s) 50, and/or the healthcare records computer(s) 60, and/or any other central processing computer(s) 20, which can be utilized in conjunction with the present invention. In the preferred embodiment, the transmitter(s) 20F is/are also connected to, or linked with, the CPU 20A. The central processing computer 20 also includes a receiver(s) 20G, for receiving signals and/or data and/or information from any one or more of the personal monitoring device(s) 10, the user communication device(s) 30, the law enforcement communication device(s) 40, the emergency services provider communication device(s) 50, and/or the healthcare records computer(s) 60, and/or any other central processing computer(s) 20, which may be utilized in conjunction with the present invention. In the preferred embodiment, the receiver(s) 20G is/are also connected to, or linked with, the CPU 20A.

The central processing computer 20 also includes a database(s) 20H which, in the preferred embodiment, contains and/or includes any and/or all of the data and/or information needed or desired for or by the central processing computer 20 to perform all of the operations, actions, functions, and/or functionality, described herein as being provided by, and/or as being performed by, the central processing computer 20 and/or the apparatus 100 of the present invention. In the preferred embodiment, the database(s) 20H is/are also connected to, or linked with, the CPU 20A.

In a preferred embodiment, the database(s) 20H can contain and/or include any and/or all of any needed or desired data and information regarding each of the users or individuals being monitored, or are to be monitored, by, with, or using, the apparatus 100, including, but not limited to, any of the data and/or information described herein as being stored in the database 10H of any personal monitoring device 10 associated with or used by the respective user or individual.

In a preferred embodiment, the database(s) 20H can also contain and/or include any and/or all of any needed or desired data and information regarding each of the users or individuals who utilize the apparatus 100 of the present invention to monitor any other user or individual, including, but not limited to, any of the data and/or information described herein as being stored in the database 30H of any user communication device 30 associated with or used by the respective user or individual desiring to monitor any other user or individual.

In a preferred embodiment, for each user or individual who or which uses the apparatus 100 and method of the present invention to monitor another user or individual, the database 20H can contain and/or include, but not limited to, any data and/or information regarding the user's or the individual's name, address, telephone number(s), cellular telephone number(s), mobile or wireless telephone number(s), e-mail address or e-mail addresses, and/or text message, instant message, SMS message, or MMS message, IP address(es), or any other messaging, telephone number, or other, address or identifier, as well as any data and/or information regarding the user's or the individual's user communication device 30, including, but not limited to, the manufacturer, model number, and/or serial number of same, as well as any telephone number, e-mail address, instant message number or address, SMS message number or address, MMS message number or address, IP address, or any other contact information of, for, or associated with the user communication device 30, for each user communication device 30 used by or associated with the user or individual. The database 20H can also contain and/or include any data and/or information regarding any other user(s) or individual(s) being monitored, or to be monitored, by the user or individual.

In a preferred embodiment, for each user or individual who or which is being monitored, or is to be monitored, by, with, or using, the apparatus 100 and method of the present invention, the database 20H can contain and/or include, but not limited to, any data and/or information regarding the user's or the individual's name, address, telephone number(s), cellular telephone number(s), mobile or wireless telephone number(s), e-mail address or e-mail addresses, and/or text message, instant message, SMS message, or MMS message, IP address(es), or any other messaging, telephone number, or other, address or identifier, as well as any data and/or information regarding the user's or the individual's personal monitoring device 10, including, but not limited to, the manufacturer, model number, and/or serial number of same, as well as any telephone number, e-mail address, instant message number or address, SMS message number or address, MMS message number or address, IP address, or any other contact information of, for, or associated with the personal monitoring device 10, for each personal monitoring device 10 used by or associated with the user or individual.

For each user or individual who or which utilizes the apparatus 100 and method of the present invention to monitor another user or individual, the database 20H, in a preferred embodiment, can contain and/or include any data and/or information regarding the user(s) or individual(s) being monitored or to be monitored.

For each user or individual being monitored by, or to be monitored by, another user or individual, the database 20H, in a preferred embodiment, can contain and/or include any data and/or information regarding the user(s) or individual(s) who is to monitor that user or individual.

In a preferred embodiment, the database 20H can contain and/or include any data and/or information regarding any personal monitoring account(s) associated with any user(s) or individual(s) who are being monitored, or to be monitored, by, with, or using, the apparatus 100 of the present invention including, but not limited to any number or identifier for the respective personal monitoring account, account number, any user(s) or individual(s) being monitored, or to be monitored, under the personal monitoring account, and/or any user(s) or individual(s) authorized to use the personal monitoring account to monitor another user(s) or individual.

In a preferred embodiment, the database 20H can contain and/or include, for each user or individual being monitored, or to be monitored, by, with, or using, the apparatus 100 and method of the present invention, data and/or information regarding places, locations, or venues, to which the user or individual travels, along with any data and/or information regarding the daily schedule or daily schedules of or for the user or the individual, and/or any data and/or information regarding the daily routine or daily routines of or for the user or individual, any places where the user or individual is or has to be at a given time, and/or any other data and/or information regarding the user's or the individual's daily routines, weekly routines, travel routines, travel routes used, alternate travel routes used, travel times and/or time of travel regarding any travel by the user or individual, and/or any other data and/or information regarding the user's or the individual's routines that can be utilized in performing a personal monitoring service for or regarding the user or the individual.

For example, in the case of a child being monitored, the database 20H can contain and/or can include any data and/or information regarding the daily weekday schedule for the child such as, for example, the child's home address, the time or approximate time when the child leaves home for school, a preferred travel route the child takes to go to school, any alternate travel routes to the school, the time or the approximate time the child arrives at school or the time school starts for the child, the time or the approximate time the child leaves school or the time school ends for the day, a travel route to an after school activity, if applicable, a travel route to the after school activity, an alternate travel route to the after school activity, a time or an approximate time of a travel to an after school activity, a time or an approximate time when the child leaves the venue of the after school activity, a travel route from the venue of the after school activity to the child's home, a travel route to the child's home, an alternate travel route to the child's home, and/or a time or an approximate time when the child is expected to arrive at home.

As and for another example, in the case of an adult of any age being monitored, the database 20H can contain and/or can include any data and/or information regarding the daily weekday schedule for the adult such as, for example, the adult's home address, the time or approximate time when the adult leaves home for work or some other activity or venue, a preferred travel route the adult takes to go to work or some other activity or venue, any alternate travel routes to the work, activity, or venue, the time or the approximate time the adult arrives at work, the activity, or the venue, the time or the approximate time the adult leaves work, the activity, or the venue, a travel route to another activity or venue, if applicable, a travel route to the other activity or venue, an alternate travel route to the other or venue, a time or an approximate time of a travel to the other activity or venue, a time or an approximate time when the adult leaves the other activity or venue, a travel route from the other activity or venue back to the adult's home, a travel route to the adult's home, an alternate travel route to the adult's home, and/or a time or an approximate time when the adult is expected to arrive at home.

For each user or individual being monitored, or to be monitored, by, with, or using, the apparatus 100 of the present invention, the database 20H can also contain and/or can include any data and/or information regarding any school(s), workplace(s), club(s), activity venue(s), recreational venue(s), entertainment venue(s), or any other place(s), location(s), and/or other venue(s), of the user or individual and/or to which the user or individual travels and/or at which the user or individual is known to spend time. The database 20H can also contain and/or can include any data and/or information regarding the location(s) of any school(s), workplace(s), club(s), activity venue(s), recreational venue(s), entertainment venue(s), or any other place(s), location(s), and/or other venue(s), of the user or individual, which data and/or information can include the name, the address, the telephone number, the website address, the IP address, a description of same, schedule information of or for same, and/or any other information regarding same.

The database 20H can also contain and/or can include, for each user or individual monitored, or to be monitored, by, with, or using, the apparatus 100 of the present invention, any data and/or information regarding any weekday or weekend day schedules or itineraries of the user or individual. The database 20H can also contain and/or can include any data and/or information regarding emergency contacts for the user or the individual, including, for each emergency contact individual, his or her name, telephone number, cellular telephone number, text messaging number, e-mail address, or IP address, or any other information.

The database 20H can also contain and/or include any data and/or information regarding schedules, travel schedules, allowed travel routes, disallowed travel route, allowed places, locations, or venues, disallowed places, locations, or venues, and/or limitations or restrictions regarding any of same, for each user or individual monitored, or to be monitored, by, with, or using, the apparatus 100 of the present invention.

The database 20H can also contain and/or include, for each user or individual monitored, or to be monitored, by, with, or using, the apparatus 100 of the present invention, data and/or information regarding past travels, movements, or activities, including, but not limited to, travel routes and dates and/or times of same, as well as future travel plans, movements, or activities, for each such user or individual.

The database 20H can also contain and/or include, for each user or individual who is being monitored, or who is to b monitored by, with, or using, the apparatus 100 of the present invention, a pre-recorded a audio message(s) and/or a pre-recorded audio and video message(s), which can be recorded by any person authorized to monitor the user or individual and which can downloaded to the personal monitoring device 10 at any time and/or for any reason. For example, an audio and/or an audio and video recording can be played at the personal monitoring device 10 in order to assist, calm, or comfort, a lost child, to help re-orient a child, to give or provide the child or any one with whom the child comes into contact with, instructions, contact information, emergency contact information, directions, or any other information, and/or can be played at or via the personal monitoring device 10 in order to clam, comfort, or assist, a lost, disoriented, or ill, adult or child of any age, or to give or provide the child or any one with whom the child comes into contact with, instructions, contact information, emergency contact information, directions, or any other information.

The database 20H can also contain and/or include any data and/or information for calculating, tracking, and/or monitoring, travel routes and travel activities for monitored, or to be monitored, by, with, or using, the apparatus 100 of the present invention. The database 20H can also contain and/or include any stored video and/or audio which is recorded by any personal monitoring device 10, as well as any tracking information regarding the personal monitoring device 10 for any personal monitoring device 10 utilized in connection with the apparatus 100 and method of the present invention.

The database 20H can also contain and/or include any data and/or information, as well as any software, software programs, algorithms, and/or software application, for enabling the central processing computer 20, any user communication device 30 associated with an authorized user or individual, any authorized law enforcement personnel, or any authorized emergency services personnel, to access, to monitor or to monitor an operation of, or to control or to control an operation of, a personal monitoring device 10 user by or associated with a user or individual monitored, or to be monitored, by, with, or using, the apparatus 100 of the present invention. In this regard, an authorized user, individual, or personnel can access, monitor, or control, a respective personal monitoring device 10 via the central processing computer 20.

The database 20H can also contain and/or include, for each user or individual monitored, or to be monitored, by, with, or using, the apparatus 100 of the present invention, and for each user or individual who is monitoring, or who is to be monitoring, any other user or individual, an electronic healthcare record, an electronic medical record, an electronic dental record, a healthcare record, and/or a personal healthcare record, for the respective user or individual, which can include any data and/or information typically found in any electronic healthcare records, electronic medical records, electronic dental records, healthcare records, and/or personal healthcare records. The database 20H can also include for each user or individual, information regarding any healthcare conditions of the user or individual, any medicines, medications, or drugs, the user or individual is taking or required to take, any allergies the user or individual may have, and/or any other information which may be needed or useful for the user's or the individual's well being.

The database 20H can also contain and/or include any and/or all data and/or information regarding any and/or all personal monitoring devices 10, any other central processing computer(s) 20, any and/or all user communication devices 30, any and/or all law enforcement communication device(s) 40, any and/or emergency services provider communication device(s) 50, and/or any and/or all healthcare records computer(s) 60, utilized in connection with the apparatus 100 of the present invention, as well any data and/or information stored therein, and/or any link(s) or hyperlink(s) to same or to any data and/or information stored in same.

The database 20H can also contain and/or include any and/or data and/or information described herein as being stored in any of the herein-described databases 10H, 30H, 40H, 50H, and/or 60H.

It is to also be understood that the database 20H, in a preferred embodiment, can also contain and/or include any data and/or information, and/or any software, software programs, algorithms, and/or soft applications, needed or desired, whether described herein or not, for allowing the central processing computer 10, the apparatus 100, and/or any of the herein-described personal monitoring devices 10, user communication devices 30, law enforcement communication device(s) 40, emergency services provider communication device(s) 50, and/or any and/or all healthcare records computer(s) 60, to perform the functions described herein as being performed and/or provided by the apparatus 100 and method of the present invention and/or by the central processing computer 20, any personal monitoring device 10, any user communication device 30, any law enforcement communication device 40, any emergency services provider communication device 50, and/or any healthcare records computer 60.

The database 20H can also contain and/or include any software, software program(s), algorithm(s), or software applications ("apps"), such as those known by those skilled in the art at the time of the filing of this application, which can be downloaded at any time to any personal monitoring device 10, and which can allow the personal monitoring device 10 to ascertain, determine, locate, and/or display, a location or position of any user communication device 30 associated with any user or individual, including, but not limited to, any user or individual who is to be monitoring the user or individual who is using or who is associated with the personal monitoring device 10, or any other authorized or designated user or individual who might be able to provide assistance to the user or individual who is using or who is associated with the personal monitoring device 10.

The database 20H can also contain and/or include any software, software program(s), algorithm(s), or software applications ("apps"), such as those known by those skilled in the art at the time of the filing of this application, which can be downloaded at any time to any user communication device 30, and which can allow the user communication device 30 to ascertain, determine, locate, and/or display, a location or position of any personal monitoring device 10 used by or associated with any user or individual who is being monitoring by the user or individual who is using or who is associated with the user communication device 30.

In a preferred embodiment, the database(s) 20H can also contain and/or include any software programs, software algorithms, and/or software applications ("apps") deemed to be necessary, desirable, and/or useful, in utilizing the apparatus 100 and method of the present invention in the various embodiments described herein. In a preferred embodiment, the database(s) 20H can also contain and/or include any other data and/or information deemed to be necessary, desirable, and/or useful, in utilizing the apparatus 100 and method of the present invention in the various embodiments described herein. The database(s) 20H can also contain and/or include any other data and/or information which is or may be needed and/or desired in performing any and/or all of the features and/or functionality described herein as being provided by the apparatus 100 of the present invention and/or the central processing computer 20.

The database(s) 20H can also contain and/or include any other data and/or information which is or may be needed and/or desired in performing any and/or all of the features and/or functionality described herein as being generated by, and/or provided by, the apparatus 100 of the present invention and/or described herein as being generated by, and/or provided by, the central processing computer 10 and/or any of the communication devices or computers 10, 30, 40, 50, and/or 60.

The central processing computer 10 also includes an output device(s) 20I for outputting any of the data, information, messages and/or reports, described herein as being generated by or via the central processing computer 20. In the preferred embodiment, the output device(s) 20I can be a printer, a display, a transmitter, a modem, and/or any other device which can be used to output data or information of any kind or type. In the preferred embodiment, the output device(s) 20I is/are also connected to, or linked with, the CPU 20A.

The central processing computer 20 also includes a video and/or audio recording device(s) 20J which can include a camera and/or a video recording device for recording pictures or video and/or video clips and/or a microphone or an audio recording device for recording audio or audio clips which can be recorded by, and/or transmitted live, by or from the central processing computer 20, or which can be recorded by, and stored at or in, the central processing computer 20 for transmission by or from the central processing computer 20 at a later time. The video and/or audio recording device(s) 20J can also be utilized to facilitate one-way broadcasts from the central processing computer 20, and/or can be utilized to facilitate video conferencing, video chatting, and/or audio conferencing, and/or video and audio conferencing, between users of the central processing computer 20 and any of the herein-described users, individuals, providers, or entities, who or which utilize the apparatus 100 and method of the present invention. In the preferred embodiment, the video and/or audio recording device(s) 20J is/are also connected to, or linked with, the CPU 20A.

Figure 5:
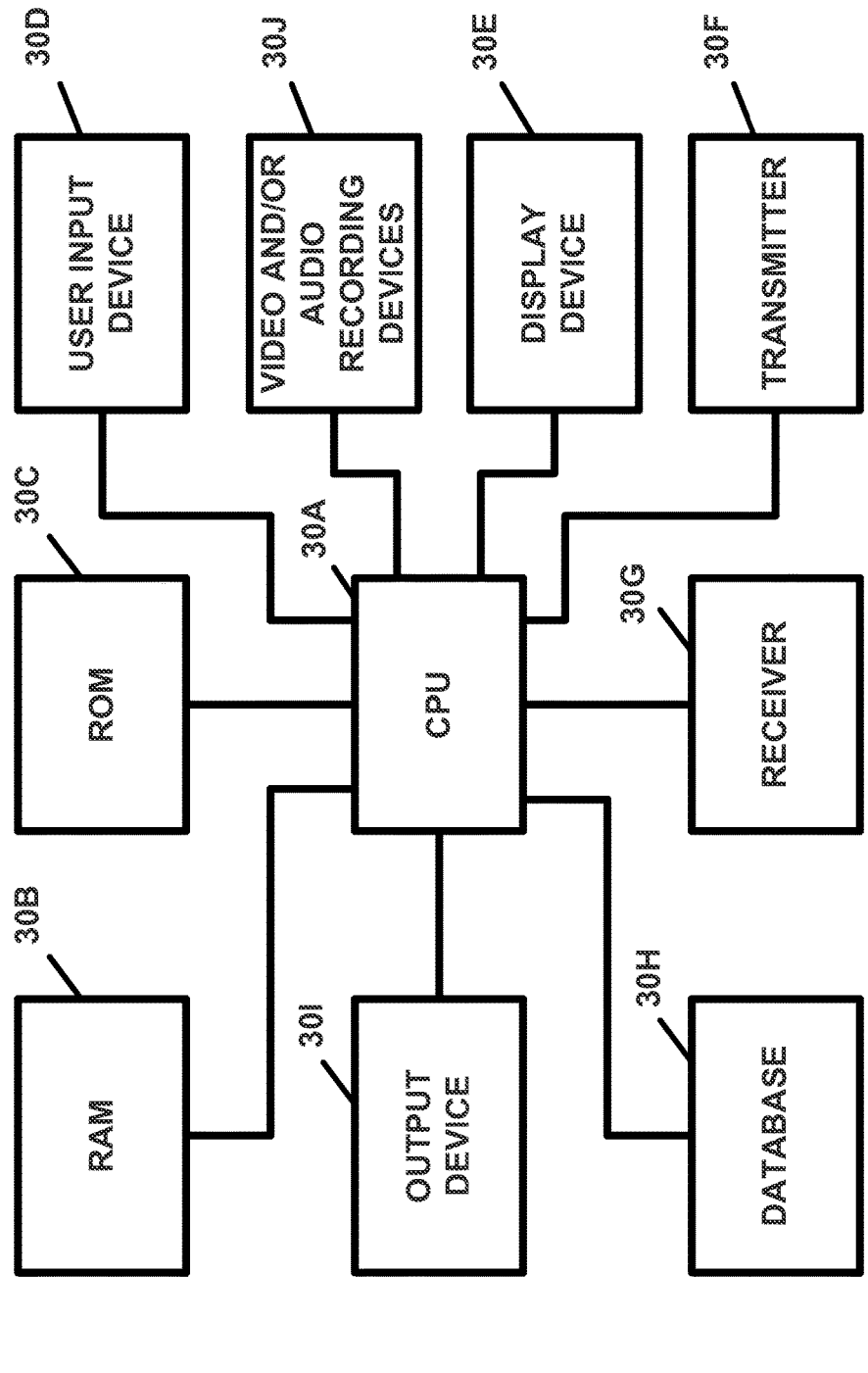
FIG. 5 illustrates the user communication device of FIG. 1, in block diagram form.

FIG. 5 illustrates the user communication device 30 of FIG. 1, in block diagram form. The user communication device 30, in the preferred embodiment, can be a personal computer, a home computer, a laptop computer, a notebook computer, a tablet computer, a tablet, a hand-held computer, a palmtop computer, a personal communication device, a cellular telephone, a wireless telephone, a mobile telephone, a Smartphone, a smartphone, a personal digital assistant, a digital television, an interactive television, a digital television, a telephone, a digital telephone, a television, an interactive television, a beeper, a pager, and/or a watch or a Smart watch, and/or any wearable device, computer or communication device. The user communication device 30 can also be a server computer, or any computer capable of being utilized in a network or capable of being utilized with other computers in a network.

With reference to FIG. 5, in the preferred embodiment, the user communication device 30 includes a central processing unit or CPU 30A, which in the preferred embodiment, is a microprocessor. The CPU 30A can also be a microcomputer, a minicomputer, a macro-computer, and/or a mainframe computer, depending upon the application.

The user communication device 30 also includes a random access memory device(s) 30B (RAM), a read only memory device(s) 30C (ROM), each of which is connected to, or linked with, the CPU 30A, and a user input device 30D, for inputting and/or entering data and/or information and/or instructions and/or commands into the user communication device 30, which can include any one or more of a keyboard, a scanner, a user pointing device, such as, for example, a mouse, a touch pad, and/or an audio input device and/or a video input device, and/or any device, electronic and/or otherwise which can be utilized for inputting and/or entering data and/or information and/or instructions and/or commands into the user communication device 30. The input device(s) 30D is/are also connected to, or linked with, the CPU 30A.

The user communication device 30 also includes a display device 30E for displaying data and/or information to a user or operator. In the preferred embodiment, the display device 30E is also connected to, or linked with, the CPU 30A. The user communication device 30 also includes a transmitter(s) 30F, for transmitting signals and/or data and/or information to any one or more of the personal monitoring device(s) 10, the central processing computer(s) 20, the law enforcement communication device(s) 40, the emergency services provider communication device(s) 50, and/or the healthcare records computer(s) 60, and/or any other user communication device(s) 30, which can be utilized in conjunction with the present invention. In the preferred embodiment, the transmitter(s) 30F is/are also connected to, or linked with, the CPU 30A. The user communication device 30 also includes a receiver(s) 30G, for receiving signals and/or data and/or information from any one or more of the personal monitoring device(s) 10, the central processing computer(s) 20, the law enforcement communication device(s) 40, the emergency services provider communication device(s) 50, and/or the healthcare records computer(s) 60, and/or any other user communication device(s) 30, which can be utilized in conjunction with the present invention. In the preferred embodiment, the receiver(s) 30G is/are also connected to, or linked with, the CPU 30A.

The user communication device 30 also includes a database(s) 30H. In the preferred embodiment, the database(s) 30H is/are also connected to, or linked with, the CPU 30A. The database(s) 30H can contain and/or be linked to any of the data and/or information described herein as being stored in the database(s) 20H as well as any data and/or information described herein as being stored in the database 10H of each user or individual monitored by the user or individual who is associated with, or who uses the user communication device.

The database(s) 30H can contain and/or include data and/or information regarding the user or the individual, or any users or individuals, who or which utilize the user communication device 30, which can include, but which is not limited to, the user's or the individual's, or each user's or each individual's, name, address, telephone number(s), cellular telephone number(s), mobile or wireless telephone number(s), e-mail address or e-mail addresses, and/or text message, instant message, SMS message, or MMS message, IP address(es), or any other messaging, telephone number, or other, address or identifier.

In a preferred embodiment, the database 30H can contain and/or can include any data and/or information, and/or any link or links to any data and/or information, needed or desired for enabling and/or for allowing the user communication device 30H and/or the apparatus 100 and/or any of the computers or communication devices described herein as being utilized in conjunction with the apparatus 100 and method of the present invention to perform any and/or all of the functionality described herein which is capable of being performed by the user communication device 30 and/or the apparatus 100 of the present invention.

In a preferred embodiment, the database 30H can contain and/or can include any software, software programs, algorithms, or software applications ("apps") needed or desired for enabling and/or for allowing the user communication device 30 and/or the apparatus 100 and/or any of the computers or communication devices described herein as being utilized in conjunction with the apparatus 100 and method of the present invention to perform any and/or all of the functionality described herein which is capable of being performed by the user communication device 30 and/or the apparatus 100 of the present invention.

In a preferred embodiment, the database(s) 30H can contain and/or can include any data and/or information regarding the user communication device 30, the name of the user or the individual, or any users or individuals, including, but is not limited to, who utilize the user communication device 30, including, but not limited to, the user's or the individual's name, address, home telephone number, e-mail address, IP address, test messaging number, text messaging address, cellular telephone number, and the telephone number assigned to the user communication device 30, as well as the date of birth, gender, height, weight, identification photograph, social security number or any other suitable identification information, and/or any other data and/or information regarding the user of the user communication device 30.

In a preferred embodiment, the database(s) 30H can contain and/or can include, for each user or individual who is to be monitored or who is being monitored by, with, or using, the user communication device 30, any data and/or information regarding the user or the individual, or any users or individuals, including, but is not limited to, the user's or the individual's name, address, home telephone number, e-mail address, IP address, test messaging number, text messaging address, cellular telephone number, the telephone number assigned to the personal monitoring device 10, date or birth, gender, height, weight, identification photograph, social security number or any other suitable identification information, and/or any other data and/or information regarding the user of the individual being to be monitored or is to be monitored.

The database 30H can also contain and/or can include for each user, individual, or person, who is to be monitored or who is being monitored by, with, or using, the user communication device 30, any data and/or information regarding the user's. the individual's, or the person's, personal monitoring device 10 which can include, but which is not limited to, the type of device, such as for example, a cellular telephone, Smartphone, smartphone, personal digital assistant, or any other device described herein which can be utilized as a personal monitoring device 10, the manufacturing and model number of personal communication device 10, a serial number of the personal monitoring device 10, any other identifying data and/or information assigned to, associated with, or relating to, the personal monitoring device 10, the telephone number associated with, or assigned to, the personal communication device 10, the cellular telephone number associated with, or assigned to, the personal communication device 10, the wireless or mobile telephone number associated with, or assigned to, the personal communication device 10, an IP address associated with, or assigned to, the personal monitoring device 10, an email address associated with, or assigned to the personal monitoring device 10, a text messaging number associated with, or assigned to, the personal monitoring device 10, and/or any other data and/or information associated with the personal monitoring device 10. The database 30H can also contain and/or can include any of the above-described information for any other personal monitoring device(s) 10 or any number of personal monitoring devices 10 which is/are used by the user or individual being monitored or to be monitored.

The database 10H can also contain and/or can include any data and/or information regarding the user or individual who uses the user communication device 30. In a preferred embodiment, the user or individual who is using the user communication device 30 can be, but is not limited to, a parent or parents, spouse, sibling, relative, friend, nanny, au pair, caregiver, teacher, employer, or any other person or entity, of the user or individual being monitored or to be monitored. In a preferred embodiment, the database 30H can contain and/or can include the name, address, telephone number, cellular telephone number, user communication device telephone number or cellular telephone number, e-mail address, IP address, text messaging number, and/or any other data and/or information, and/or contact information, of, for, or regarding, the user or individual who is using the user communication device 30. The database 30H can also contain and/or can include any other data and/or information, described herein as being stored for or regarding the user or individual who uses the user communication device 30.

The database 30H can also contain and/or can include, for each user or individual being monitored by or to be monitored by, with, or using, the user communication device 30, any data and/or information regarding places, locations, or venues, to which each user or individual being monitored by or to be monitored by the user communication device 30, travels. The database 30H can also contain and/or can include data and/or information regarding the daily schedule or daily schedules of or for the each user or individual being monitored by or to be monitored by, with, or using, the user communication device 30, and/or any data and/or information regarding the daily routine or daily routines of or for the each user or individual being monitored by or to be monitored by, with, or using, the user communication device 30, any places where the user or individual being monitored or to be monitored, is or has to be at a given time, and/or any other data and/or information regarding the daily routines, weekly routines, travel routines, travel routes used, alternate travel routes used, travel times and/or time of travel regarding any travel by, the user or individual being monitored or to be monitored, and/or any other data and/or information regarding the routines that can be utilized in performing a personal monitoring service for or regarding each user, individual, or person, being monitored or to be monitored by, with, or using, the user communication device 30.

For example, in the case of a child being monitored by, with, or using, the user communication device 30, the database 30H can contain and/or can include, for that child, any data and/or information regarding the daily weekday schedule for the child such as, for example, the child's home address, the time or approximate time when the child leaves home for school, a preferred travel route the child takes to go to school, any alternate travel routes to the school, the time or the approximate time the child arrives at school or the time school starts for the child, the time or the approximate time the child leaves school or the time school ends for the day, a travel route to an after school activity, if applicable, a travel route to the after school activity, an alternate travel route to the after school activity, a time or an approximate time of a travel to an after school activity, a time or an approximate time when the child leaves the venue of the after school activity, a travel route from the venue of the after school activity to the child's home, a travel route to the child's home, an alternate travel route to the child's home, and/or a time or an approximate time when the child is expected to arrive at home.

As and for another example, in the case of an adult of any age being monitored by, with, or using, the user communication device 30, the database 30H can contain and/or can include, for that adult, any data and/or information regarding the daily weekday schedule for the adult such as, for example, the adult's home address, the time or approximate time when the adult leaves home for work or some other activity or venue, a preferred travel route the adult takes to go to work or some other activity or venue, any alternate travel routes to the work, activity, or venue, the time or the approximate time the adult arrives at work, the activity, or the venue, the time or the approximate time the adult leaves work, the activity, or the venue, a travel route to another activity or venue, if applicable, a travel route to the other activity or venue, an alternate travel route to the other or venue, a time or an approximate time of a travel to the other activity or venue, a time or an approximate time when the adult leaves the other activity or venue, a travel route from the other activity or venue back to the adult's home, a travel route to the adult's home, an alternate travel route to the adult's home, and/or a time or an approximate time when the adult is expected to arrive at home.

The database 30H can also contain and/or can include, for each user, individual, or person, being monitored by, with, or using, the user communication device 30, any data and/or information regarding any school(s), workplace(s), club(s), activity venue(s), recreational venue(s), entertainment venue(s), or any other place(s), location(s), and/or other venue(s), of the respective user, individual, or person, and/or to which the user, individual, or person, travels and/or at which the user, individual, or person, is known to spend time. The database 30H can also contain and/or can include for each user, individual, or person, being monitored by, with, or using, the user communication device 30, any data and/or information regarding the location(s) of any school(s), workplace(s), club(s), activity venue(s), recreational venue(s), entertainment venue(s), or any other place(s), location(s), and/or other venue(s), of the respective user, individual, or person, which data and/or information can include the name, the address, the telephone number, the website address, the IP address, a description of same, schedule information of or for same, and/or any other information regarding same.

The database 30H can also contain and/or can include any data and/or information regarding any weekday or weekend day schedules or itineraries of any user, individual, or person, who is monitored by or is being monitored by, with, or using, the user communication device 30. The database 30H can also contain and/or can include any data and/or information regarding emergency contacts for the user of, or the individual who uses, the user communication device 30, as well as any information regarding any emergency contact for each user, individual, or person, monitored or being monitored by, with, or using, the user communication device 30, including, including, for the user or and/or each user or individual monitored or being monitored by, with, or using, the user communication device 30, any data and/or information regarding each respective emergency contact individual, his or her name, telephone number, cellular telephone number, text messaging number, e-mail address, or IP address, or any other information.

The database 30H can also contain and/or can include any data and/or information regarding any personal monitoring accounts associated with the user communication device 30. The database 30H can also contain and/or can include any data and/or information regarding any persons responsible for monitoring the user or the individual who uses the user communication device 30 as well as any data and/or information regarding the each user, individual, or person, who is to be monitored by, with, or using, the user communication device 30, including, but not limited to, for each user, individual, or person, his or her name, telephone number, cellular telephone number, text messaging number, e-mail address, or IP address, or any other information. The database 30H can also contain and/or can include any data and/or information regarding any and/or all personal monitoring devices 10 assigned to or associated with the user communication device 30 and/or can contain and/or can include any data and/or information regarding with any personal monitoring accounts which are associated with, or which can be monitored or serviced by, the user communication device 30.

The database 30H can also contains and/or can include any data and/or information regarding any of the personal monitoring devices 10, any central processing computer(s) 20, any other user communication device(s) 30, any law enforcement communication device(s) 40, any emergency services provider communication device(s) 50, and/or the healthcare records computer(s) 60, described herein, and/or can contain and/or can include any link(s) or hyperlink(s) to same.

The database 30H can also contain and/or can include an electronic healthcare record of the user or the individual who is using the user communication device 30, as well an electronic healthcare record of each user, individual, or person, monitored by, with, or using, the user communication device 30, as well as any data and/or information which may be contained in the electronic healthcare record of each respective user or individual, any personal healthcare record of each respective user or individual, any data and/or information which may be contained in the personal healthcare record of each respective user or individual, any healthcare information regarding each respective user or individual, any information regarding any healthcare condition or special needs of each respective user or individual, any information regarding any medicines, prescribed medications, drugs, or prescribed drugs, which are needed by each respective user or individual, any information regarding any allergies of each respective user or individual, or any other information regarding any healthcare conditions, needs, or treatments, of, for, or regarding, each respective user or individual. The database 30H can also contain and/or can include a link or hyperlink to the healthcare records computer 60 and/or to any pertinent records, data, and/or information, stored therein.

The database 30H can also contain and/or can include data and/or information regarding the daily schedule for each weekday or each weekend day for the each user, individual, or person, monitored by, with, or using, the user communication device 30, travel routes travelled for each day and trip, and/or time(s) associated with each trip or travel segment of each trip.

The database 30H can also contain and/or can include, for any user, individual, or person, monitored by, with, or using, the user communication device 30, any data and/or information regarding the name, address, telephone number(s), cellular telephone number(s), mobile or wireless telephone number(s), e-mail address(es), text messaging address(es), IP address(es), or any other contact information for or regarding the user, individual, or person, or any users or individuals authorized to monitor that user, individual, or person.

It is important to note, as used throughout the application, the term or phrase "text messaging number" includes any and all kinds of messaging numbers, including, but not limited to, a text messaging number, an SMS messaging number, and MMS messaging number, or any other number, address, or identifier, used or needed in order to send a text message or any other message to any user, individual, person, or entity who or which uses the apparatus 100 of the present invention.

The database 30H can also contain and/or include any software, software program(s), algorithm(s), or software applications ("apps"), such as those known by those skilled in the art at the time of the filing of this application, which can be downloaded at any time to the user communication device 30, and which can allow the user communication device 30 to ascertain, determine, locate, and/or display, a location or position of any personal monitoring device 10 used by or associated with any user or individual who is being monitoring by the user or individual who is using or who is associated with the user communication device 30.

The database 30H can also contain and/or can include navigation software for allowing the user communication device 30 to calculate travel routes, for the user or individual using the user communication device 30, as well as for each and/or any user, individual, or person, or their personal monitoring device 10, which is monitored or being monitored, by, with, or using, the user communication device 30, for travel from one place or point to another, to detect departures from a travel route and to re-calculate another travel route, and/or for allowing the user communication device 30 to calculate and/or store travel routes and/or any data and/or information regarding same as well as alternate travel routes for same. The database 30H can also contain and/or can include any data and/or information regarding allowed travel routes for any user, individual, or person, monitored or being monitored, by, with, or using, the user communication device 30, as well as any disallowed travel routes for the user, individual, or person, monitored or being monitored, by, with, or using, the user communication device 30. The database 30H can also contain and/or can include map data and/or map information including, but not limited to, digitized map data and/or information and/or data and/or information for updating any map data and/or information.

The database 30H can also contain and/or include, for any user, individual, or person, monitored or being monitored, by, with, or using, the user communication device 30, any data and/or information regarding travel records for each respective user, individual, or person, which can contain and/or include data and/or information regarding a date and time of travel and/or travel routes taken or travelled by, and/or any other data and/or information regarding, the respective user, individual, or person, for or during any period of time or during and/or for or relating to any schedule or routine.

The database 30H can also contain and/or include a pre-recorded audio message(s) and/or a pre-recorded audio and video message(s), which can be recorded by any person authorized to monitor the user or individual and which can be uploaded to the central processing computer 20, and/or which can be transmitted to the personal monitoring device 10, at any time, and which can be provided at and/or via the personal monitoring device 10 at any time and/or for any reason. For example, an audio and/or an audio and video recording can be played via the personal monitoring device 10 in order to assist, calm, or comfort, a lost child, to help re-orient a child, to give or provide the child or any one with whom the child comes into contact with, instructions, contact information, emergency contact information, directions, or any other information, and/or can be played to clam, comfort, or assist, a lost, disoriented, or ill, adult or child of any age, or to give or provide the child or any one with whom the child comes into contact with, instructions, contact information, emergency contact information, directions, or any other information.

The database 30H can also contain and/or include any data and/or information, and/or any software, software programs, algorithms, or software applications for controlling and/or monitoring any operation or function of any personal monitoring device 10 associated with any user of individual who is monitored or being monitored by, with, or using, the user communication device 30. The database 30H can also contain and/or include any data and/or information, and/or any software, software programs, algorithms, or software applications for tracking the position, location, or whereabouts, of any personal monitoring device 10 associated with any user of individual who is monitored or to be monitored by, with, or using, the user communication device 30.

The database 30H can also contain and/or can include any data, information, software, software programs, algorithms, and/or software applications (or "apps") which are needed or desired for allowing the user communication device 30 to perform any and/or all of the functions and/or functionality described herein as being capable of being performed by same and/or by the apparatus 100 and method of the present invention.

The database 30H can also contain and/or can include any of the data and/or information described herein as being stored in any of the other databases 10H, 20H, 30H, 40H, 50H, and/or 60H, described herein.

The user communication device 30 also includes an output device(s) 301 for outputting any of the data, information, and/or reports, described herein as being generated by or via the user communication device 30. In the preferred embodiment, the output device(s) 301 can be a display screen, a speaker, a printer, a display of any type or kind, an indicator light, a transmitter, a modem, and/or any other device which can be used to output data or information of any kind or type. In the preferred embodiment, the output device(s) 301 is/are also connected to, or linked with, the CPU 30A.

The user communication device 30 also includes a video and/or audio recording device(s) 30J which can include a camera and/or a video recording device for recording pictures or video and/or video clips and/or a microphone or an audio recording device for recording audio or audio clips which can be recorded by, and/or transmitted live, by or from the user communication device 30, or which can be recorded by, and stored at or in, the user communication device 30 for transmission by or from the user communication device 30 at a later time. The video and/or audio recording device(s) 30J can be utilized to facilitate video conferencing, video chatting, and/or audio conferencing, and/or video and audio conferencing, between users of the user communication device 30 and any user of any other computer or communication device 10, 20, 30, 40, 50, or 60, described herein. In the preferred embodiment, the video and/or audio recording device(s) 30J is/are also connected to, or linked with, the CPU 30A.

In another preferred embodiment, the user communication device 30 can also include a "kill" switch or associated hardware and/or software (not shown) for disabling and/or deactivating the user communication device 30 in instances when same might be lost or stolen, so as to prevent its use by another person and/or to prevent any access to any data and/or information stored therein, thereby rendering the user communication device 30 useless to another person after being reported, or being discovered, as being lost or stolen.

Figure 6:
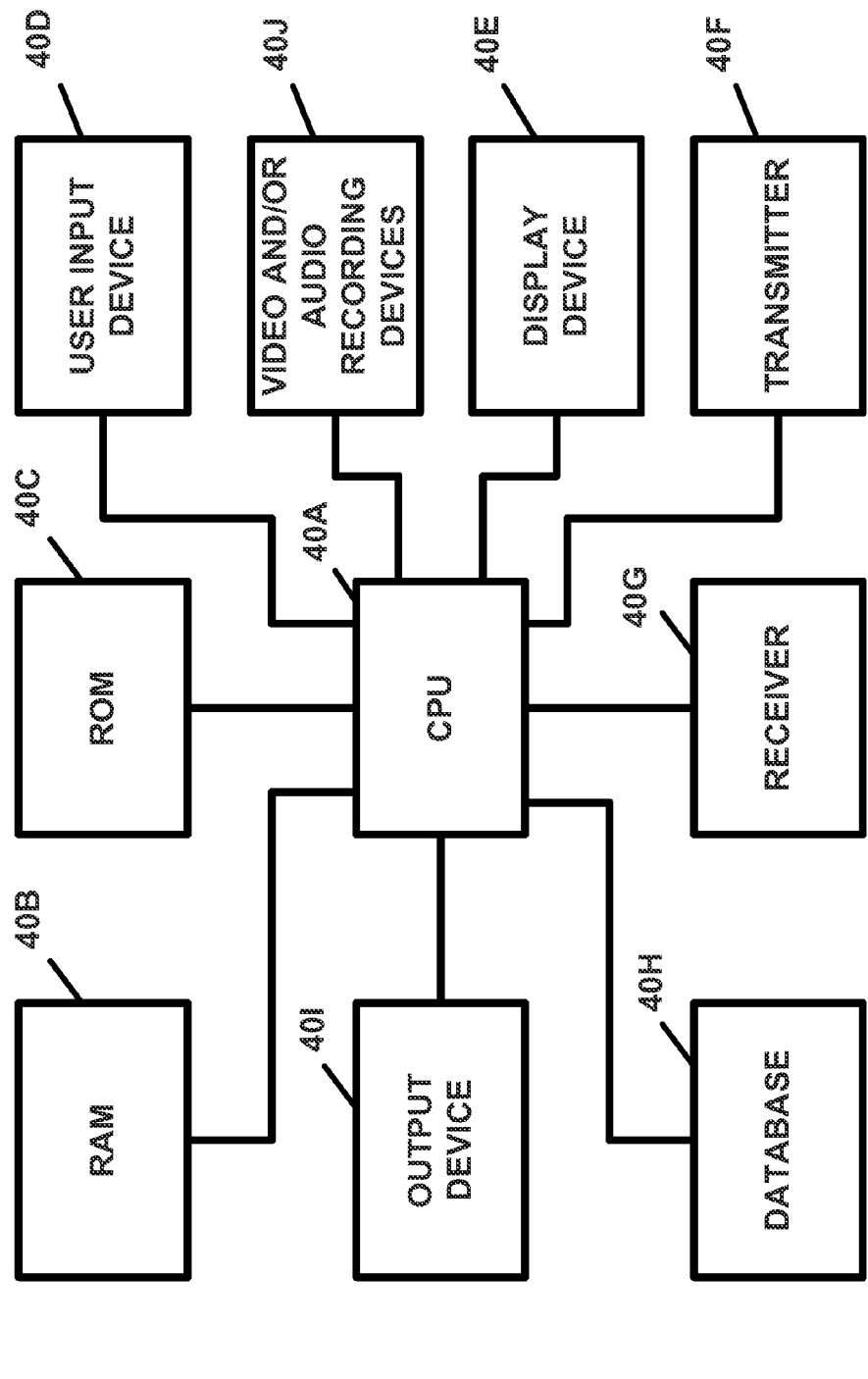
FIG. 6 illustrates the law enforcement communication device of FIG. 1, in block diagram form.

FIG. 6 illustrates the law enforcement communication device 40 of FIG. 1, in block diagram form. The law enforcement communication device 40, in the preferred embodiment, can be a personal computer, a home computer, a laptop computer, a notebook computer, a tablet computer, a tablet, a hand-held computer, a palmtop computer, a personal communication device, a cellular telephone, a wireless telephone, a mobile telephone, a Smartphone, a smartphone, a personal digital assistant, a digital television, an interactive television, a digital television, a telephone, a digital telephone, a television, an interactive television, a beeper, a pager, and/or a watch or a Smart watch, and/or any wearable device, computer or communication device. The law enforcement communication device 40 can also be a server computer, or any computer capable of being utilized in a network or capable of being utilized with other computers in a network.

With reference to FIG. 6, in the preferred embodiment, the law enforcement communication device 40 includes a central processing unit or CPU 40A, which in the preferred embodiment, is a microprocessor. The CPU 40A can also be a microcomputer, a minicomputer, a macro-computer, and/or a mainframe computer, depending upon the application.

The law enforcement communication device 40 also includes a random access memory device(s) 40B (RAM), a read only memory device(s) 40C (ROM), each of which is connected to, or linked with, the CPU 40A, and a user input device 40D, for inputting and/or entering data and/or information and/or instructions and/or commands into the law enforcement communication device 40, which can include any one or more of a keyboard, a scanner, a user pointing device, such as, for example, a mouse, a touch pad, and/or an audio input device and/or a video input device, and/or any device, electronic and/or otherwise which can be utilized for inputting and/or entering data and/or information and/or instructions and/or commands into the law enforcement communication device 40. The input device(s) 40D is/are also connected to, or linked with, the CPU 40A.

The law enforcement communication device 40 also includes a display device 40E for displaying data and/or information to a user or operator. In the preferred embodiment, the display device 40E is also connected to, or linked with, the CPU 40A. The law enforcement communication device 40 also includes a transmitter(s) 40F, for transmitting signals and/or data and/or information to any one or more of the personal monitoring device(s) 10, the central processing computer(s) 20, the user communication device(s) 30, the emergency services provider communication device(s) 50, and/or the healthcare records computer(s) 60, and/or any other the law enforcement communication device(s) 40, which can be utilized in conjunction with the present invention. In the preferred embodiment, the transmitter(s) 40F is/are also connected to, or linked with, the CPU 40A. The law enforcement communication device 40 also includes a receiver(s) 40G, for receiving signals and/or data and/or information from any one or more of the personal monitoring device(s) 10, the central processing computer(s) 20, the user communication device(s) 30, the emergency services provider communication device(s) 50, and/or the healthcare records computer(s) 60, and/or any other law enforcement communication device(s) 40, which can be utilized in conjunction with the present invention. In the preferred embodiment, the receiver(s) 40G is/are also connected to, or linked with, the CPU 40A.

The law enforcement communication device 40 also includes a database(s) 40H. In the preferred embodiment, the database(s) 40H is/are also connected to, or linked with, the CPU 40A. The database(s) 40H can contain and/or include, and/or can contain and/or include a link(s) or hyperlink(s) to, and/or can be linked to or with, any of the data and/or information described herein as being stored in the database(s) 10H, 20H, and/or 30H, for any user or individual monitored, or to be monitored, by, with, or using, the apparatus 100 of the present invention and/or for any personal monitoring account being serviced by the apparatus 100 of the present invention. The database(s) 40H can also contain and/or include, and/or can contain and/or include a link(s) or hyperlink(s) to, and/or can be linked to or with, any of the data and/or information described herein as being stored in the database(s) 10H, 20H, and/or 30H, for or regarding any user or individual who or which uses a user communication device 30 to monitor another user or individual. The database(s) 40H can also contain and/or include, and/or can contain and/or include a link(s) or hyperlink(s) to, and/or can be linked to or with, any of the data and/or information described herein as being stored in the database(s) 10H, 20H, and/or 30H, for or regarding any user or individual who or which uses a personal monitoring device 10 to allow himself or herself to be monitored by another user or individual via the apparatus 100 and method of the present invention.

The database(s) 40H can also contain and/or include any data and/or information regarding the user or the individual, or any users or individuals, who or which utilize any user communication device 30 or any user or individual who utilizes a personal monitoring device 10, which can include, but which is not limited to, the user's or the individual's, or each user's or each individual's, name, address, telephone number(s), cellular telephone number(s), mobile or wireless telephone number(s), e-mail address or e-mail addresses, and/or text message, instant message, SMS message, or MMS message, or any other messaging, telephone number or other address or identifier.

The database 40H can also contain and/or include any other data and/or information, and/or any software. software programs, algorithms, and/or software applications, described herein or otherwise, which are needed or desired for enabling the law enforcement communication device 40 to perform any and/or all of the functions and/or functionality described herein as being performed by same.

The law enforcement communication device 40 also includes an output device(s) 40I for outputting any of the data, information, and/or reports, described herein as being generated by or via the law enforcement communication device(s) 40. In the preferred embodiment, the output device 40I can be a display screen, a speaker, a printer, a display of any type or kind, an indicator light, a transmitter, a modem, and/or any other device which can be used to output data or information of any kind or type. In the preferred embodiment, the output device(s) 40I is/are also connected to, or linked with, the CPU 40A.

The law enforcement communication device 40 also includes a video and/or audio recording device(s) 40J which can include a camera and/or a video recording device for recording pictures or video and/or video clips and/or a microphone or an audio recording device for recording audio or audio clips which can be recorded by, and/or transmitted live, by or from the law enforcement communication device 40, or which can be recorded by, and stored at or in, the law enforcement communication device 40 for transmission by or from the law enforcement communication device 40 at a later time. The video and/or audio recording device(s) 40J can be utilized to facilitate video conferencing, video chatting, and/or audio conferencing, and/or video and audio conferencing, between users of the law enforcement communication device 40 and any user of any other computer or communication device 10, 20, 30, 40, 50, or 60, described herein. The video and/or audio recording device(s) 40J can also be utilized to facilitate one-way broadcasts from the law enforcement communication device 40. In the preferred embodiment, the video and/or audio recording device(s) 40J is/are also connected to, or linked with, the CPU 40A.

Figure 7:
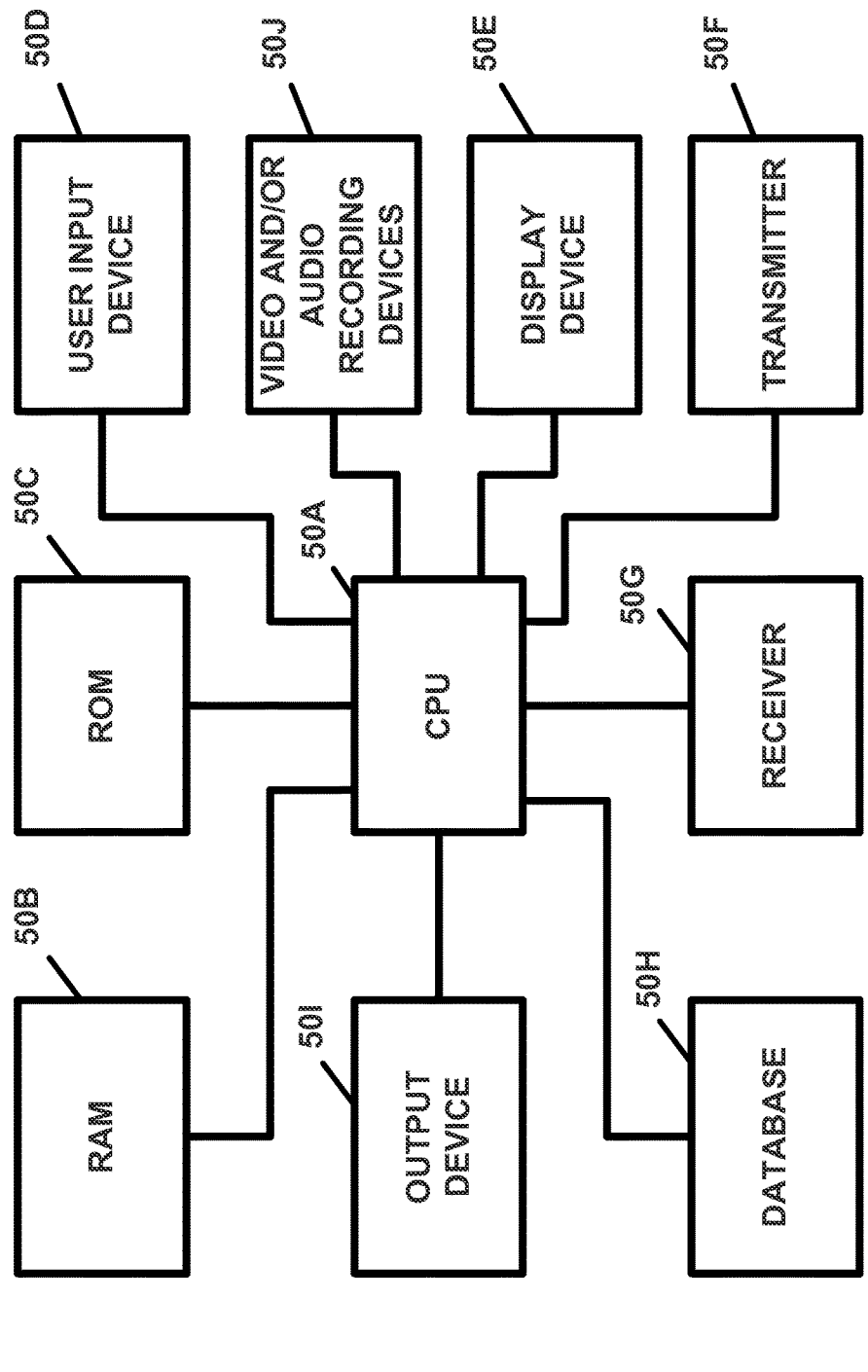
FIG. 7 illustrates the emergency services provider communication device of FIG. 1, in block diagram form.

FIG. 7 illustrates the emergency services provider communication device 50 of FIG. 1, in block diagram form. The emergency services provider communication device 50, in the preferred embodiment, can be a personal computer, a home computer, a laptop computer, a notebook computer, a tablet computer, a tablet, a hand-held computer, a palmtop computer, a personal communication device, a cellular telephone, a wireless telephone, a mobile telephone, a Smartphone, a smartphone, a personal digital assistant, a digital television, an interactive television, a digital television, a telephone, a digital telephone, a television, an interactive television, a beeper, a pager, and/or a watch or a Smart watch, and/or any wearable device, computer or communication device. The emergency services provider communication device 50 can also be a server computer, or any computer capable of being utilized in a network or capable of being utilized with other computers in a network.

With reference to FIG. 7, in the preferred embodiment, the emergency services provider communication device 50 includes a central processing unit or CPU 50A, which in the preferred embodiment, is a microprocessor. The CPU 50A can also be a microcomputer, a minicomputer, a macrocomputer, and/or a mainframe computer, depending upon the application.

The emergency services provider communication device 50 also includes a random access memory device(s) 50B (RAM), a read only memory device(s) 50C (ROM), each of which is connected to, or linked with, the CPU 50A, and a user input device 50D, inputting and/or entering data and/or information and/or instructions and/or commands into the emergency services provider communication device 50, which can include any one or more of a keyboard, a scanner, a user pointing device, such as, for example, a mouse, a touch pad, and/or an audio input device and/or a video input device, and/or any device, electronic and/or otherwise which can be utilized for inputting and/or entering data and/or information and/or instructions and/or commands into the emergency services provider communication device 50. The input device(s) 50D is/are also connected to, or linked with, the CPU 50A.

The emergency services provider communication device 50 also includes a display device 50E for displaying data and/or information to a user or operator. In the preferred embodiment, the display device 50E is also connected to, or linked with, the CPU 50A. The emergency services provider communication device 50 also includes a transmitter(s) 50F, for transmitting signals and/or data and/or information to any one or more of the personal monitoring device(s) 10, the central processing computer(s) 20, the user communication device(s) 30, the law enforcement communication device(s) 40, and/or the healthcare records computer(s) 60, and/or any other emergency services provider communication device(s) 50, which can be utilized in conjunction with the present invention. In the preferred embodiment, the transmitter(s) 50F is/are also connected to, or linked with, the CPU 50A. The emergency services provider communication device(s) 50 also includes a receiver(s) 50G, for receiving signals and/or data and/or information from any one or more of the personal monitoring device(s) 10, the central processing computer(s) 20, the user communication device(s) 30, law enforcement communication device(s) 40, and/or the healthcare records computer(s) 60, and/or any other the emergency services provider communication device(s) 50, which can be utilized in conjunction with the present invention. In the preferred embodiment, the receiver(s) 50G is/are also connected to, or linked with, the CPU 50A.

The emergency services provider communication device 50 also includes a database(s) 50H. In the preferred embodiment, the database(s) 50H is/are also connected to, or linked with, the CPU 50A. The database(s) 50H can contain and/or include, and/or can contain and/or include a link(s) or hyperlink(s) to, and/or can be linked to or with, any of the data and/or information described herein as being stored in the database(s) 10H, 20H, and/or 30H, for any user or individual monitored, or to be monitored, by, with, or using, the apparatus 100 of the present invention and/or for any personal monitoring account being serviced by the apparatus 100 of the present invention. The database(s) 50H can also contain and/or include, and/or can contain and/or include a link(s) or hyperlink(s) to, and/or can be linked to or with, any of the data and/or information described herein as being stored in the database(s) 10H, 20H, and/or 30H, for or regarding any user or individual who or which uses a user communication device 30 to monitor another user or individual. The database(s) 50H can also contain and/or include, and/or can contain and/or include a link(s) or hyperlink(s) to, and/or can be linked to or with, any of the data and/or information described herein as being stored in the database(s) 10H, 20H, and/or 30H, for or regarding any user or individual who or which uses a personal monitoring device 10 to allow himself or herself to be monitored by another user or individual via the apparatus 100 and method of the present invention.

The database(s) 50H can also contain and/or include any data and/or information regarding the user or the individual, or any users or individuals, who or which utilize any user communication device 30 or any user or individual who utilizes a personal monitoring device 10, which can include, but which is not limited to, the user's or the individual's, or each user's or each individual's, name, address, telephone number(s), cellular telephone number(s), mobile or wireless telephone number(s), e-mail address or e-mail addresses, and/or text message, instant message, SMS message, or MMS message, or any other messaging, telephone number or other address or identifier.

The database 50H can also contain and/or include any other data and/or information, and/or any software. software programs, algorithms, and/or software applications, described herein or otherwise, which are needed or desired for enabling the emergency services provider communication device 50 to perform any and/or all of the functions and/or functionality described herein as being performed by same.

The emergency services provider communication device 50 also includes an output device(s) 50I for outputting any of the data, information, and/or reports, described herein as being generated by or via the emergency services provider communication device 50. In the preferred embodiment, the output device(s) 50I can be a display screen, a speaker, a printer, a display of any type or kind, an indicator light, a transmitter, a modem, and/or any other device which can be used to output data or information of any kind or type. In the preferred embodiment, the output device(s) 50I is/are also connected to, or linked with, the CPU 50A.

The emergency services provider communication device 50 also includes a video and/or audio recording device(s) 50J which can include a camera and/or a video recording device for recording pictures or video and/or video clips and/or a microphone or an audio recording device for recording audio or audio clips which can be recorded by, and/or transmitted live, by or from the emergency services provider communication device 50, or which can be recorded by, and stored at or in, the emergency services provider communication device 50 for transmission by or from the emergency services provider communication device 50 at a later time. The video and/or audio recording device(s) 50J can be utilized to facilitate video conferencing, video chatting, and/or audio conferencing, and/or video and audio conferencing, between users of the emergency services provider communication device 50 and any user of any other computer or communication device 10, 20, 30, 40, 50, or 60, described herein. The video and/or audio recording device(s) 50J can also be utilized to facilitate one-way broadcasts from the emergency services provider communication device 50. In the preferred embodiment, the video and/or audio recording device(s) 50J is/are also connected to, or linked with, the CPU 50A.

Figure 8:
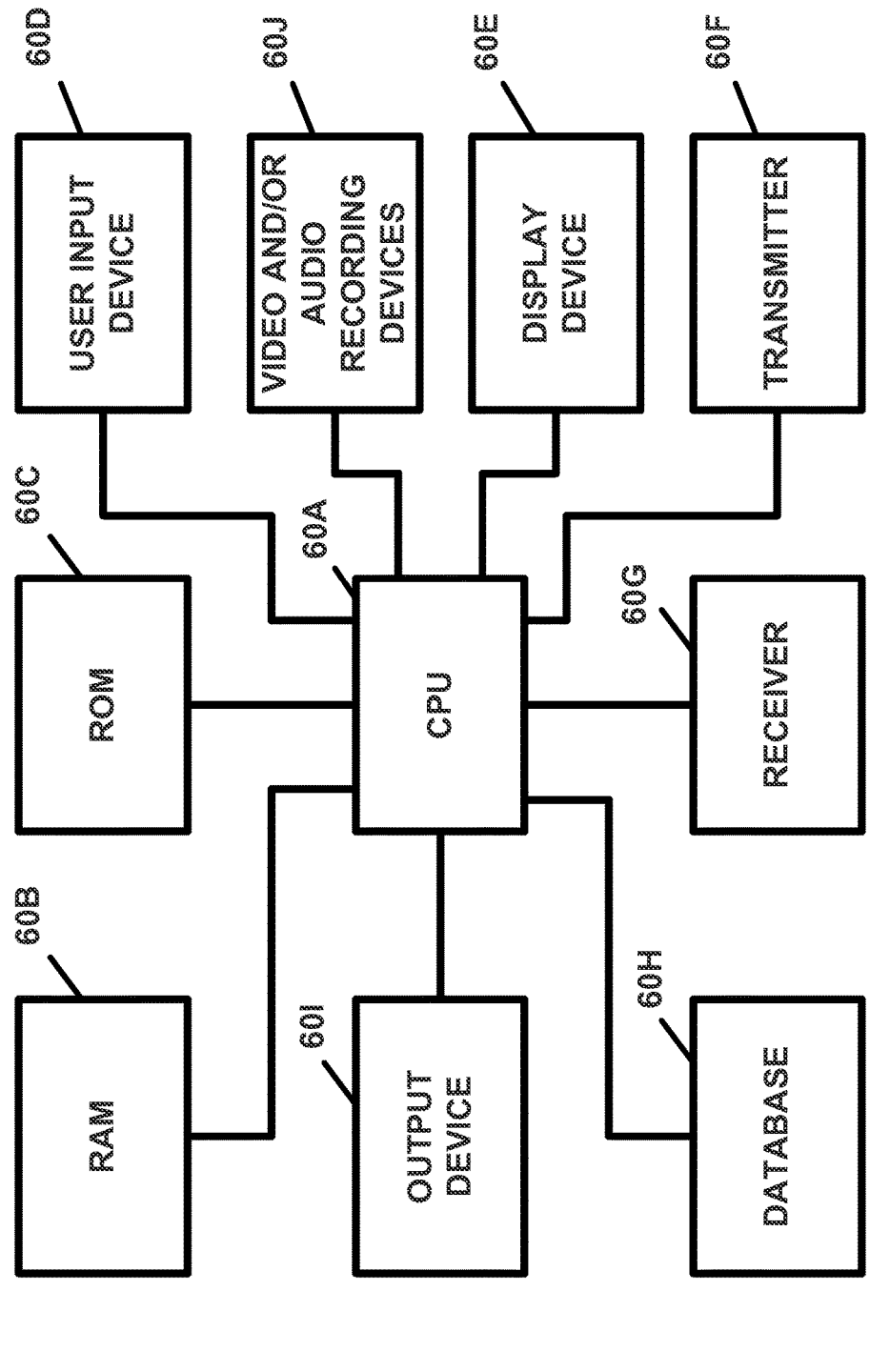
FIG. 8 illustrates the healthcare records computer of FIG. 1, in block diagram form.

FIG. 8 illustrates the healthcare records computer 60 of FIG. 1, in block diagram form. The healthcare records computer 60, in a preferred embodiment, can also be any computer or computer system, or any group of computers. The healthcare records computer 60, in the preferred embodiment, can also be a personal computer, a home computer, a laptop computer, a notebook computer, a tablet computer, a tablet, a hand-held computer, a palmtop computer, a personal communication device, a cellular telephone, a wireless telephone, a mobile telephone, a Smartphone, a smartphone, a personal digital assistant, a digital television, an interactive television, a digital television, a telephone, a digital telephone, a television, an interactive television, a beeper, a pager, and/or a watch or a Smart watch, and/or any wearable device, computer or communication device. The healthcare records computer 60 can also be server computer, or any computer capable of being utilized in a network or capable of being utilized with other computers in a network.

With reference to FIG. 8, in the preferred embodiment, the healthcare records computer 60 includes a central processing unit or CPU 60A, which in the preferred embodiment, is a microprocessor. The CPU 60A can also be a microcomputer, a minicomputer, a macro-computer, and/or a mainframe computer, depending upon the application.

The healthcare records computer 60 also includes a random access memory device(s) 60B (RAM), a read only memory device(s) 60C (ROM), each of which is connected to, or linked with, the CPU 60A, and a user input device 60D, for inputting and/or entering data and/or information and/or instructions and/or commands into the healthcare records computer 60, which can include any one or more of a keyboard, a scanner, a user pointing device, such as, for example, a mouse, a touch pad, and/or an audio input device and/or a video input device, and/or any device, electronic and/or otherwise which can be utilized for inputting and/or entering data and/or information and/or instructions and/or commands into the healthcare records computer 60. The input device(s) 60D is/are also connected to, or linked with, the CPU 60A.

The healthcare records computer 60 also includes a display device 60E for displaying data and/or information to a user or operator. In the preferred embodiment, the display device 60E is also connected to, or linked with, the CPU 60A. The healthcare records computer 60 also includes a transmitter(s) 60F, for transmitting signals and/or data and/or information to any one or more of the personal monitoring device(s) 10, the central processing computer(s) 20, the user communication device(s) 30, the law enforcement communication device(s) 40, the emergency services provider communication device(s) 50, and/or any other healthcare records computer(s) 60, which can be utilized in conjunction with the present invention. In the preferred embodiment, the transmitter(s) 60F is/are also connected to, or linked with, the CPU 60A. The healthcare records computer 60 also includes a receiver(s) 60G, for receiving signals and/or data and/or information from any one or more of the personal monitoring device(s) 10, the central processing computer(s) 20, the user communication device(s) 30, the law enforcement communication device(s) 40, the emergency services provider communication device(s) 50, and/or any other healthcare records computer(s) 60, which can be utilized in conjunction with the present invention. In the preferred embodiment, the receiver(s) 60G is/are also connected to, or linked with, the CPU 60A.

The healthcare records computer 60 also includes a database(s) 60H. In the preferred embodiment, the database(s) 60H is/are also connected to, or linked with, the CPU 60A. The database(s) 60H can contain and/or include, and/or can contain and/or include a link(s) or hyperlink(s) to, and/or can be linked to or with, any of the data and/or information described herein as being stored in the database(s) 10H, 20H, and/or 30H, for any user or individual monitored, or to be monitored, by, with, or using, the apparatus 100 of the present invention and/or for any personal monitoring account being serviced by the apparatus 100 of the present invention. The database(s) 60H can also contain and/or include, and/or can contain and/or include a link(s) or hyperlink(s) to, and/or can be linked to or with, any of the data and/or information described herein as being stored in the database(s) 10H, 20H, and/or 30H, for or regarding any user or individual who or which uses a user communication device 30 to monitor another user or individual. The database(s) 60H can also contain and/or include, and/or can contain and/or include a link(s) or hyperlink(s) to, and/or can be linked to or with, any of the data and/or information described herein as being stored in the database(s) 10H, 20H, and/or 30H, for or regarding any user or individual who or which uses a personal monitoring device 10 to allow himself or herself to be monitored by another user or individual via the apparatus 100 and method of the present invention.

The database 60H can also contain and/or include, for each user or individual monitored, or to be monitored, by, with, or using, the apparatus 100 of the present invention, and for each user or individual who is monitoring, or who is to be monitoring, any other user or individual, an electronic healthcare record, an electronic medical record, an electronic dental record, a healthcare record, and/or a personal healthcare record, for the respective user or individual, which can include any data and/or information typically found in any electronic healthcare records, electronic medical records, electronic dental records, healthcare records, and/or personal healthcare records. The database 60H can also include for each user or individual, information regarding any healthcare conditions of the user or individual, any medicines, medications, or drugs, the user or individual is taking or required to take, any allergies the user or individual may have, and/or any other information which may be needed or useful for the user's or the individual's well being.

The database(s) 60H can also contain and/or include any data and/or information regarding the user or the individual, or any users or individuals, who or which utilize any user communication device 30 or any user or individual who utilizes a personal monitoring device 10, which can include, but which is not limited to, the user's or the individual's, or each user's or each individual's, name, address, telephone number(s), cellular telephone number(s), mobile or wireless telephone number(s), e-mail address or e-mail addresses, and/or text message, instant message, SMS message, or MMS message, or any other messaging, telephone number or other address or identifier.

The database 60H can also contain and/or include any other data and/or information, and/or any software. software programs, algorithms, and/or software applications, described herein or otherwise, which are needed or desired for enabling the healthcare records computer 60 to perform any and/or all of the functions and/or functionality described herein as being performed by same.

The healthcare records computer 60 also includes an output device(s) 60I for outputting any of the data, information, and/or reports, described herein as being generated by or via the healthcare records computer 60. In the preferred embodiment, the output device(s) 60I can be a display screen, a speaker, a printer, a display of any type or kind, an indicator light, a transmitter, a modem, and/or any other device which can be used to output data or information of any kind or type. In the preferred embodiment, the output device(s) 60I is/are also connected to, or linked with, the CPU 60A.

The healthcare records computer 60 also includes a video and/or audio recording device(s) 60J which can include a camera and/or a video recording device for recording pictures or video and/or video clips and/or a microphone or an audio recording device for recording audio or audio clips which can be recorded by, and/or transmitted live, by or from the healthcare records computer 60, or which can be recorded by, and stored at or in, the healthcare records computer 60 for transmission by or from the healthcare records computer 60 at a later time. The video and/or audio recording device(s) 60J can be utilized to facilitate video conferencing, video chatting, and/or audio conferencing, and/or video and audio conferencing, between users of the healthcare records computer 60 and any user of any other computer or communication device 10, 20, 30, 40, 50, or 60, described herein. The video and/or audio recording device(s) 60J can also be utilized to facilitate one-way broadcasts from the healthcare records computer 60. In the preferred embodiment, the video and/or audio recording device(s) 60J is/are also connected to, or linked with, the CPU 60A.

In a preferred embodiment, the apparatus 100 and method of the present invention can be utilized to monitor an individual or individuals of any age. In this regard, the apparatus 100 and/or the personal monitoring device 10 can be utilized to monitor any child, infant, teenager or young adult, adult of any age, and/or elderly individual. In a preferred embodiment, the apparatus 100 apparatus 100 and/or the personal monitoring device 10 can also be utilized to monitor any child, infant, teenager or young adult, adult of any age, and/or elderly individual, who may or may not be inflicted with a condition, illness, or disease, or who may or may not be inflicted with autism, Alzheimer's disease, memory loss, or be ill with any temporary or permanent illness, sickness, disease, or condition. In a preferred embodiment, the apparatus 100 apparatus 100 and/or the personal monitoring device 10 can also be utilized to monitor any child, infant, teenager or young adult, adult of any age, and/or elderly individual, as a safety precaution.

In a preferred embodiment, any user or individual who utilizes a personal monitoring device 10, or who has a personal monitoring device 10 assigned to him or her, or who has a personal monitoring device 10 associated with him or her, can be referred to herein, or can be defined herein as being, a "monitored individual". In a preferred embodiment, any user or individual who utilizes a user communication device 30 to monitor a monitored individual can be referred to herein, or can be defined herein as being, a "monitoring individual".

In a preferred embodiment, it is envisioned that a personal monitoring device 10 can be programmed with, or can have stored therein or therewith, information regarding the monitored individual's home address, residence address, school residence address or place, workplace address, or other address, place, or location, which is considered to be that monitored individual's place of safety or "home base" or "safe location". In a preferred embodiment, it is envisioned that the personal monitoring device 10 can be programmed with, or can have stored therein or therewith, information regarding any address(es), place(s), or location(s), to which the monitored individual typically travels on a daily basis. For example, the personal monitoring device 10 can be programmed with, or have stored therein or therewith, information regarding the monitored individual's school address, place, or location, workplace address, place, or location, employment address, place, or location, activity or event address, place, or location, or any other address, place, or location, to which the monitored individual is known to travel on a weekday basis, on a weekend daily basis, or on any daily basis.

In a preferred embodiment, the personal monitoring device 10 can also be programmed with the monitored individual's travel itineraries and/or travel schedules for traveling to and between one address, place, or location to another address, place, or location. In a preferred embodiment, the personal monitoring device 10 can also be programmed with travel routes or directions for traveling to and between one address, place, or location to another address, place, or location. In a preferred embodiment, the personal monitoring device 10 can also be programmed with software programs, navigation programs, or any algorithms or software applications, for identifying, determining, ascertaining, or calculating, any travel routes or directions for traveling to and between one address, place, or location to another address, place, or location.

In a preferred embodiment, the personal monitoring device 10 can be utilized in connection with, or in conjunction with, the apparatus 100, the central processing computer 20, a user communication device 30 associated with, or used by, any user or individual authorized to, or assigned to, monitor the monitored individual, any law enforcement communication device 40, and/or any emergency services provider communication device 50. In another preferred embodiment, the personal monitoring device 10 can also be utilized as a stand-alone device by the monitored individual to allow the monitored individual to monitor his or her travels, whereabouts, or environment.

Figure 9A:
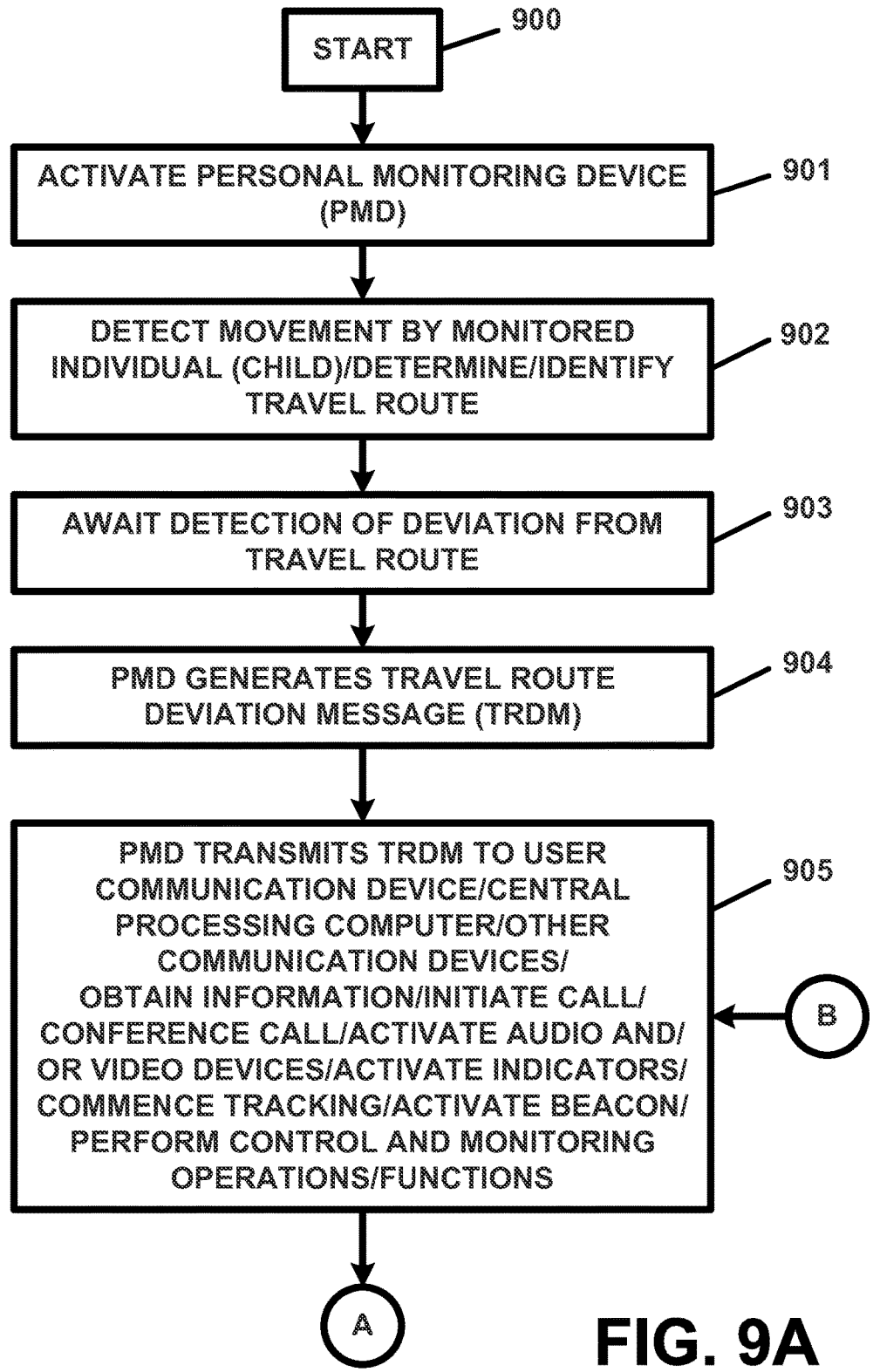
FIGS. 9A and 9B illustrate a preferred embodiment method for utilizing the apparatus of the present invention, in flow diagram form.
Figure 9B:
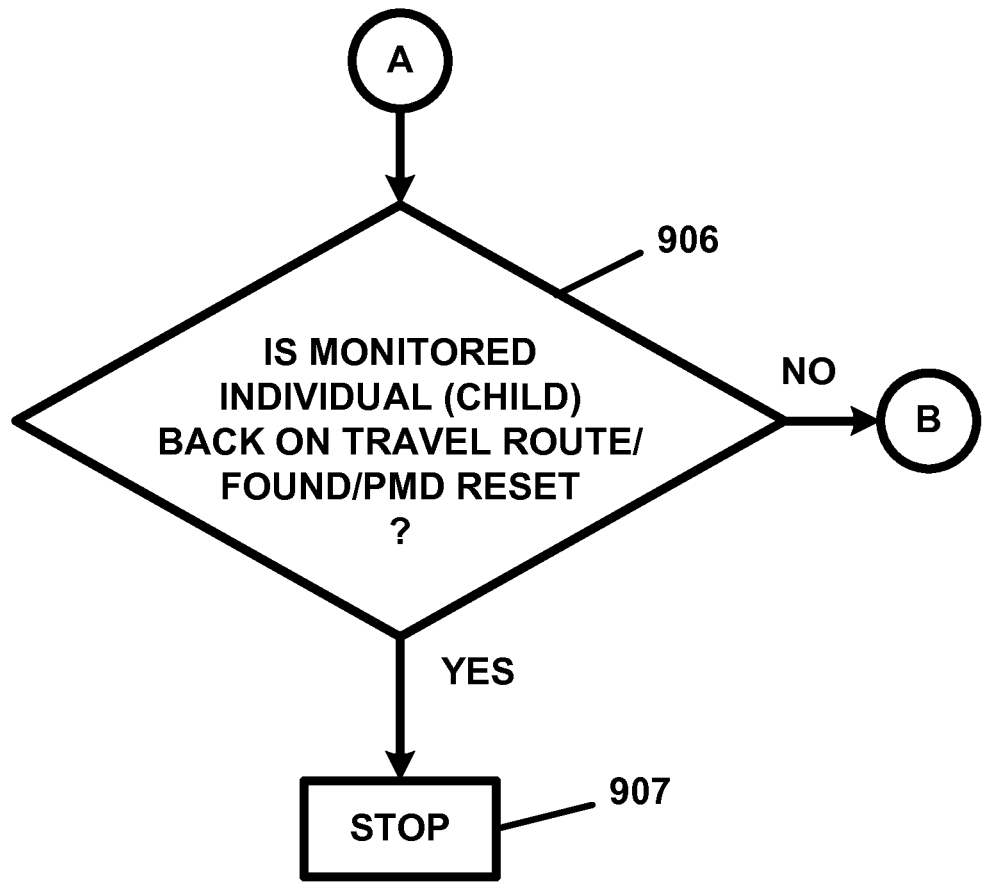

FIGS. 9A and 9B illustrate a preferred embodiment method for utilizing the apparatus 100 and method of the present invention to monitor a monitored individual, in flow diagram form. While the preferred embodiment of FIGS. 9A and 9B is described and illustrated as being used to monitor a child, it is important to note that the preferred embodiment of FIGS. 9A and 9B can be utilized in a same, a similar, and/or an analogous, manner in order to monitor any person or individual of any age and/or any person and/or individual in any kind of physical, mental, or emotional, condition. While the preferred embodiment of FIGS. 9A and 9B is described and illustrated as being used to monitor a child in or during his or her whereabouts and/or travels one place to another, it is also important to note the present invention can also be utilized in a same, a similar, and/or an analogous, manner in order to monitor the child in or during his or her whereabouts and/or travels one place to another, during any given period of time and/or during the course of a day, and/or to monitor any person or individual, of any age, in or during his or her whereabouts and/or travels one place to another, during any given period of time and/or during the course of a day.

With reference to FIGS. 9A and 9B, the operation of the apparatus 100 commences at step 900. At step 901, the personal monitoring device 10 can be activated to operate so as to determine, ascertain, and/or monitor, the child's location or whereabouts. Depending upon the time of the particular day and the schedule of the child, the personal monitoring device 10 can determine the child's position or location and can determine such to be at an address, place, or location, where the child should be at that particular time. For example, at 9:30 AM on a Monday morning during a school year, it is expected that the child can be at his or her school. In a preferred embodiment, the child's travel itinerary or information regarding same can be stored in the database 10H of the personal monitoring device 10 and can include information indicating that the child should leave school at approximately 3:00 PM and travel back to his or her home, either by be driven in a vehicle or a school bus, or by riding a bicycle, or by walking, or by travel by any other mode of travel.

At step 902, the personal monitoring device 10 can detect the child's movement from his or her school, such as by monitoring and/or comparing a change in the child's position or location as determined by utilizing the GPS system of the personal monitoring device 10. At step 902, upon detecting the child's movement and the time of same, the personal monitoring device 10, if determining the time to be approximately 3:00 PM, can identify the child's preferred travel route back home. In a preferred embodiment, the child's preferred travel route from his or her school back to his or her home can be pre-selected and can be pre-programmed by his or her parent, or guardian, or any other caregiver, or other authorized person (a herein-defined "monitoring individual") and can be stored in the personal monitoring device 10. At step 902, the personal monitoring device 10 will determine or ascertain the preferred travel route the child should be taking back home and will monitor the child's travel along that preferred travel route. From this point on, the preferred travel route can simply be referred to as the "travel route".

At step 903, the personal monitoring device 10 can await a detection that the child has deviated from the travel route, or has gone off course from the travel route. Upon detecting that the child has deviated from the travel route, or has gone off course from the travel route, the operation of the personal monitoring device 10 will proceed to step 904. At step 904, the personal monitoring device 10, in a preferred embodiment, can perform any one or more of a number of functions or operations in response to the detection of the child deviating from the travel route.

In a preferred embodiment, at step 904, the personal monitoring device 10, and in particular, the CPU 10A can generate a travel route deviation message. The travel route deviation message can contain and/or include the time and/or place, position, or location, when and/or where the child deviated from or left the travel route and the child's current place, position, or location. The travel route deviation message can also include information regarding the portion of the child's itinerary associated with the travel route from which the child has deviated. For example, as in the example of the preferred embodiment when the child has deviated from his or her travel back home from school, the travel route deviation message can also contain information indicating that the child has deviated from the travel route he or she was taking to go home from school.

At step 905, the personal monitoring device 10 can automatically transmit the travel route deviation message to the user communication device 30 which is used by, associated with, or assigned to, the monitoring individual for the child. In a preferred embodiment, for example, the monitoring individual can be a parent, a grandparent, a sibling, a relative, a friend, a guardian, or any other authorized person. In a situation where the child may be monitored by more than one monitoring individual, then the personal monitoring device 10, at step 905, can transmit the travel route deviation message to the user communication device 30 which is used by, associated with, or assigned to, each and every monitoring individual for the child. In a preferred embodiment, the personal monitoring device 10 can generate and transmit updated travel route deviation messages at any pre-determined or pre-selected time intervals.

At step 905, the personal monitoring device 10 can also automatically transmit the travel route deviation message to the central processing computer 20 so as to report the child's travel route deviation to the central processing computer 20 and to any company or entity which operates same. At step 905, the personal monitoring device 10 can also automatically transmit the travel route deviation message to the law enforcement communication devices 40 of or associated with each law enforcement agency or department associated with the city, town, municipality, or political subdivision, in which the child was detected as having deviated from the travel route, as well as to each law enforcement communication device(s) 40 of or associated with any neighboring cities, towns, municipalities, or political subdivisions. At step 905, the personal monitoring device 10 can also automatically transmit the travel route deviation message to the emergency services provider communication device 50 of or associated with the emergency services provider agency or department of or for the city, town, municipality, or political subdivision, in which the child was detected as having deviated from the travel route, as well as to each emergency services provider communication device 50 of or associated with any neighboring cities, towns, municipalities, or political subdivisions. At step 905, the travel route deviation message can be received by the user communication device 30, and by each central processing computer 20 and/or law enforcement communication device 40 and/or emergency services provider communication device 50 to which it was sent.

At step 905, the personal monitoring device 10 can also obtain, determine, read, or record, any physiological or healthcare information regarding the child such as, for example, but not limited to, the child's heart rate, pulse rate, blood pressure, body temperature, blood sugar level, or any other healthcare information or healthcare-related data and/or information, or any other physical condition, physiological condition, or healthcare condition, which can be measured or measurable by any wearable device or by any implanted device or implantable device which can be obtained by or using any of the respective and herein-described devices, equipment, monitors, or measurement devices, which can be wearable or non-wearable and/or which can be connected to or with, or wirelessly linked to or with the personal monitoring device 10 and/or the CPU 10A of same. Any data and/or information obtained regarding any of the herein-described data and/or information can also be included in the travel route deviation message and/or in any subsequently generated and transmitted travel route deviation messages or updated travel route deviation messages. For example, in addition to the child's current position or location, information regarding the child's heart rate, body temperature, or any other healthcare information can be provided in the travel route deviation message.

In another preferred embodiment, the travel route deviation message can also contain and/or include the temperature of the environment in which the child is located, which can be exterior temperature if the child and the personal monitoring device 10 is located outdoors, or an interior temperature if the child and the personal monitoring device 10 are located indoors.

In a preferred embodiment, the personal monitoring device 10, at step 905, can also initiate a cellular or wireless telephone call to the user communication 30 of the monitoring individual. In another preferred embodiment, if more than one monitoring individuals are associated with the child, then the personal monitoring device 10 can initiate a cellular or wireless telephone call, and/or a telephone conference call, to and/or so as to include the child and all monitoring individuals for the child. In another preferred embodiment, the personal monitoring device 10 can initiate a cellular or wireless telephone call, and/or a telephone conference call, to and/or so as to include at least one monitoring individual and a law enforcement officer or individual, via and/or by including a respective law enforcement communication device 40, and/or an emergency services provider individual or person via and/or by including an emergency services provider communication device 50.

In a preferred embodiment, the cellular or wireless telephone call can be made so as to put the child into live contact with, and/or into live communication with, the monitoring individual or monitoring individuals, and/or so as to put the child and the monitoring individual or monitoring individuals into live contact with, and/or into live communication with, law enforcement personnel and/or emergency services personnel.

In a preferred embodiment, at step 905, once the cellular or wireless telephone call and/or any conference line involving the monitoring individual or monitoring individuals, and/or any law enforcement law enforcement personnel and/or emergency services personnel, has been made and, with the call line and/or conference line being live and/or on-going, the personal monitoring device 10 can de-activate the personal monitoring device's 10 telephone call on/off switch, or on/off switch functionality, on or in the personal monitoring device 10 so that the personal monitoring device 10 cannot be disconnected from the telephone call and/or the conference line. In a preferred embodiment, the herein-described de-activation of the telephone call on/off switch, or on/off switch functionality, of the personal monitoring device 10 can be effectuated by using, and/or by programming the personal monitoring device 10, with or using any appropriate and/or suitable software program, algorithm, or software application. In a preferred embodiment, the personal monitoring device 10 can also be programmed and/or equipped so as to detect being disconnected from, or dropped from, the telephone call and/or conference call, and can automatically re-connect to the telephone call and/or to the conference call. It is to be understood, that any of the herein-described personal monitoring device(s) 10, user communication device(s) 30, law enforcement communication device(s) 40, and/or an emergency services provider communication device(s) 50, can be equipped with long lasting batteries or power sources, external batteries or power sources, and/or any other supplemental batteries or power sources so as to ensure that sufficient electrical power is available and can be supplied to any of the herein-described personal monitoring device(s) 10, user communication device(s) 30, law enforcement communication device(s) 40, and/or an emergency services provider communication device(s) 50.

In a preferred embodiment, the herein-described functionality of establishing a cellular or wireless telephone call, and/or conference call, can allow the child to be brought into, and to be maintained in, live contact with and/or live communication with, his or her monitoring individual or one or more monitoring individuals, and/or with any number of law enforcement personal and/or emergency services personnel. In this manner, the monitoring individual or monitoring individuals, and/or any law enforcement personnel and/or emergency services personnel, can speak with the child, can comfort or reassure the child that all will be okay, and/or can ascertain the child's whereabouts, while the child my be lost or off track. In a preferred embodiment, the personal monitoring device 10 can activate the speakerphone, and/or any speakers and/or microphone, of same for and/or during the cellular or wireless telephone call and/or conference call.

In a preferred embodiment, any activation or use of a speakerphone functionality of the personal monitoring device 10 can also be utilized in order to establish or facilitate an intercom, or an intercommunication or intercom-like, communication platform or system which can provide for open communication involving or between the child, any individual or person coming into contact with the child, and the monitoring individual, and/or any law enforcement personnel, emergency services personnel, or any operator of the central processing computer 20.

In a preferred embodiment, the personal monitoring device 10 can also, at step 905, activate any camera, any video recording device or equipment, any microphone, or any audio recording device, of same, and/or any device or equipment of the video and/or audio recording device(s) 10J of same, for and/or during the cellular or wireless telephone call and/or conference call.

In another preferred embodiment, the personal monitoring device 10 can, at step 905, activate one or more indicator lights 18 or 19 on the personal monitoring device 10 which can be used to indicate that the child is currently outside of his or her "safe" zone of travel. As noted herein, the personal monitoring device 10 can be provided with one or more indicator lights 18 or 19 which can be used to indicate when the child is inside or within his or her "safe" zone of travel and one or more indicator lights 18 or 19 which can be used to indicate when the child is not in, or outside, of his or her "safe" zone of travel. In a preferred embodiment, when the child is inside or within his or her "safe" zone of travel, one or more of these indicator lights 18 or 19 can be lit or illuminated with a green light. In a preferred embodiment, when the child is outside of his or her "safe" zone of travel, one or more of these indicator lights 18 or 19 can be lit or illuminated with a red light. In a preferred embodiment, the personal monitoring device 10 and/or the CPU 10A can, at step 905, activate or cause one or more of the indicator lights 18 or 19 to be lit or illuminated in red. In this regard, any individual or person who may see, or come into contact with the child can be notified, by seeing the red lights on the personal monitoring device 10, that the child may be lost or otherwise in need of assistance. In a preferred embodiment, any indicator lights can also be provided via the display screen or in or via a portion or section of the display screen.

In a preferred embodiment, the personal monitoring device 10 can also, at step 905, activate any camera, any video recording device or equipment, any microphone, or any audio recording device, of same, and/or any device or equipment of the video and/or audio recording device(s) 10J of same, for obtaining pictures, video information, video clips, audio information, or audio clips, of the child, or any individual's or person who or may come into contact with the child, and/or of any of the child's surroundings, environment, or location. In a preferred embodiment, any pictures, video information, video clips, audio information, or audio clips, recorded by and at the personal monitoring device 10 can be transmitted to, and stored by or in, each of the user communication device 30 of the monitoring individual, each user communication device 30 of each monitoring individual, the central processing computer 20, or any law enforcement communication device(s) 40, and/or an emergency services provider communication device(s) 50. In this regard, any audio or video which can be used to ascertain the child's location or which can be used to ascertain any individuals or persons with the child or who the child may have come into contact with, can be recorded by the personal monitoring device 10 and transmitted to, and/or viewed and/or listened to, and/or stored, via or at each of the user communication device 30 of the monitoring individual, each user communication device 30 of each monitoring individual, the central processing computer 20, or any law enforcement communication device(s) 40, and/or an emergency services provider communication device(s) 50.

In another preferred embodiment, the personal monitoring device 10 can also, at step 905, begin to, or can continue to, track the child's movements and can generate tracking update messages at any pre-selected time interval(s), containing information regarding the child's location(s), movement(s), and speed of travel or movement. In a preferred embodiment, the personal monitoring device 10, as well as the central processing computer(s) 20, the user communication(s) 30, the law enforcement communication device(s) 40, and/or the emergency services provider communication device(s) 50, can be equipped with software to calculate or otherwise determine the child's speed of movement. In this manner, depending on the speed of movement of the child, it can be determined if the child is traveling in or on a vehicle or is traveling on foot. In a preferred embodiment, the tracking update messages can be automatically transmitted, at periodic time intervals, from the personal monitoring device 10 to the user communication(s) 30 of the monitoring individual(s), and/or, or as well as, to the central processing computer(s) 20, the user communication(s) 30, the law enforcement communication device(s) 40, and/or the emergency services provider communication device(s) 50.

In a preferred embodiment, information regarding the child's movement can be displayed and/or tracked on or via a digital or satellite map which can be displayed on the display device of the respective user communication(s) 30, the central processing computer(s) 20, the law enforcement communication device(s) 40, and/or the emergency services provider communication device(s) 50. In a preferred embodiment, the information regarding the child's movement can also be displayed and/or tracked on or via a digital or satellite map which can be displayed on the display screen 12 of the personal monitoring device 10.

In a preferred embodiment, the personal monitoring device 10 can also, at step 905, activate a homing beacon or beacon of the personal monitoring device 10. In a preferred embodiment, the homing beacon or beacon of the personal monitoring device 10 can transmit or provide a signal, a distress signal, or any other indication, which can be utilized in connection with a corresponding receiver, which can be provided in or with each of the user communication device(s) 30, the central processing computer(s) 20, the law enforcement communication device(s) 40, and/or the emergency services provider communication device(s) 50, and which can allow for any user or operator of such device(s) or computers 30, 20, 40, and/or 50, to track and/or to "home" in on or locate the child. In a preferred embodiment, the equipment and technology which can be used to implement the beacon or homing beacon and any associated receivers can be the same as, similar to, or analogous to, the technology which was used in vehicle tracking devices such as Lo-Jack® systems and/or any other vehicle recovery systems or any other suitable vehicle tracking and locating systems which are known by those skilled in the art of vehicle recovery systems. Any of the herein-described users or operators of any of the herein-described device(s) or computers 30, 20, 40, and/or 50, can thereafter use his/her/its respective device(s) or computer 30, 20, 40, and/or 50, in order to "home" in on the signals transmitted from or emitted from the beacon or homing beacon.

In a preferred embodiment, at step 905, the personal monitoring device 10 can also play any pre-recorded messages or video clips or audio clips, which messages, video clips, or audio clips, to the child via the display screen 12 and speakers 16. In a preferred embodiment, the pre-recorded messages or video clips or audio clips can be pre-recorded by the monitoring individual or by any number of monitoring individuals, and can be stored in the personal monitoring device 10. The pre-recorded messages or video clips or audio clips can be used in order to comfort the child or calm the child down, if needed, by providing him or her with the voice and/or image of the monitoring individual or monitoring individuals. The pre-recorded messages or video clips or audio clips can also contain or include contact information for the child or his or her monitoring individual, name and address of the child, contact telephone numbers, contact e-mail addresses, contact text message, MMS message, or SMS message, numbers, IP addresses, ad/or any other information, and/or can contain any instructions and/or information needed for caring for the child, including any medications or drugs which the child requires and/or any other healthcare needs or any special needs of the child. In this regard, the pre-recorded messages or video clips or audio clips can also contain or include any information which any individual or person may need or find helpful in assisting the child until the child is found or recovered.

In a preferred embodiment, the personal monitoring device 10 can also, at step 905, provide information, and/or a link to information, regarding or contained in the healthcare records of the child. In a preferred embodiment, any information contained in the child's healthcare records can be stored in the personal monitoring device 10. In another preferred embodiment, a link or a hyperlink to the child's healthcare records can be provided via the personal monitoring device 10 so as to allow any individual or person to gain access to the child's healthcare records, which healthcare records can be stored in or at the central processing computer 20, the user communication device 30 of a monitoring individual, or the healthcare records computer 60. In a preferred embodiment, the personal monitoring device 10 can provide information, and/or a link to information, regarding any healthcare needs of the child or any special needs of the child.

In a preferred embodiment, the personal monitoring device 10 can also, at step 905, provide information regarding any instructions or directions for guiding the child back onto his or her travel route. In another preferred embodiment, the personal monitoring device 10 can, at step 905, activate or turn on a flashlight or a flashlight functionality, and/or a strobe light or a strobe light functionality.

In a preferred embodiment, at any time during step 905 and/or at any other time, the user communication device 30 can generate and/or can transmit a control signal to the personal monitoring device 10 in order to enable, disable, activate, de-activate, control an operation of, or monitor an operation of, the personal monitoring device 10 and/or any component, system, device, or equipment, of same. In this regard, the user communication device 30 can generate and/or can transmit a control signal to the personal monitoring device 10 in order to enable, disable, activate, de-activate, control an operation of, or monitor an operation of, the personal monitoring device 10 and/or any component, system, device, or equipment, of same, including, but not limited to, the CPU 10A, the input device(s) 10D, the display device(s) 10E, the transmitter(s) 10F, the receiver(s) 10G, the output device(s) 10I, the video and/or audio recording device(s) 10J, the GPS device 10K, any of the device functional systems 10L, the display screen 12, the display section 13, the keyboard section 14, the microphone(s) 15, the speaker(s) 16, the camera(s) 17, or the indicator light(s) 18 or 19.

In a preferred embodiment, the user communication device 30 can also, at step 905 and/or at any other time, transmit the control signal over any appropriate communication network(s) to the personal monitoring device 10. In another preferred embodiment, the user communication device 30 can transmit the control signal over the appropriate communication network(s) to the personal monitoring device 10 via the central processing computer 20.

In another preferred embodiment, the central processing computer 20 can also, at step 905 and/or at any other time, can generate and/or can transmit a control signal to the personal monitoring device 10 in order to enable, disable, activate, de-activate, control an operation of, or monitor an operation of, the personal monitoring device 10 and/or any component, system, device, or equipment, of same. In this regard, the user communication device 30 can generate and/or can transmit a control signal to the personal monitoring device 10 in order to enable, disable, activate, de-activate, control an operation of, or monitor an operation of, the personal monitoring device 10 and/or any component, system, device, or equipment, of same, including, but not limited to, the CPU 10A, the input device(s) 10D, the display device(s) 10E, the transmitter(s) 10F, the receiver(s) 10G, the output device(s) 10I, the video and/or audio recording device(s) 10J, the GPS device 10K, any of the device functional systems 10L, the display screen 12, the display section 13, the keyboard section 14, the microphone(s) 15, the speaker(s) 16, the camera(s) 17, or the indicator light(s) 18 or 19.

In another preferred embodiment, any authorized law enforcement communication device 40 and/or any authorized emergency services provider communication device 50 can also, at step 905 and/or at any other time, can generate and/or can transmit a control signal to the personal monitoring device 10 in order to enable, disable, activate, de-activate, control an operation of, or monitor an operation of, the personal monitoring device 10 and/or any component, system, device, or equipment, of same. In this regard, any authorized law enforcement communication device 40 and/or any authorized emergency services provider communication device 50 can generate and/or can transmit a control signal to the personal monitoring device 10 in order to enable, disable, activate, de-activate, control an operation of, or monitor an operation of, the personal monitoring device 10 and/or any component, system, device, or equipment, of same, including, but not limited to, the CPU 10A, the input device(s) 10D, the display device(s) 10E, the transmitter(s) 10F, the receiver(s) 10G, the output device(s) 10I, the video and/or audio recording device(s) 10J, the GPS device 10K, any of the device functional systems 10L, the display screen 12, the display section 13, the keyboard section 14, the microphone(s) 15, the speaker(s) 16, the camera(s) 17, or the indicator light(s) 18 or 19.

In a preferred embodiment, the law enforcement communication device 40 and/or the emergency services provider communication device 50 can also, at step 905 and/or at any other time, transmit the control signal over any appropriate communication network(s) to the personal monitoring device 10. In another preferred embodiment, the law enforcement communication device 40 and/or the emergency services provider communication device 50 can transmit the control signal over the appropriate communication network(s) to the personal monitoring device 10 via the central processing computer 20.

In a preferred embodiment, at step 905, the personal monitoring device 10 and/or the CPU 10A can continue determining and tracking the child's position or location by using the GPS device 10K. In a preferred embodiment, the personal monitoring device 10 and/or the CPU 10A, at any pre-defined or pre-selected time interval, which in a preferred embodiment can be one (1) minute or any other suitable time interval, and while any and/or all functionality described herein as being performed at step 905, can determine if the child made it back onto his or her travel route and/or can determine if the child has been found. In this regard, the operation of the personal monitoring device 10 can proceed to step 906 and the personal monitoring device 10 and/or the CPU 10A can determine if the child is back on his or her travel route or can determine if the child has been found and that an instruction to reset the personal monitoring device 10 has been received by the personal monitoring device 10 or has been input into the personal monitoring device 10.

If, at step 906, it is determined that the child is back on his or her travel route, or that the child has been found, or that an instruction to reset the personal monitoring device 10 has been received by the personal monitoring device 10 or has been input into the personal monitoring device 10, then the operation of the apparatus 100 will cease at step 907. Thereafter, the personal monitoring device 10 can be reset for future use. If at step 906, it is determined that the child has still not made it back to his or her travel route, or that the child has still not been found, or that no instruction to reset the personal monitoring device 10 has been received by the personal monitoring device 10 or has been input into the personal monitoring device 10, then the operation of the apparatus 100 will return to, or continue on as described during, step 905 as described herein. The apparatus 100 will thereafter continue to function and/or operate at steps 905 and 906 until it is determined by the personal monitoring device 10 and/or the CPU 10A that the child is found to be back on his or her travel route, or the child has been found, or until an instruction to reset the personal monitoring device 10 has been received by the personal monitoring device 10 or has been input into the personal monitoring device 10.

Although described herein as being utilized to monitor a child, it is important to note that the apparatus 100 and the personal monitoring device 10 of FIGS. 9A and 9B can be utilized in a same, a similar, and/or an analogous, manner to monitor individuals of any age, including but not limited to infants, children, adolescents, teenagers, adults of any age, elderly individuals, individuals having no healthcare issues, conditions, problems, or challenges, and/or individuals having healthcare issues, conditions, problems, or challenges. The apparatus 100 and method of the present invention as well as the apparatus of FIGS. 9A and 9B can be used to monitor children who may be afflicted with autism, or any disabilities, or who may lack communications skills, and/or who may have other conditions, as well as individuals of any age who are afflicted with Alzheimer's disease or Dementia, o any other healthcare conditions. The apparatus 100 and method of the present invention as well as the apparatus of FIGS. 9A and 9B can be used to monitor individuals of any age who may have no healthcare conditions or problems, but who might want to simply utilize the apparatus 100 and method of the present inventions for the numerous benefits it can provide.

In a preferred embodiment, any of the functions and/or functionality described herein as being performed by the personal monitoring device 10 at or during step 905 can be pre-programmed into the personal monitoring device 10 beforehand by any authorized individual and/or by a monitoring individual. In a preferred embodiment, any of the functions and/or functionality described herein as being performed by the personal monitoring device 10 at or during step 905 can be changed or can be re-programmed at any time. In another preferred embodiment, any functions and/or functionality described herein as being performed by the personal monitoring device 10 at or during step 905 can also be enabled, disabled, activated, deactivated, or controlled, or monitored, by or via the user communication device 30, the central processing computer 20, the law enforcement communication device 40, or the emergency services provider communication device 50.

In a preferred embodiment, as well as in any and/or all of the embodiments described herein, a personal monitoring account can be created or established for any monitored individual with whom the apparatus 100 and method of the present invention can be utilized. In this regard, a personal monitoring account can be established for a monitored individual and can be registered with the central processing computer 20, and/or with any law enforcement departments and/or agencies and/or with an emergency services providers departments and/or agencies so that the central processing computer 20 and the respective law enforcement communication devices 40 and/or emergency services providers communication devices 50 can has records and information for or regarding any monitored individuals and the respective individual who are to be monitoring them (the so-call "monitoring individuals"). Any of the data and/or information described herein as being stored in any of the databases 10H, 20H, 30H, 40H, 50H, and/or 60H, of any of the herein-described personal monitoring devices 10, central processing computers 20, user communication devices 30, law enforcement communication devices 40, emergency services providers communication devices 50, and/or healthcare records computers 60, can be stored in a respective monitored individuals personal monitoring account.

In another preferred embodiment, the operation of the apparatus 100 and/or the personal monitoring device 10 can be triggered by, or can be activated by or in response to the actions of, a monitoring individual. In a preferred embodiment, a monitoring individual can utilize a software application or a software "app" in order to determine the position or location of the monitored individual. The software application or software "app", in a preferred embodiment, should be capable of determining the position or location of the monitored individual at any time and/or on demand by the monitoring individual. In another preferred embodiment, the monitoring individual can also perform a "pinging" operation in order to utilize a communications services provider or any other suitably equipped entity in order to "ping" or determine the position or location of the monitored individual.

In a preferred embodiment, at any time, a monitoring individual can either utilize a software application or a software "app" on his or her user communication device 30, or can "ping" the personal monitoring device 10 of or associated by the monitored individual, in order to determine the position or location of the monitored individual and/or to determine if the monitored individual is at an expected place or location, is traveling on an appropriate travel route at that point or instant in time, or is at an unexpected or unapproved place or location, or has deviated from an appropriate travel route at that point or instant in time. If the monitored individual is determined to be at an unexpected or unapproved place or location, or has deviated from an appropriate travel route at that point or instant in time, the monitoring individual can activate the apparatus 100 and utilize same to find or locate, or otherwise provide assistance to, the monitored individual.

As described herein, any user or individual who utilizes a personal monitoring device 10, or who has a personal monitoring device 10 assigned to him or her, or who has a personal monitoring device 10 associated with him or her, can again be referred to herein, or can be defined herein as being, a "monitored individual". As also described herein, any user or individual who utilizes a user communication device 30 to monitor a monitored individual can be referred to herein, or can be defined herein as being, a "monitoring individual".

As described herein, it is envisioned that a personal monitoring device 10 can be programmed with, or have stored therein or therewith, information regarding the monitored individual's home address, residence address, school residence address or place, workplace address, or other address, place, or location, which is considered to be that monitored individual's place of safety or "home base" or "safe location". In a preferred embodiment, it is envisioned that the personal monitoring device 10 can be programmed with, or have stored therein or therewith, information regarding any address(es), place(s), or location(s), to which the monitored individual typically travels on a daily basis. For example, the personal monitoring device 10 can be programmed with, or have stored therein or therewith, information regarding the monitored individual's school address, place, or location, workplace address, place, or location, employment address, place, or location, activity or event address, place, or location, or any other address, place, or location, to which the monitored individual is known to travel on a weekday basis, on a weekend daily basis, or on any daily basis.

As also described herein, the personal monitoring device 10 can also be programmed with the monitored individual's travel itineraries and/or travel schedules for traveling to and between one address, place, or location to another address, place, or location. In this regard, the personal monitoring device 10 can also be programmed with travel routes or directions for traveling to and between one address, place, or location to another address, place, or location. As also noted herein, in a preferred embodiment, the personal monitoring device 10 can also be programmed with software programs, navigation programs, or any algorithms or software applications, for identifying, determining, ascertaining, or calculating, any travel routes or directions for traveling to and between one address, place, or location to another address, place, or location.

In any and/or all of the embodiments described herein, the personal monitoring device 10 can be utilized in connection with, or in conjunction with, the apparatus 100, the central processing computer 20, a user communication device 30 associated with, or used by, any user or individual authorized to, or assigned to, monitor the monitored individual, any law enforcement communication device 40, and/or any emergency services provider communication device 50. As also described herein, the personal monitoring device 10 can also be utilized as a stand-alone device by the monitored individual to allow the monitored individual to monitor his or her travels, whereabouts, or environment.

Figure 10A:
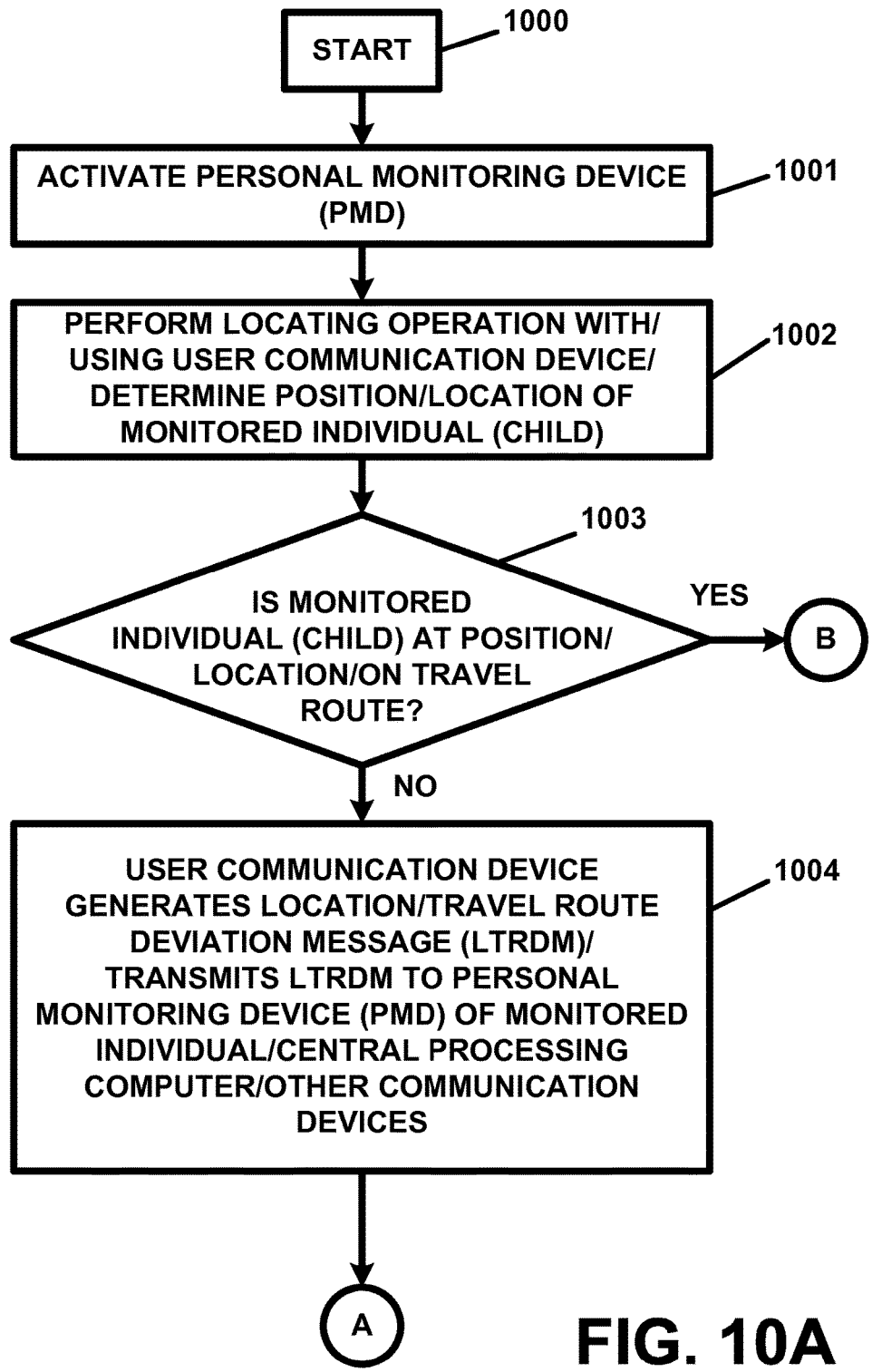
FIGS. 10A and 10B illustrate another preferred embodiment method for utilizing the apparatus of the present invention, in flow diagram form.
Figure 10B:
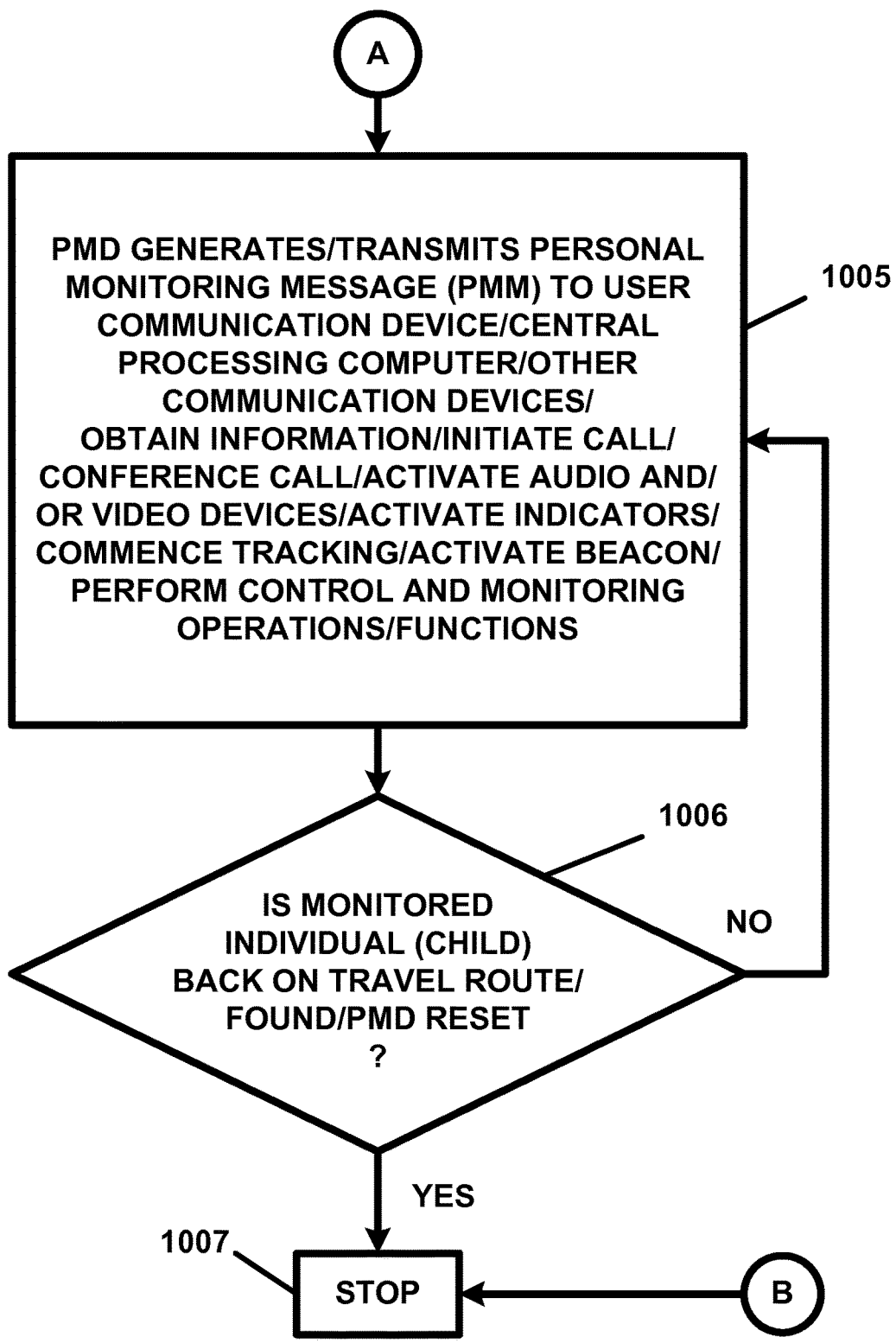

FIGS. 10A and 10B illustrate another preferred embodiment method for utilizing the apparatus 100 and method of the present invention to monitor a monitored individual, in flow diagram form. While the preferred embodiment of FIGS. 10A and 10B is described and illustrated as being used to monitor a child, it is important to note that the preferred embodiment of FIGS. 10A and 10B can also be utilized in a same, a similar, and/or an analogous, manner in order to monitor any person or individual of any age and/or any person and/or individual in any kind of physical, mental, or emotional, condition. While the preferred embodiment of FIGS. 10A and 10B is described and illustrated as being used to monitor a child in or during his or her whereabouts and/or travels one place to another, it is also important to note the present invention can also be utilized in a same, a similar, and/or an analogous, manner in order to monitor the child in or during his or her whereabouts and/or travels one place to another, during any given period of time and/or during the course of a day, and/or to monitor any person or individual, of any age, in or during his or her whereabouts and/or travels one place to another, during any given period of time and/or during the course of a day.

With reference to FIGS. 10A and 10B, the operation of the apparatus 100 commences at step 1000. At step 1001, the personal monitoring device 10 can be activated to operate so as to determine, ascertain, and/or monitor, the child's location or whereabouts. Depending upon the time of the particular day and the schedule of the child, the personal monitoring device 10 can determine the child's position or location and can determine such to be at an address, place, or location, where the child should be at that particular time. For example, and as described herein, at 9:30 AM on a Monday morning during a school year, it is expected that the child can be at his or her school. In a preferred embodiment, the child's travel itinerary or information regarding same can be stored in the database 10H of the personal monitoring device 10 and can include information indicating that the child should leave school at approximately 3:00 PM and travel back to his or her home, either by be driven in a vehicle or a school bus, or by riding a bicycle, or by walking, or by travel by any other mode of travel.

At any time of day, the monitoring individual can utilize his or her user communication device 30 in order to determine the child's position or location so as to verify that the child is where he or she should be or that the child, if traveling from one place to another, is on the travel route to his or her destination. At step 1002, the monitoring individual can perform a locating operation using his or her user communication device 30 in order to determine or ascertain the position or the location of the child. In a preferred embodiment, the monitoring individual can utilize any suitable software program or software application which can be loaded onto or stored on or in, his or her user communication device 30 in order to determine the child's position or location. In a preferred embodiment, any suitable software program or software application, which is available in the marketplace, or which is available commercially, as of the time of the filing of this application, and which can be utilized in order to allow any individual or person, to determine, or locate, a position or location of another individual or person can be utilized in and by the user communication device 30 and the monitoring individual in order to allow the monitoring individual to determine the position or location of the child.

In another preferred embodiment, instead of using a software program of a software application to determine the position or location of the child, the monitoring individual can also request that the central processing computer 20 or the cellular or wireless communication service provider which services the apparatus 100, the user communication device 30, or the personal monitoring device 10, perform a "pinging" operation for the personal monitoring device 10 in order to determine its position or location.

In another preferred embodiment, the monitoring individual can access utilize his or her user communication device 30 in order to access the personal monitoring device 10, either via any communication network(s) and/or via the central processing computer 20 and/or any communication network(s) and request the position or location of the child as determined by the GPS device 10K of the personal monitoring device 10. In this regard, the monitoring individual can utilize his or her user communication device 30 in order to perform a control and/or monitoring operation on the personal monitoring device 10 in order to determine or ascertain the position or location of same as, therefore, the position or location of the child.

At step 1002, the information regarding the position or location of the child can be determined and provided to the user communication 30. The monitoring individual can then be provided with the information regarding the position or location of the child on or via his or her user communication device 30. In a preferred embodiment, the child's position or location can be provided on a display screen or a display device 30E of the user communication device 30 and can be shown on, or can be pin-pointed on, a map. In a preferred embodiment, the map can be a digitized map, a satellite map, or any other appropriate map display can contain an indication of the child's position or location thereon.

At step 1003, the monitoring individual can determine whether or not the child is located at a place or location where he or she should be at that particular time, or the monitoring individual can determine whether or not the child is on a travel route that he or she should be on at that particular time. In another preferred embodiment, the user communication device 30 can, by using the information regarding the position or location of the child, automatically determine whether or not the child is located at a place or location where he or she should be at that particular time, or the user communication device 30 can automatically determine whether or not the child is on a travel route that he or she should be on at that particular time.

If, at step 1003, it is determined that the child is at a place or location where he or she should be at that particular time, or that the child is on a travel route that he or she should be on at that particular time, then the operation of the apparatus 100 will cease at step 1007. If, however, at step 1003, it is determined that the child is not at a place or location where he or she should be at that particular time, or that the child is not on a travel route that he or she should be on at that particular time, then the operation of the apparatus 100 will proceed to step 1004.

At step 1004, the monitoring individual can utilize the user communication device 30 in order generate a location/travel route deviation message regarding the child. The location/travel route deviation message can contain the determined position or location of the child and the time of such determination, and/or the location/travel route deviation message, in the case of the child's deviation from a travel route, can contain the time and/or place, and the position or location, when and/or where the child deviated from or left the travel route and the child's current place, position, or location. The location/travel route deviation message can also include information regarding the portion of the child's itinerary associated with place or location of the child or associated with the travel route from which the child has deviated.

In another preferred embodiment, the user communication device 30 can automatically generate a location/travel route deviation message regarding the child which location/travel route deviation message can contain the determined position or location of the child and the time of such determination, and/or the location/travel route deviation message, in the case of the child's deviation from a travel route, can contain the time and/or place, and the position or location, when and/or where the child deviated from or left the travel route and the child's current place, position, or location. The location/travel route deviation message automatically generated by the user communication device 30 can also include information regarding the portion of the child's itinerary associated with place or location of the child or associated with the travel route from which the child has deviated.

In a preferred embodiment, the location/travel route deviation message can also contain data and/or information for programming, and/or for activating, deactivating, enabling, disabling, controlling an operation of or any number of operations of, or monitoring an operation of or any number of operations of, the personal monitoring device 10 and/or any component, system, device, or equipment, of same, including, but not limited to, the CPU 10A, the input device(s) 10D, the display device(s) 10E, the transmitter(s) 10F, the receiver(s) 10G, the output device(s) 10I, the video and/or audio recording device(s) 10J, the GPS device 10K, any of the device functional systems 10L, the display screen 12, the display section 13, the keyboard section 14, the microphone(s) 15, the speaker(s) 16, the camera(s) 17, or the indicator light(s) 18 or 19.

At step 1004, the user communication device 30 can transmit the location/travel route deviation message to the personal monitoring device 10. In a preferred embodiment, at step 1004, the user communication device 30 can also transmit the location/travel route deviation message to the personal monitoring device 10 via the central processing computer 20. In a preferred embodiment, the user communication device 30 can also, at step 1004, transmit the location/travel route deviation message to the central processing computer 20. In a preferred embodiment, the user communication device 30 can also, at step 1004, transmit the location/travel route deviation message to the law enforcement communication device(s) 40 of or associated with the city, town, municipality, or political subdivision, in which the child has been determined to be positioned or located, as well to the law enforcement communication device(s) 40 of or associated with the any neighboring cities, towns, municipalities, or political subdivisions. In a preferred embodiment, the user communication device 30 can also, at step 1004, transmit the location/travel route deviation message to the emergency services provider communication device 50 of or associated with the city, town, municipality, or political subdivision, in which the child has been determined to be positioned or located, as well to the emergency services provider communication device(s) 50 of or associated with any neighboring cities, towns, municipalities, or political subdivisions.

At step 1004, the personal monitoring device 10, and/or, if applicable, the central processing computer 20, the law enforcement communication device(s) 40, and/or the emergency services provider communication device(s) 50, can receive, process, and/or store, any data and/or information in, the location/travel route deviation message. Thereafter, the operation of the apparatus 100 will proceed to step 1005.

At step 1005, the personal monitoring device 10 can automatically perform any one or more of any of the functions or functionalities described herein as being performed by the personal monitoring device 10 at or during step 905 of the embodiment of FIGS. 9A and 9B.

In a preferred embodiment, at step 1005, the personal monitoring device 10 can generate a personal monitoring message, which can contain the time, date, and the current position or location of the child, and the personal monitoring device 10 can transmit the personal monitoring message to the user communication device 30. In a preferred embodiment, the personal monitoring device 10 can also transmit the personal monitoring message to the central processing computer 20. In a preferred embodiment, the personal monitoring device 10 can also transmit the personal monitoring message to the law enforcement communication device(s) 30 of or associated with the city, town, municipality, or political subdivision, in which the child is determined to be positioned or located, as well message to the law enforcement communication device(s) 30 of or associated with any neighboring cities, towns, municipalities, or political subdivisions. In a preferred embodiment, the personal monitoring device 10 can also transmit the personal monitoring message to the emergency services provider communication device(s) 50 of or associated with the city, town, municipality, or political subdivision, in which the child is determined to be positioned or located, as well to the emergency services provider communication device(s) 50 of or associated with any neighboring cities, towns, municipalities, or political subdivisions.

In a preferred embodiment, the personal monitoring device 10 can obtain, determine, read, or record, any physiological or healthcare information regarding the child such as, for example, but not limited to, the child's heart rate, pulse rate, blood pressure, body temperature, blood sugar level, or any other healthcare information or healthcare-related data and/or information, or any other physical condition, physiological condition, or healthcare condition, which can be measured or measurable by any wearable device or by any implanted device or implantable device which can be obtained by or using any of the respective and herein-described devices, equipment, monitors, or measurement devices, which can be wearable or non-wearable and/or which can be connected to or with, or wirelessly linked to or with the personal monitoring device 10 and/or the CPU 10A of same. Any data and/or information obtained regarding any of the herein-described data and/or information can also be included in the personal monitoring message which can be generated by and transmitted from the personal monitoring device 10 as described herein at periodic time intervals. For example, in addition to the child's current position or location, information regarding the child's heart rate, body temperature, or any other healthcare information can be provided in the personal monitoring message.

In a preferred embodiment, the personal monitoring device 10 can generate and transmit updated personal monitoring messages at any pre-determined or pre-selected time intervals.

In another preferred embodiment, the personal monitoring message can also contain and/or include the temperature of the environment in which the child is located, which can be exterior temperature if the child and the personal monitoring device 10 is located outdoors, or an interior temperature if the child and the personal monitoring device 10 are located indoors.

At step 1005, the personal monitoring device 10 can automatically transmit the personal monitoring message, and any updated personal monitoring messages, to the user communication device 30 which is used by, associated with, or assigned to, the monitoring individual for the child. In a preferred embodiment, for example, the monitoring individual can be a parent, a grandparent, a sibling, a relative, a friend, a guardian, or any other authorized person. In a situation where the child may be monitored by more than one monitoring individual, then the personal monitoring device 10, at step 1005, can transmit the personal monitoring message, as well as any updated personal monitoring messages, to the user communication device 30 which is used by, associated with, or assigned to, each and every monitoring individual for the child.

At step 1005, the personal monitoring device 10 can also automatically transmit any updated personal monitoring message(s) to the central processing computer 20 so as to report the child's potion or location to the central processing computer 20 and to any company or entity which operates same. At step 1005, the personal monitoring device 10 can also automatically transmit any updated personal monitoring message(s) to the law enforcement communication device(s) 40 of or associated with each law enforcement agency or department associated with the city, town, municipality, or political subdivision, in which the child is determined to be positioned or located, as well as to each law enforcement communication device(s) of or associated with each neighboring law enforcement agency or department. At step 1005, the personal monitoring device 10 can also automatically transmit any updated personal monitoring message(s) to the emergency services provider communication device(s) 50 of or associated with each emergency services provider agency or department associated with the city, town, municipality, or political subdivision, in which the child is determined to be positioned or located, as well as to each emergency services provider communication device(s) 50 of or associated with each neighboring emergency services provider agency or department.

In a preferred embodiment, the personal monitoring device 10, at step 1005, can also initiate a cellular or wireless telephone call to the user communication 30 of the monitoring individual. In another preferred embodiment, if more than one monitoring individuals are associated with the child, then the personal monitoring device 10 can initiate cellular or wireless telephone call, and/or a telephone conference call, to and/or so as to include the child and all monitoring individuals for the child. In another preferred embodiment, the personal monitoring device 10 can also initiate a cellular or wireless telephone call, and/or a telephone conference call, to and/or so as to include at least one monitoring individual and a law enforcement officer or individual, via and/or by including a respective law enforcement communication device 40, and/or an emergency services provider individual or person via and/or by including an emergency services provider communication device 50.

In a preferred embodiment, the cellular or wireless telephone call can be made so as to put the child into live contact with, and/or into live communication with, the monitoring individual or monitoring individuals, and/or so as to put the child and the monitoring individual or monitoring individuals into live contact with, and/or into live communication with, law enforcement personnel and/or emergency services personnel.

In a preferred embodiment, at step 1005, once the cellular or wireless telephone call and/or any conference line involving the monitoring individual or monitoring individuals, and/or any law enforcement law enforcement personnel and/or emergency services personnel, has been made and, with the call line and/or conference line being live and/or on-going, the personal monitoring device 10 can de-activate the personal monitoring device's 10 telephone call on/off switch, or on/off switch functionality, on or in the personal monitoring device 10 so that the personal monitoring device 10 cannot be disconnected from the telephone call and/or the conference line. In a preferred embodiment, the herein-described de-activation of the telephone call on/off switch, or on/off switch functionality, of the personal monitoring device 10 can be effectuated by using, and/or by programming the personal monitoring device 10, with or using any appropriate and/or suitable software program, algorithm, or software application. In a preferred embodiment, the personal monitoring device 10 can also be programmed and/or equipped so as to detect being disconnected from, or dropped from, the telephone call and/or conference call, and can automatically re-connect to the telephone call and/or to the conference call. It is to be understood, that any of the herein-described personal monitoring device(s) 10, user communication device(s) 30, law enforcement communication device(s) 40, and/or an emergency services provider communication device(s) 50, can be equipped with long lasting batteries or power sources, external batteries or power sources, and/or any other supplemental batteries or power sources so as to ensure that sufficient electrical power is available and can be supplied to any of the herein-described personal monitoring device(s) 10, user communication device(s) 30, law enforcement communication device(s) 40, and/or an emergency services provider communication device(s) 50.

In a preferred embodiment, the herein-described functionality of establishing a cellular or wireless telephone call, and/or conference call, can allow the child to be brought into, and to be maintained in, live contact with and/or live communication with, his or her monitoring individual or one or more monitoring individuals, and/or with any number of law enforcement personal and/or emergency services personnel. In this manner, the monitoring individual or monitoring individuals, and/or any law enforcement personnel and/or emergency services personnel, can speak with the child, can comfort or reassure the child that all will be okay, and/or can ascertain the child's whereabouts, while the child my be lost or off track. In a preferred embodiment, the personal monitoring device 10 can activate the speakerphone, and/or any speakers and/or microphone, of same for and/or during the cellular or wireless telephone call and/or conference call.

In a preferred embodiment, any activation or use of a speakerphone functionality of the personal monitoring device 10 can also be utilized in order to establish or facilitate an intercom, or an intercommunication or intercom-like, communication platform or system which can provide for open communication involving or between the child, any individual or person coming into contact with the child, and the monitoring individual, and/or any law enforcement personnel, emergency services personnel, or any operator of the central processing computer 20.

In a preferred embodiment, the personal monitoring device 10 can also, at step 1005, activate any camera, any video recording device or equipment, any microphone, or any audio recording device, of same, and/or any device or equipment of the video and/or audio recording device(s) 10J of same, for and/or during the cellular or wireless telephone call and/or conference call.

In another preferred embodiment, the personal monitoring device 10 can also, at step 1005 activate one or more indicator lights 18 or 19 on the personal monitoring device 10 which can be used to indicate that the child is currently outside of his or her "safe" zone of travel. As noted herein, the personal monitoring device 10 can be provided with one or more indicator lights 18 or 19 which can be used to indicate when the child is inside or within his or her "safe" zone of travel and one or more indicator lights 18 or 19 which can be used to indicate when the child is not in, or outside, of his or her "safe" zone of travel. In a preferred embodiment, when the child is inside or within his or her "safe" zone of travel, one or more of these indicator lights 18 or 19 can be lit or illuminated with a green light. In a preferred embodiment, when the child is outside of his or her "safe" zone of travel, one or more of these indicator lights 18 or 19 can be lit or illuminated with a red light. In a preferred embodiment, the personal monitoring device 10 and/or the CPU 10A can, at step 1005, activate or cause one or more of the indicator lights 18 or 19 to be lit or illuminated in red. In this regard, any individual or person who may see, or come into contact with the child can be notified, by seeing the red lights on the personal monitoring device 10, that the child may be lost or otherwise in need of assistance. In a preferred embodiment, any indicator lights can also be provided via the display screen or in or via a portion or section of the display screen.

In a preferred embodiment, the personal monitoring device 10 can also, at step 1005, activate any camera, any video recording device or equipment, any microphone, or any audio recording device, of same, and/or any device or equipment of the video and/or audio recording device(s) 10J of same, for obtaining pictures, video information, video clips, audio information, or audio clips, of the child, or any individual's or person who or may come into contact with the child, and/or of any of the child's surroundings, environment, or location. In a preferred embodiment, any pictures, video information, video clips, audio information, or audio clips, recorded by and at the personal monitoring device 10 can be transmitted to, and stored by or in, each of the user communication device 30 of the monitoring individual, each user communication device 30 of each monitoring individual, the central processing computer 20, or any law enforcement communication device(s) 40, and/or an emergency services provider communication device(s) 50. In this regard, any audio or video which can be used to ascertain the child's location or which can be used to ascertain any individuals or persons with the child or who the child may have come into contact with, can be recorded by the personal monitoring device 10 and transmitted to, and/or viewed and/or listened to, and/or stored, via or at each of the user communication device 30 of the monitoring individual, each user communication device 30 of each monitoring individual, the central processing computer 20, or any law enforcement communication device(s) 40, and/or an emergency services provider communication device(s) 50.

In another preferred embodiment, the personal monitoring device 10 can also, at step 1005, begin to, or can continue to, track the child's movements and can generate tracking update messages or updated personal monitoring messages at any pre-selected time interval(s), containing information regarding the child's location(s), movement(s), and speed of travel or movement. In a preferred embodiment, the personal monitoring device 10, as well as the central processing computer(s) 20, the user communication(s) 30, the law enforcement communication device(s) 40, and/or the emergency services provider communication device(s) 50, can be equipped with software to calculate or otherwise determine the child's speed of movement. In this manner, depending on the speed of movement of the child, it can be determined if the child is traveling in or on a vehicle or is traveling on foot. In a preferred embodiment, the tracking update messages or updated personal monitoring messages can be automatically transmitted, at periodic time intervals, from the personal monitoring device 10 to the user communication(s) 30 of the monitoring individual(s), and/or, or as well as, to the central processing computer(s) 20, the user communication(s) 30, the law enforcement communication device(s) 40, and/or the emergency services provider communication device(s) 50.

In a preferred embodiment, information regarding the child's movement can be displayed and/or tracked on or via a digital or satellite map which can be displayed on the display device of the respective user communication(s) 30, the central processing computer(s) 20, the law enforcement communication device(s) 40, and/or the emergency services provider communication device(s) 50. In a preferred embodiment, the information regarding the child's movement can also be displayed and/or tracked on or via a digital or satellite map which can be displayed on the display screen 12 of the personal monitoring device 10.

In a preferred embodiment, the personal monitoring device 10 can also, at step 1005, activate a homing beacon or beacon of the personal monitoring device 10. In a preferred embodiment, the homing beacon or beacon of the personal monitoring device 10 can transmit or provide a signal, a distress signal, or any other indication, which can be utilized in connection with a corresponding receiver, which can be provided in or with each of the user communication device(s) 30, the central processing computer(s) 20, the law enforcement communication device(s) 40, and/or the emergency services provider communication device(s) 50, and which can allow for any user or operator of such device(s) or computers 30, 20, 40, and/or 50, to track and/or to "home" in on or locate the child. As noted herein, in a preferred embodiment, the equipment and technology which can be used to implement the beacon or homing beacon and any associated receivers can be the same as, similar to, or analogous to, the technology which was used in vehicle tracking devices such as Lo-Jack® systems and/or any other vehicle recovery systems or any other suitable vehicle tracking and locating systems which are known by those skilled in the art of vehicle recovery systems. Any of the herein-described users or operators of any of the herein-described device(s) or computers 30, 20, 40, and/or 50, can thereafter use his/her/its respective device(s) or computer 30, 20, 40, and/or 50, in order to "home" in on the signals transmitted from or emitted from the beacon or homing beacon.

In a preferred embodiment, at step 1005, the personal monitoring device 10 can also play any pre-recorded messages or video clips or audio clips, which messages, video clips, or audio clips, to the child via the display screen 12 and speakers 16. In a preferred embodiment, the pre-recorded messages or video clips or audio clips can be pre-recorded by the monitoring individual or by any number of monitoring individuals, and can be stored in the personal monitoring device 10. The pre-recorded messages or video clips or audio clips can be used in order to comfort the child or calm the child down, if needed, by providing him or her with the voice and/or image of the monitoring individual or monitoring individuals. The pre-recorded messages or video clips or audio clips can also contain or include contact information for the child or his or her monitoring individual, name and address of the child, contact telephone numbers, contact e-mail addresses, contact text message, MMS message, or SMS message, numbers, IP addresses, ad/or any other information, and/or can contain any instructions and/or information needed for caring for the child, including any medications or drugs which the child requires and/or any other healthcare needs or any special needs of the child. In this regard, the pre-recorded messages or video clips or audio clips can also contain or include any information which any individual or person may need or find helpful in assisting the child until the child is found or recovered.

In a preferred embodiment, the personal monitoring device 10 can also, at step 1005, provide information, and/or a link to information, regarding or contained in the healthcare records of the child. In a preferred embodiment, any information contained in the child's healthcare records can be stored in the personal monitoring device 10. In another preferred embodiment, a link or a hyperlink to the child's healthcare records can be provided via the personal monitoring device 10 so as to allow any individual or person to gain access to the child's healthcare records, which healthcare records can be stored in or at the central processing computer 20, the user communication device 30 of a monitoring individual, or the healthcare records computer 60. In a preferred embodiment, the personal monitoring device 10 can provide information, and/or a link to information, regarding any healthcare needs of the child or any special needs of the child.

In a preferred embodiment, the personal monitoring device 10 can also, at step 1005, provide information regarding any instructions or directions for guiding the child back onto his or her travel route. In another preferred embodiment, the personal monitoring device 10 can, at step 1005, activate or turn on a flashlight or a flashlight functionality, and/or a strobe light or a strobe light functionality.

In a preferred embodiment, at any time during step 1005 and/or at any other time, the user communication device 30 can generate and/or can transmit a control signal to the personal monitoring device 10 in order to enable, disable, activate, de-activate, control an operation of, or monitor an operation of, the personal monitoring device 10 and/or any component, system, device, or equipment, of same. In this regard, the user communication device 30 can generate and/or can transmit a control signal to the personal monitoring device 10 in order to enable, disable, activate, de-activate, control an operation of, or monitor an operation of, the personal monitoring device 10 and/or any component, system, device, or equipment, of same, including, but not limited to, the CPU 10A, the input device(s) 10D, the display device(s) 10E, the transmitter(s) 10F, the receiver(s) 10G, the output device(s) 10I, the video and/or audio recording device(s) 10J, the GPS device 10K, any of the device functional systems 10L, the display screen 12, the display section 13, the keyboard section 14, the microphone(s) 15, the speaker(s) 16, the camera(s) 17, or the indicator light(s) 18 or 19.

In a preferred embodiment, the user communication device 30 can also, at step 1005 and/or at any other time, transmit the control signal over any appropriate communication network(s) to the personal monitoring device 10. In another preferred embodiment, the user communication device 30 can transmit the control signal over the appropriate communication network(s) to the personal monitoring device 10 via the central processing computer 20.

In another preferred embodiment, the central processing computer 20 can also, at step 1005 and/or at any other time, can generate and/or can transmit a control signal to the personal monitoring device 10 in order to enable, disable, activate, de-activate, control an operation of, or monitor an operation of, the personal monitoring device 10 and/or any component, system, device, or equipment, of same. In this regard, the user communication device 30 can generate and/or can transmit a control signal to the personal monitoring device 10 in order to enable, disable, activate, de-activate, control an operation of, or monitor an operation of, the personal monitoring device 10 and/or any component, system, device, or equipment, of same, including, but not limited to, the CPU 10A, the input device(s) 10D, the display device(s) 10E, the transmitter(s) 10F, the receiver(s) 10G, the output device(s) 10I, the video and/or audio recording device(s) 10J, the GPS device 10K, any of the device functional systems 10L, the display screen 12, the display section 13, the keyboard section 14, the microphone(s) 15, the speaker(s) 16, the camera(s) 17, or the indicator light(s) 18 or 19.

In another preferred embodiment, any authorized law enforcement communication device 40 and/or any authorized emergency services provider communication device 50 can also, at step 1005 and/or at any other time, generate and/or can transmit a control signal to the personal monitoring device 10 in order to enable, disable, activate, de-activate, control an operation of, or monitor an operation of, the personal monitoring device 10 and/or any component, system, device, or equipment, of same. In this regard, any authorized law enforcement communication device 40 and/or any authorized emergency services provider communication device 50 can generate and/or can transmit a control signal to the personal monitoring device 10 in order to enable, disable, activate, de-activate, control an operation of, or monitor an operation of, the personal monitoring device 10 and/or any component, system, device, or equipment, of same, including, but not limited to, the CPU 10A, the input device(s) 10D, the display device(s) 10E, the transmitter(s) 10F, the receiver(s) 10G, the output device(s) 10I, the video and/or audio recording device(s) 10J, the GPS device 10K, any of the device functional systems 10L, the display screen 12, the display section 13, the keyboard section 14, the microphone(s) 15, the speaker(s) 16, the camera(s) 17, or the indicator light(s) 18 or 19.

In a preferred embodiment, the law enforcement communication device 40 and/or the emergency services provider communication device 50 can also, at step 1005 and/or at any other time, transmit the control signal over any appropriate communication network(s) to the personal monitoring device 10. In another preferred embodiment, the law enforcement communication device 40 and/or the emergency services provider communication device 50 can transmit the control signal over the appropriate communication network(s) to the personal monitoring device 10 via the central processing computer 20.

In a preferred embodiment, at step 1005, the personal monitoring device 10 and/or the CPU 10A, and/or the user communication device 30, and/or the central processing computer 20, and/or any authorized law enforcement communication device(s) 40 or any authorized emergency services provider communication device(s) 50, can continue tracking the child's position or location by using the position or location data and/or information obtained by the GPS device 10K and transmitted from the personal monitoring device 10. In a preferred embodiment, the personal monitoring device 10 and/or the CPU 10A, and/or the user communication device 30, and/or the central processing computer 20, and/or any authorized law enforcement communication device(s) 40 or any authorized emergency services provider communication device(s) 50, at any pre-defined or pre-selected time interval, which in a preferred embodiment can be one (1) minute or any other suitable time interval, and while any and/or all functionality described herein as being performed at step 1005, can determine if the child has made it back to the place, position, or location where he or she is supposed to be at that time, and/or can determine if the child has made his or her way back to the travel route, and/or can determine if the child has been found. In this regard, the operation of the apparatus 100 can proceed to step 1006 and the personal monitoring device 10 and/or the CPU 10A, and/or the user communication device 30, and/or the central processing computer 20, and/or any authorized law enforcement communication device(s) 40 or any authorized emergency services provider communication device(s) 50, can determine if the child is back at the place, position, or location where he or she is supposed to be at that time, can determine if the child has made it back to the travel route, and/or can determine if the child has been found and that an instruction to reset the personal monitoring device 10 has been received by the personal monitoring device 10 or has been input into the personal monitoring device 10.

If, at step 1006, it is determined that the child is back at the place, position, or location where he or she is supposed to be at that time, is back on the travel route, and/or that the child has been found and that an instruction to reset the personal monitoring device 10 has been received by the personal monitoring device 10 or has been input into the personal monitoring device 10, then the operation of the apparatus 100 will cease at step 1007. Thereafter, the personal monitoring device 10 can be reset for future use. If at step 1006, it is determined that the child has still not made it back to the place, position, or location where he or she is supposed to be at that time, has not made it back to the travel route, and/or that the child has not been found, and that an instruction to reset the personal monitoring device 10 has been received by the personal monitoring device 10 or has been input into the personal monitoring device 10, then the operation of the apparatus 100 will return to, or continue on as described during, step 1005 as described herein. The apparatus 100 will thereafter continue to function and/or operate at steps 1005 and 1006 until it is determined by the personal monitoring device 10 and/or the CPU 10A that the child is back at the place, position, or location, where he or she is supposed to be, or is back on his or her travel route, or that the child has been found, or until an instruction to reset the personal monitoring device 10 has been received by the personal monitoring device 10 or has been input into the personal monitoring device 10.

Although described herein as being utilized to monitor a child, it is important to note that the apparatus 100 and the personal monitoring device 10 of FIGS. 10A and 10B can be utilized in a same, a similar, and/or an analogous, manner to monitor individuals of any age, including but not limited to infants, children, adolescents, teenagers, adults of any age, elderly individuals, individuals having no healthcare issues, conditions, problems, or challenges, and/or individuals having healthcare issues, conditions, problems, or challenges. The apparatus 100 and method of the present invention as well as the apparatus of FIGS. 10A and 10B can be used to monitor children who may be afflicted with autism, or any disabilities, or who may lack communications skills, and/or who may have other conditions, as well as individuals of any age who are afflicted with Alzheimer's disease or Dementia, o any other healthcare conditions. The apparatus 100 and method of the present invention as well as the apparatus of FIGS. 10A and 10B can also be used to monitor individuals of any age who may have no healthcare conditions or problems, but who might want to simply utilize the apparatus 100 and method of the present inventions for the numerous benefits it can provide.

In a preferred embodiment, any of the functions and/or functionality described herein as being performed by the personal monitoring device 10 at or during step 1005 can be pre-programmed into the personal monitoring device 10 beforehand by any authorized individual and/or by a monitoring individual. In a preferred embodiment, any of the functions and/or functionality described herein as being performed by the personal monitoring device 10 at or during step 1005 can be changed or can be re-programmed at any time. In another preferred embodiment, any functions and/or functionality described herein as being performed by the personal monitoring device 10 at or during step 1005 can also be enabled, disabled, activated, deactivated, or controlled, or monitored, by or via the user communication device 30, the central processing computer 20, the law enforcement communication device 40, or the emergency services provider communication device 50.

In another preferred embodiment, as well as in any and/or all of the embodiments described herein, the apparatus 100 and/or the personal monitoring device 10 can also be utilized to record information regarding any incidents of bullying, harassment, criminal acts, or any other activities or events, perpetrated on, inflicted upon, or occurring involving the monitored individual and/or occurring in the vicinity of the monitored individual. In such an embodiment, the personal monitoring device 10 can be activated to record audio information and/or video information regarding the event or the occurrence, the position or location of same, date and time of same, and/or any other pertinent information regarding same which can be obtained by, with, or using, the personal monitoring device 10. In a preferred embodiment, a monitored individual can manually activate the personal monitoring device 10. In another preferred embodiment, the personal monitoring device 10 can be equipped with voice activation equipment and/or hardware and/or software and can be activated to record any information regarding an event or occurrence by, or in response to, a voice activation command. In a preferred embodiment, any data and/or information recorded can be stored in the database 10H of the personal monitoring device 10 and/or can be transmitted to the user communication device(s) 30 of or associated with the monitoring individual, the central processing computer 20, and/or to any one of more law enforcement communication devices 40 and/or emergency services provider communication devices 50, for reporting and for storing as evidence.

The apparatus 100 and method of the present invention can be utilized in order to provide and support comprehensive personal monitoring services of a global nature for individuals of any age. The apparatus 100 and method of the present invention can also be utilized in order to provide and support comprehensive personal monitoring services of a global nature for individuals of any age and regardless of whether or not they have any conditions, illnesses, sicknesses, disabilities, or health conditions. The apparatus 100 and method of the present invention can also be utilized to provide and service personal monitoring accounts for any number of individuals, with such personal monitoring accounts facilitating the providing of personal monitoring services by and/or involving any number of various monitoring services providers, security services provider, healthcare providers, healthcare insurers, healthcare records service providers, and/or healthcare payers, and/or law enforcement agencies and/or departments, and/or emergency services providers agencies and/or departments.

In another preferred embodiment, as well as any and/or all of the embodiments described herein, any of the herein-described personal monitoring device(s) 10, user communication devices 30, law enforcement communication devices 40, and/or emergency services provider communications devices 50, can be configured and/or adapted to work in an entirely hands-free mode of operation. In this regard, any of the herein-described personal monitoring device(s) 10, user communication devices 30, law enforcement communication devices 40, and/or emergency services provider communications devices 50, can be configured and/or adapted so that they, as well as any operation or functionality of same, can be activated, deactivated, enabled, disabled, controlled, or monitored, by voice-activation, so that any data, information, commands, directions, or instructions, can be input be entered by voice command, and/or so that or so that any data, information, commands, directions, or instructions, can be provided by or from the respective device 10, 30, 40, and/or 50, in the form of audio or audio information.

In another preferred embodiment, any of the herein-described personal monitoring devices 10, user communication devices 30, law enforcement communication devices 40, and/or emergency services provider communications devices 50, can each be equipped with any needed or desired hardware, circuitry, software, software programs, algorithms, and/or software applications ("apps") for performing any and/or all of their respective functions and operations described herein. In another preferred embodiment, any of the herein-described personal monitoring devices 10, user communication devices 30, law enforcement communication devices 40, and/or emergency services provider communications devices 50, can each be equipped with a "kill" switch functionality so that, if lost or stolen, the respective device(s) 10, 30, 40, and/or 50, cannot be utilized by and/or cannot be misappropriated by another individual or person and any data and/or information stored therein can be erased and destroyed completely.

While the present invention has been described and illustrated in various preferred and alternate embodiments, such descriptions are merely illustrative of the present invention and are not to be construed to be limitations thereof. In this regard, the present invention encompasses all modifications, variations, and/or alternate embodiments, with the scope of the present invention being limited only by the claims which follow.

What is claimed is:

1. An apparatus, comprising:
a housing;
a display, wherein the display is located on a first side of the housing;
a keyboard, wherein the keyboard is located on the first side of the housing or is a touch screen keyboard accessible via the display;
at least one microphone;
at least one speaker;
at least two cameras, wherein a first camera of the at least two cameras is located on the first side of the housing, and wherein a second camera of the at least two cameras is located on a second side of the housing or on a third side of the housing;
a memory or database, wherein the memory or database stores information regarding a travel schedule or itinerary for a first individual, wherein the information regarding the travel schedule or itinerary includes information regarding at least one destination to which the first individual is expected to travel, information regarding a first time at which the first individual is expected to travel from a first location to the destination, information regarding an expected travel route to the destination, information regarding a second time at which the first individual is expected to arrive at the destination, information regarding a third time at which the first individual is expected to leave the destination to travel back to the first location or to travel to a second destination, information regarding an expected travel route to the first location or to the second destination, and information regarding an expected time of arrival at the first location or the second destination;
a global positioning device, wherein the global positioning device determines a position or a location of the apparatus;
communication equipment, wherein the communication equipment include cellular telephone communication equipment or wireless telephone communication equipment;
a controller, wherein the controller is specially programmed to control an operation of the apparatus, and further wherein the controller is specially programmed to automatically and continuously monitor a location of the apparatus and to compare the location of the apparatus with the travel schedule or itinerary of the first individual; and
a transmitter,
wherein the controller is specially programmed to detect a deviation of the apparatus from the travel schedule or itinerary or to detect an absence of, or a leaving of, the apparatus from an expected location on the travel schedule or itinerary, at a time at which the apparatus is expected to be at the expected location, and wherein, if the controller detects a deviation of the apparatus from the travel schedule or itinerary or detects an absence of, or a leaving of, the apparatus from the expected location on the travel schedule or itinerary at a time at which the apparatus is expected to be at the expected location, the controller generates a travel route deviation message containing information regarding a time and a place of the detection of the deviation or the absence and a current position or location of the apparatus, and further wherein the transmitter transmits the travel route deviation message to a first communication device, wherein the first communication device is associated with a second individual, and further wherein the controller activates the communication equipment to initiate a telephone call to the first communication device or to a second communication device, de-activates an on/off switching functionality of the apparatus to prevent the apparatus from being turned off, and deactivates a telephone calling on/off switching functionality to prevent the telephone call from being terminated.

2. The apparatus of claim 1, wherein the apparatus generates an updated travel route deviation message and transmits the updated travel route deviation message to the first communication device.

3. The apparatus of claim 1, wherein the housing is wearable or is attachable to clothing.

4. The apparatus of claim 1, further comprising:
an indicator light located on the housing or provided via the display, wherein the indicator light indicates that the apparatus has deviated from a travel route on the travel schedule or itinerary or that the apparatus is not located at an expected location according to the travel schedule or itinerary.

5. The apparatus of claim 1, further comprising:
a pulse rate monitor for monitoring a pulse rate of the first individual, a heart rate monitor for monitoring a heart rate of the first individual, a blood pressure monitor for monitoring a blood pressure of the first individual, a blood alcohol monitor for monitoring a blood alcohol level of the first individual, or a thermometer for monitoring a body temperature of the first individual, wherein the travel route deviation message also contains information regarding the pulse rate, the heart rate, the blood pressure, the blood alcohol level, or the body temperature, of the first individual.

6. The apparatus of claim 1, wherein the travel route deviation message also contains information regarding the temperature of the environment in which the apparatus is located.

7. The apparatus of claim 1, wherein the communication equipment is cellular telephone communication equipment.

8. The apparatus of claim 1, wherein the apparatus is integrated within a watch, a wristwatch, a bracelet, a necklace, or an article of jewelry.

9. The apparatus of claim 1, wherein the controller is specially programmed to disable the apparatus.

10. The apparatus of claim 1, wherein the apparatus records audio information and video information at the apparatus or in a vicinity of the apparatus, and further wherein the apparatus transmits the audio information or the video information to the first communication device, to the second communication device, to a third communication device, or to a central processing computer.

11. The apparatus of claim 1, wherein the controller is specially programmed to detect a disconnected telephone call with the first communication device or with the second communication device or a dropped telephone call with the first communication device or with the second communication device, and further wherein the apparatus is programmed to automatically re-connect the telephone call between the apparatus and the first communication device or between the apparatus and the second communication device.

12. The apparatus of claim 1, wherein the transmitter transmits the travel route deviation message to a central processing computer or to a third communication device, wherein the third communication device is associated with a law enforcement agency.

13. The apparatus of claim 1, wherein the transmitter transmits the travel route deviation message to a central processing computer or to a third communication device, wherein the third communication device is associated with an emergency services provider.

14. The apparatus of claim 1, further comprising:
a homing beacon, wherein the homing beacon emits a distress signal.

15. The apparatus of claim 1, wherein the at least one speaker and the at least one microphone facilitate a hands-free telephone calling mode of operation of the apparatus or a hands-free mode of operation of the apparatus.

16. The apparatus of claim 1, further comprising:
a camera or a video recording device, wherein the camera or the video recording device records a picture or a video clip, and further wherein the apparatus transmits the picture or the video clip to the first communication device, to the second communication device, to a third communication device, or to a central processing computer.

17. The apparatus of claim 16, wherein the apparatus facilitates a video conference or a video chat via the apparatus and the first communication device.

18. The apparatus of claim 1, wherein the controller is specially programmed to determine a speed of travel or movement of the apparatus, and further wherein the apparatus transmits information regarding the speed of travel or movement to the first communication device, to the second communication device, to a third communication device, or to a central processing computer.

19. The apparatus of claim 1, wherein the apparatus is specially programmed to generate a plurality of tracking update messages containing information regarding the location of the first individual and a speed of travel or movement of the first individual, wherein each tracking update message of the plurality of tracking update messages is generated at a pre-determined time interval, and further wherein the apparatus is programmed to transmit each tracking update message of the plurality of tracking update messages to the first communication device.

20. The apparatus of claim 1, wherein the apparatus is specially programmed to process navigation information or to provide navigation information.

21. The apparatus of claim 1, wherein the apparatus is specially programmed to display information regarding the first individual's movement on a digital or satellite map via the display.

22. The apparatus of claim 1, further comprising:
a second display, wherein the second display is a component of the first communication device, the second communication device, or a central processing computer, wherein the second display displays information regarding the first individual's movement on a digital or satellite map.

23. The apparatus of claim 1, wherein the apparatus is programmed to play a pre-recorded message, a video clip, or an audio clip, via the display and the at least one speaker, wherein the pre-recorded message contains information regarding the first individual, an instruction or information regarding providing care for the first individual, information regarding a medication or drug required for the first individual, or information regarding a special need or a healthcare need of the first individual.

24. The apparatus of claim 1, wherein the apparatus is specially programmed to automatically detect that the first individual has made it back onto a travel route.

25. The apparatus of claim 1, wherein the apparatus receives a request for information from the first communication device or from the second communication device, and further wherein the apparatus transmits the travel route deviation message in response to the request for information.

26. The apparatus of claim 1, wherein the apparatus receives a control signal transmitted from the first communication device or from the second communication device, and further wherein the apparatus or the controller performs a control operation on or at the apparatus in response to the control signal.

27. The apparatus of claim 1, wherein the apparatus receives a control signal transmitted from a central processing computer, and further wherein the apparatus or the controller performs a control operation on or at the apparatus in response to the control signal.

28. The apparatus of claim 1, wherein the apparatus transmits the travel route deviation message to the second communication device, a third communication device, or a central processing computer.

29. The apparatus of claim 1, wherein the apparatus is specially programmed to generate a tracking update message containing information regarding the location of the first individual or a speed of travel or movement of the first individual, and further wherein the apparatus is programmed to transmit the tracking update message to the first communication device, to the second communication device, to a third communication device, or to a central processing computer.

30. The apparatus of claim 1, further comprising:
a blood sugar level monitor for monitoring a blood sugar level of the first individual,
wherein the travel route deviation message also contains information regarding the blood sugar level of the first individual.

* * * * *